(12) United States Patent
Hickman et al.

(10) Patent No.: US 10,160,953 B2
(45) Date of Patent: *Dec. 25, 2018

(54) METHOD FOR CULTURING SKELETAL MUSCLE FOR TISSUE ENGINEERING

(71) Applicant: UNIVERSITY OF CENTRAL FLORIDA RESEARCH FOUNDATION, INC., Orlando, FL (US)

(72) Inventors: James J. Hickman, Orlando, FL (US); Mainak Das, Orlando, FL (US); John W. Rumsey, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 215 days.

This patent is subject to a terminal disclaimer.

(21) Appl. No.: 14/886,577

(22) Filed: Oct. 19, 2015

(65) Prior Publication Data

US 2016/0068812 A1 Mar. 10, 2016

Related U.S. Application Data

(63) Continuation of application No. 12/765,399, filed on Apr. 22, 2010, now Pat. No. 9,163,216.

(60) Provisional application No. 61/171,968, filed on Apr. 23, 2009.

(51) Int. Cl.
C12N 5/077 (2010.01)
C12N 5/0793 (2010.01)

(52) U.S. Cl.
CPC ......... *C12N 5/0652* (2013.01); *C12N 5/0619* (2013.01); *C12N 5/0658* (2013.01); *C12N 2500/05* (2013.01); *C12N 2500/46* (2013.01); *C12N 2500/90* (2013.01); *C12N 2500/99* (2013.01); *C12N 2501/40* (2013.01); *C12N 2502/1335* (2013.01); *C12N 2533/30* (2013.01)

(58) Field of Classification Search
CPC .. C12N 5/0652; C12N 5/0619; C12N 5/0658; C12N 2501/40; C12N 2500/90; C12N 2500/46; C12N 2500/05; C12N 2533/30; C12N 2500/99; C12N 2502/1335
See application file for complete search history.

(56) References Cited

U.S. PATENT DOCUMENTS

| | | |
|---|---|---|
| 5,442,510 A | 8/1995 | Schwartz et al. |
| 5,948,621 A | 9/1999 | Turner et al. |
| 6,866,383 B2 | 3/2005 | Naik et al. |
| 6,916,541 B2 | 7/2005 | Pantano et al. |
| 6,935,165 B2 | 8/2005 | Bashir et al. |
| 7,384,786 B2 | 6/2008 | Freyman et al. |
| 7,541,146 B2 | 6/2009 | Lewis |
| 7,579,189 B2 | 8/2009 | Freyman et al. |
| 7,691,629 B2 | 4/2010 | Johe et al. |
| 7,923,015 B2 | 4/2011 | Vazquez-Martinez et al. |
| 7,927,671 B2 | 4/2011 | Kato |
| 8,071,319 B2 | 12/2011 | Metzeger et al. |
| 8,178,602 B2 | 5/2012 | Mao et al. |
| 8,318,488 B1 | 11/2012 | Bohlen et al. |
| 8,318,489 B2 | 11/2012 | Davidson et al. |
| 8,318,951 B2 | 11/2012 | Olson et al. |
| 2003/0065452 A1 | 4/2003 | Hickman |
| 2003/0144823 A1 | 7/2003 | Fox et al. |

(Continued)

FOREIGN PATENT DOCUMENTS

| | | |
|---|---|---|
| CA | 2788905 | 8/2011 |
| CA | 2798777 | 10/2011 |

(Continued)

OTHER PUBLICATIONS

Das-BM-09, Das et al., Skeletal Muscle Tissue Engineering: A Maturation Model Promoting Long Term Survival of Myotubes, Structural Development of the Excitation—Contraction Coupling Apparatus and Neonatal Myosin Heavy Chain Expression, Biomaterials. Oct. 2009; 30(29): 5392-5402. doi:10.1016/j.biomaterials.2009.05.081.*
Das-Thesis, Das. M, PhD Thesis, Tissue Engineering The Motoneuron to Muscle Segment of The Stretch Reflex Arc Circuit Utilizing Micro-fabrication, Interface Design and Defined Medium Formulation, Fall 2008, University of Central Florida.*
Abbanat D, et al. (2003) Novel antibacterial agents for the treatment of serious Gram-positive infections. Expert Opin Investig Drugs. 12: 379-399.
Abdi H. (2003) Multivariate Analysis. Encyclopedia of Social Sciences Research Methods. M. Lewis-Beck, A. Bryman and T. Futing. Thousand Oaks (CA), Sage.

(Continued)

*Primary Examiner* — Renee Claytor
*Assistant Examiner* — Srikanth Patury
(74) *Attorney, Agent, or Firm* — Meunier Carlin & Curfman LLC

(57) ABSTRACT

The invention provides a nutrient medium composition and associated methods for lengthening the useful life of a culture of muscle cells. Disclosed is a method of culturing mammalian muscle cells, including preparing one or more carriers coated with a covalently bonded monolayer of trimethoxy-silylpropyl-diethylenetriamine (DETA); verifying DETA monolayer formation by one or more associated optical parameters; suspending isolated fetal rat skeletal muscle cells in serum-free medium according to medium composition 1; plating the suspended cells onto the prepared carriers at a predetermined density; leaving the carriers undisturbed for cells to adhere to the DETA monolayer; covering the carriers with a mixture of medium 1 and medium 2; and incubating. A cell nutrient medium composition includes Neurobasal, an antibiotic-antimycotic composition, cholesterol, human TNF-alpha, PDGF BB, vasoactive intestinal peptides, insulin-like growth factor 1, NAP, r-Apolipoprotein E2, purified mouse Laminin, beta amyloid, human tenascin-C protein, rr-Sonic hedgehog Shh N-terminal, and rr-Agrin C terminal.

15 Claims, 10 Drawing Sheets

(56) References Cited

U.S. PATENT DOCUMENTS

| | | | |
|---|---|---|---|
| 2003/0211542 | A1 | 11/2003 | Lee et al. |
| 2006/0105457 | A1 | 5/2006 | Rameshwar |
| 2007/0015138 | A1 | 1/2007 | Barlow et al. |
| 2007/0117217 | A1 | 5/2007 | Lal et al. |
| 2007/0212723 | A1 | 9/2007 | Dudley et al. |
| 2008/0124789 | A1 | 5/2008 | Hickman |
| 2008/0227137 | A1 | 9/2008 | Zhang et al. |
| 2009/0029463 | A1 | 1/2009 | Collins |
| 2009/0239940 | A1 | 9/2009 | Del Monte et al. |
| 2009/0305319 | A1 | 12/2009 | Baudenbacher et al. |
| 2011/0250682 | A1 | 10/2011 | Hickman et al. |
| 2012/0122728 | A1 | 5/2012 | Hickman et al. |
| 2012/0128639 | A1 | 5/2012 | Hickman et al. |
| 2013/0096888 | A1 | 4/2013 | Hickman et al. |
| 2013/0115694 | A1 | 5/2013 | Hickman et al. |

FOREIGN PATENT DOCUMENTS

| | | |
|---|---|---|
| EP | 2434896 | 4/2012 |
| EP | 2435585 | 4/2012 |
| EP | 2531910 | 12/2012 |
| EP | 2585171 | 5/2013 |
| WO | WO 2010/138679 | 12/2010 |
| WO | WO 2010/138782 | 12/2010 |
| WO | WO 2011/097574 | 8/2011 |
| WO | WO 2011/133985 | 10/2011 |
| WO | WO 2012/158923 | 11/2012 |

OTHER PUBLICATIONS

Adell A, et al. (2002) Origin and functional role of the extracellular serotonin in the midbrain raphe nuclei. Brain Res Brain Res Rev. 39: 154-180.

Agarwal A, et al. (2013) Microfluidic heart on a chip for higher throughput pharmacological studies. Lab Chip. 13: 3599-3608.

Ahern CA, et al. (2003) Ca2+ current and charge movements in skeletal myotubes promoted by the beta-subunit of the dihydropyridine receptor in the absence of ryanodine receptor type 1. Biophys J. 84: 942-959.

Ahern CA, et al. (2003) Ca2+ current and charge movements in skeletal myotubes promoted by the beta-subunit of the dihydropyridine receptor in the absence of ryanodine receptor type 1. Biophys J. 84: 942-959.

Ahmari SE, et al. (2000) Assembly of presynaptic active zones from cytoplasmic transport packets. Nat Neurosci. 3: 445-451.

Ahuja TK, et al. (2007) Hippocampal slice cultures integrated with multi-electrode arrays: A model for study of long-term drug effects on synaptic activity. Drug Development Research. 68: 84-93.

Ainscow EK and Brand MD. (1999) Internal regulation of ATP turnover, glycolysis and oxidative phosphorylation in rat hepatocytes. Eur J Biochem. 266:737-749.

Akaaboune M, et al. (2000) Developmental regulation of amyloid precursor protein at the neuromuscular junction in mouse skeletal muscle. Mol Cell protein at the neuromuscular junction in mouse skeletal muscle. Mol Cell.

Akanda N, et al. (2008) Effect of malonate, a metabolic pathway inhibitor, on A124. action potential peak shape and the relationship to cellular pathways. 38th Annual Meeting of the Society for Neuroscience. vol. 3 8.

Akanda N, et al. (2009) Analysis of toxin-induced changes in action potential shape for drug development. J Biomol Screen. 14: 1228-1235.

Alabed YZ, et al. (2006) Neuronal responses to myelin are mediated by rho kinase. J Neurochem. 96: 1616-1625.

Albensi BC. (2003) A comparison of drug treatment versus electrical stimulation for suppressing seizure activity. Drug News Perspect. 16: 347-352.

Albert R and Othmer H. (2003) The topology of the regulatory interactions predicts the expression pattern of the segment polarity genes in *Drosophila melanogaster*. J Theor Biol. 223: 1-18.

Albert Y, et al. (2005) Transcriptional regulation of myotube fate specification and intrafusal muscle fiber morphogenesis. J Cell Biol. 169: 257-268.

Alexander SL, et al. (1989) An atomic-resolution atomic-force microscope implemented using an optical lever. J Appl Phys. 65: 164-167.

Al-Shanti N, et al. (2008) Beneficial synergistic interactions of TNF-alpha and IL-6 in C2 skeletal myoblasts—potential cross-talk with IGF system. Growth Factors. 26: 61-73.

Alsina B, et al. (2001) Visualizing synapse formation in arborizing optic axons in vivo: dynamics and modulation by BDNF. Nat Neurosci. 4: 1093-1101.

Alterio J, et al. (1990) Acidic and basic fibroblast growth factor mRNAs are expressed by skeletal muscle satellite cells. Biochem Biophys Res Commun. 166: 1205-1212.

Altmann L. (2000) Multielectrode recordings of synaptic plasticity in brain slices: A new method for the assessment of neurotoxic effects. European Journal of Neuroscience. 12: 29-29.

Amarenco P, et al. (2006) High-dose atorvastatin after stroke or transient ischemic attack. N Engl J Med. 355: 549-559.

Amit M. (2007) Feeder-layer free culture system for human embryonic stem cells. Methods Mol Biol. 407: 11-20.

Anderson JE, et al. (1991) Distinctive patterns of basic fibroblast growth factor (bFGF) distribution in degenerating and regenerating areas of dystrophic (mdx) striated muscles. Dev Biol. 147: 96-109.

Anderson DJ, et al. (1997) Cell lineage determination and the control of neuronal identity in the neural crest. Cold Spring Harb Symp Quant Biol. 62: 493-504.

Andersson H and van den Berg A. (2004) Microfabrication and microfluidics for tissue engineering: state of the art and future opportunities. Lab Chip. 4: 98-103.

Antzelevitch C. (2001) Transmural dispersion of repolarization and the T wave. Cardiovasc Res. 50: 426-431.

Antzelevitch C. (2005) Cardiac repolarization. The long and short of it. Europace. 7: 3-9.

Aracil A, et al. (2004) Proceedings of Neuropeptides 2004, the XIV European Neuropeptides Club meeting. Neuropeptides. 38: 369-371.

Archer JD, et al. (2006) Persistent and improved functional gain in mdx dystrophic mice after treatment with L-arginine and deflazacort. F ASEB J. 20:738-740.

Armstrong DL and Rossie S. (1999) Ion channel regulation. Introduction. Adv Second Messenger Phosphoprotein Res. 33: ix-xx.

Arnold HH, et al. (1998) Muscle differentiation: more complexity to the network of myogenic regulators. Curr Opin Genet Dev. 8: 539-544.

Arnone MI and Davidson EH. (1997) The hardwiring of development: organization and function of genomic regulatory systems. Development. 124:1851-1864.

Arsic N, et al. (2004) Vascular endothelial growth factor stimulates skeletal muscle regeneration in vivo. Mol Ther. 10: 844-854.

Askanas V, et al. (1987) De novo neuromuscular junction formation on human muscle fibres cultured in monolayer and innervated by foetal rat spinal cord: ultrastructural and ultrastructural—cytochemical studies. J Neurocytol. 16: 523-537.

Asotra K and Macklin WB. (1993) Protein kinase C activity modulates myelin gene expression in enriched oligodendrocytes. J Neurosci Res. 34: 571-588.

Azzouz M, et al. (2004) VEGF delivery with retrogradely transported lentivector prolongs survival in a mouse ALS model. Nature. 429: 413-417.

Badie N, et al. (2009) A method to replicate the microstructure of heart tissue in vitro using DTMRI-based cell micropatterning. Ann Biomed Eng. 37: 2510-2521.

Bahr M, et al. (1991) In vitro myelination of regenerating adult rat retinal ganglion cell axons by Schwann cells. Glia. 4: 529-533.

Baker DC, et al. (2002) The origin and neuronal function of in vivo nonsynaptic glutamate. J Neurosci. 22: 9134-9141.

Bandi E, et al. (2008) Neural agrin controls maturation of the excitation-contraction coupling mechanism in human myotubes developing in vitro. Am J Physiol Cell Physiol. 294: C66-C73.

(56) References Cited

OTHER PUBLICATIONS

Bansal R and Pfeiffer SE. (1992) Novel stage in the oligodendrocyte lineage defined by reactivity of progenitors with R-mAb pnor to QI antigalactocerebroside. J Neurosci Res. 32: 309-316.

Baraban SC, et al. (1997) Osmolarity modulates K+ channel function on rat A156. hippocampal interneurons but not CAI pyramidal neurons. J Physiol. 498: 679-689.

Barbulovic-Nad I, et al. (2008) Digital microfluidics for cell-based assays. Lab Chip. 8: 519-526.

Baron W, et al. (2000) PDGF and FGF-2 signaling in oligodendrocyte progenitor cells: regulation of proliferation and differentiation by multiple intracellular signaling pathways. Mol Cell Neurosci. 15: 314-329.

Barone FC, et al. (1998) Ischemic preconditioning and brain tolerance: temporal histological and functional outcomes, protein synthesis requirement, and interleukin-I receptor antagonist and early gene expression. Stroke. 29: 1937-1950.

Behar TN. (2001) Analysis of fractal dimension of O2A glial cells differentiating in vitro. Methods. 24: 331-339.

Belardinelli L, et al. (2003) Assessing predictors of drug-induced torsade de pointes. Trends Pharmacol Sci. 24: 619-625.

Bellamkonda R, et al. (1995) Hydrogel-based three-dimensional matrix for neural cells. J Biomed Mater Res. 29: 663-671.

Bellas E, et al. (2012) In vitro 3D full-thickness skin-equivalent tissue model using silk and collagen biomaterials. Macromol Biosci. 12: 1627-1236.

Benabid AI. (2003) Deep brain stimulation for Parkinson's disease. Curr Opin Neurobiol. 13: 696-706.

Bender A, et al. (2007) Analysis of pharmacology data and the prediction of adverse drug reactions and off-target effects from chemical structure. ChemMedChem. 2: 861-873.

Bentley A and Atkinsona, A. (2001) Whole cell biosensors—electrochemical and optical approaches to ecotoxicity testing. Toxicol In Vitro. 15: 469-475.

Berg MC, et al. (2004) Controlling mammalian cell interactions on patterned polyelectrolyte multilayer surfaces. Langmuir. 20: 1362-1368.

Berger TW, et al. (2001) Brain-implantable biomimetic electronics as the next era in neural prosthetics. Proceedings of the IEEE. 89: 993-1012.

Bernstein M, et al. (1996) Receptor-mediated calcium signalling in glial cells from mouse corpus callosum slices. J Neurosci Res. 46: 152-163.

Bers DM. (2002) Cardiac excitation-contraction coupling. Nature. 415: 198-205.

Bettinger CJ, et al. (2009) Engineering substrate topography at the micro- and nanoscale to control cell function. Angew Chem Int Ed Engl. 48: 5406-5415.

Bhalla US and Iyengar R. (1999) Emergent properties of networks of biological signaling pathways. Science. 283: 381-387.

Bhat NR, et al. (2007) p38 MAP kinase regulation of oligodendrocyte differentiation with CREB as a potential target. Neurochem Res. 32: 293-302.

Bian WN and Tung L. (2006) Structure-related initiation of reentry by rapid pacing in monolayers of cardiac cells. Circ Res. 98: e29-38.

Biesecker G. (1990) The complement SC5b-9 complex mediates cell adhesion through a vitronectin receptor. J Immunol. 145: 209-214.

Bikfalvi A, et al. (1997) Biological roles of fibroblast growth factor-2. Endocr Rev. 18: 26-45.

Bischoff U, et al. (2000) Effects of fluoroquinolones on HERG currents. Eur J Pharmacol. 406: 341-343.

Bloch-Gallego E, et al. (1991) Survival in vitro of motoneurons identified or purified by novel antibody-based methods is selectively enhanced by musclederived factors. Development. 111: 221-232.

Bodine SC, et al. (2001) Identification of ubiquitin ligases required for skeletal muscle atrophy. Science. 294: 1704-1708.

Bogler O, et al. (1990) Cooperation between two growth factors promotes extended self-renewal and inhibits differentiation of oligodendrocyte-type-2 astrocyte (0-2A) progenitor cells. Proc Natl Acad Sci US A. 87: 6368-6372.

Boillee S, et al. (2006) ALS: a disease of motor neurons and their nonneuronal neighbors. Neuron. 52: 39-59.

Boldin SA and Futerman AH. (2000) Up-regulation of glucosylceramide synthesis upon stimulation of axonal growth by basic fibroblast growth factor. Evidence for post-translational modification of glucosylceramide synthase. J Biol Chem. 275: 9905-9909.

Bordet T, et al. (2001) Protective effects of cardiotrophin-1 adenoviral gene transfer on neuromuscular degeneration in transgenic ALS mice. Hum Mol Genet. 10: 1925-1933.

Bottenstein JE, et al. (1988a) CNS neuronal cell line-derived factors regulate gliogenesis in neonatal rat brain cultures. J Neurosci Res. 20: 291-303.

Bottenstein JE. (1981) Proliferation of glioma cells in serum-free defined medium. Cancer Treat Rep. 65 Suppl 2: 67-70.

Bottenstein JE. (1988b) Advances in vertebrate cell culture methods. Science. 239: G 42, G 48.

Bourgeois EB, et al. (2009) Change in conduction velocity due to fiber curvature in cultured neonatal rat ventricular myocytes. IEEE Trans Biomed Eng. 56: 855-861.

Bousse L. (1996) Whole cell biosensors. Sens Actuators B: Chem. 34: 270-275.

Bowman WC. (2006) Neuromuscular block. Br J Pharmacol. 147 Suppl 1: S277-S286.

Bracciali A, et al. (2008) Stochastic models for the in silico simulation of synaptic processes. BMC Bioinformatics. 9 Suppl 4: S7.

Brand T, et al. (2000) EMBO Workshop Report: Molecular genetics of muscle development and neuromuscular diseases Kloster Irsee, Germany, Sep. 26-Oct. 1, 1999. EMBO J. 19: 1935-1941.

Brand-Saberi B, et al. (1999) Genetic and epigenetic control of muscle development in vertebrates. Cell Tissue Res. 296: 199-212.

Brand-Saberi B. (2005) Genetic and epigenetic control of skeletal muscle development. Ann Anat. 187: 199-207.

Bregman BS, et al. (1997) Neurotrophic factors increase axonal growth after spinal cord injury and transplantation in the adult rat. Exp Neurol. 148: 475-494.

Bren-Mattison Y, et al. (2002) Sonic hedgehog inhibits the terminal differentiation oflimb myoblasts committed to the slow muscle lineage. Dev Biol. 242: 130-148.

Brewer GJ, et al. (1993) Optimized survival of hippocampal neurons in B27-supplemented Neurobasal, a new serum-free medium combination. J Neurosci Res. 35: 567-576.

Brewer GJ, et al. (2008) NbActiv4 medium improvement to Neurobasal/B27 increases neuron synapse densities and network spike rates on multielectrode arrays. J Neurosci Methods. 170: 181-187.

Brito-Martins M, et al. (2008) beta(1)- and beta(2)-adrenoceptor responses in cardiomyocytes derived from human embryonic stem cells: comparison with failing and non-failing adult human heart. Br J Pharmacol. 153: 751-759.

Brockes JP, et al. (1979) Studies on cultured rat Schwann cells. I. Establishment of purified populations from cultures of peripheral nerve. Brain Res. 165: 105-118.

Brokhman I, et al. (2008) Peripheral sensory neurons differentiate from neural precursors derived from human embryonic stem cells. Differentiation. 76: 145-155.

Brumovsky P, et al. (2007) Expression of the vesicular glutamate transporters-1 and -2 in adult mouse dorsal root ganglia and spinal cord and their regulation by nerve injury. Neuroscience. 147: 469-490.

Bult CJ, et al. (1996) Complete genome sequence of the methanogenic archaeon, Methanococcus jannaschii. Science. 273: 1058-1073.

Bunge MB, et al. (1962) Electron microscopic demonstration of connections between glia and myelin sheaths in the developing mammalian central nervous system. J Cell Biol. 12: 448-453.

Bunge RP. (1968) Glial cells and the central myelin sheath. Physiol Rev. 48: 197-251.

Bunge RP. (1993) Expanding roles for the Schwann cell: ensheathment, myelination, trophism and regeneration. Curr Opin Neurobiol. 3: 805-809.

(56) References Cited

OTHER PUBLICATIONS

Burdick JA and Vunjak-Novakovic G. (2008) Engineered microenvironments for controlled stem cell differentiation. Tissue Eng Part A. 15: 205-219.
Burgess C, et al. (2008) An endogenous glutamatergic drive onto somatic motoneurons contributes to the stereotypical pattern of muscle tone across the sleep-wake cycle. J Neurosci. 28: 4649-4660.
Butt HJ. (1996) Sensitive Method to Measure Changes in the Surface Stress of Solids. Journal of Colloid and Interface Science. 180: 251-260.
Buzanska L, et al. (2002) Human cord blood-derived cells attain neuronal and glial features in vitro. J Cell Sci. 115: 2131-2138.
Cai J, et al. (2007) Directed differentiation of human embryonic stem cells into functional hepatic cells. Hepatology. 45: 1229-1239.
Caiozzo VJ, at al. (1992) Response of slow and fast muscle to hypothyroidism: maximal shortening velocity and myosin isoforms. Am J Physiol. 263: C86-C94.
Cakir T, et al. (2007) Reconstruction and flux analysis of coupling between metabolic pathways of astrocytes and neurons: application to cerebral hypoxia. Theor Biol Med Model. 4: 48.
Campbell TJ and Williams KM. (2001) Therapeutic drug monitoring: antiarrhythmic drugs. Br J Clin Pharmacol. 52 Suppl 1: 21S-34S.
Camu W and Henderson CE. (1994) Rapid purification of embryonic rat motoneurons: an in vitro model for studying MND/ALS pathogenesis. J Neurol Sci. 124 Suppl: 73-74.
Camu Wand Henderson CE. (1992) Purification of embryonic rat motoneurons by panning on a monoclonal antibody to the low-affinity NGF receptor. J Neurosci Methods. 44: 59-70.
Cannon JG. (1998) Intrinsic and extrinsic factors in muscle aging. Ann N Y Acad Sci. 854: 72-77.
Caratsch CG, et al. (1994) Interferon-alpha beta and tumor necrosis factor-alpha enhance the frequency of miniature end-plate potentials at rat neuromuscular junction. Neurosci Lett. 166: 97-100.
Carlsson L. (2006) In vitro and in vivo models for testing arrhythmogenesis in drugs. J Intern Med. 259: 70-80.
Carpenedo RL, et al. (2007) Rotary suspension culture enhances the efficiency, yield, and homogeneity of embryoid body differentiation. Stem Cells. 25: 2224-2234.
Carr PA, et al. (1989) Parvalbumin is highly colocalized with calbindin D28k and rarely with calcitonin gene-related peptide in dorsal root ganglia neurons of rat. Brain Res. 497: 163-170.
Carrasco DI, et al. (2003) Neurotrophin 4/5 is required for the normal development of the slow muscle fiber phenotype in the rat soleus. J Exp Biol. 206: 2191-2200.
Caspi O, et al. (2009) In vitro electrophysiological drug testing using human embryonic stem cell derived cardiomyocytes. Stem Cells Dev. 18: 161-172.
Catoire H, et al. (2008) Sirtuin inhibition protects from the polyalanine muscular dystrophy protein PABPN1. Hum Mol Genet. 17: 2108-2117.
Cerignoli F, et al. (2012) High throughput measurement of Ca2+ dynamics for drug risk assessment in human stem cell-derived cardiomyocytes by kinetic image cytometry. J Pharmacol Toxicol Methods. 66: 246-256.
Chambers SM, et al. (2009) Highly efficient neural conversion of human ES and iPS cells by dual inhibition of SMAD signaling. Nat Biotechnol. 27: 275-280.
Chandran S, et al. (1998) Regional potential for oligodendrocyte generation in the rodent embryonic spinal cord following exposure to EGF and FGF-2. Glia. 24: 382-389.
Chang JC, et al. (2001) Modulation of neural network activity by patterning. Biosens Bioelectron. 16: 527-533.
Charpentier A, et al. (1993) RRR-alpha-tocopheryl succinate inhibits proliferation and enhances secretion of transforming growth factor-beta (TGFbeta) by human breast cancer cells. Nutr Cancer. 19: 225-239.
Chaudhary KW, et al. (2006) Embryonic stem cells in predictive cardiotoxicity: laser capture microscopy enables assay development. Toxicol Sci. 90: 149-158.
Chaves M, et al. (2005) Robustness and fragility of Boolean models for genetic regulatory networks. J Theor Biol. 235: 431-449.
Chaves M, et al. (2006) Methods of robustness analysis for Boolean models of gene control networks. Syst Biol (Stevenage). 153: 154-167.
Chen X, et al. (2005) Dedifferentiation of adult human myoblasts induced by ciliary neurotrophic factor in vitro. Moll Biol Cell. 16: 3140-3151.
Chen CS, et al. (1997) Geometric control of cell life and death. Science. 276: 1425-1428.
Chen EW, et al. (1995) Target regulation of a motor neuron-specific epitope. J Neurosci. 15: 1555-1566.
Chen J, et al. (2004) Role of exogenous and endogenous trophic factors in the regulation of extraocular muscle strength during development. Invest Ophthalmol Vis Sci. 45: 3538-3545.
Chen QS, et al. (2000) Impairment of hippocampal long-term potentiation by Alzheimer amyloid beta-peptides. J Neurosci Res. 60: 65-72.
Chen XF, et al. (2008) Dynamic simulation of the effect of calcium-release activated calcium channel on cytoplasmic Ca2+ oscillation. Biophys Chem. 136: 87-95.
Chen XP, (2003) [Exogenous rhCNTF inhibits myoblast differentiation of skeletal muscle of adult human in vitro]. Sheng Li Xue Bao. 55: 464-468.
Chiu A Y, et al. (1993) A motor neuron-specific epitope and the low-affinity nerve growth factor receptor display reciprocal patterns of expression during development, axotomy, and regeneration. J Comp Neurol. 328: 351-363.
Choi-Lundberg DL et al. (1995) Ontogeny and distribution of glial cell line-derived neurotrophic factor (GDNF) mRNA in rat. Brain Res Dev Brain Res. 85:80-88.
Choudhury A, et al. (2007) A piezoresistive microcantilever array for surface stress measurement: curvature model and fabrication. J Micromech Microeng. 17: 2065-2076.
Chow I and Poo MM. (1985) Release of acetylcholine from embryonic neurons upon contact with muscle cell. J Neurosci. 5: 1076-1082.
Christ B, et al. (2002) Limb muscle development. Int J Dev Biol. 46: 905-914.
Cizkova D, et al. (2007) Functional recovery in rats with ischemic paraplegia after spinal grafting of human spinal stem cells. Neuroscience. 147: 546-560.
Clegg CH, et al. (1987) Growth factor control of skeletal muscle differentiation: commitment to terminal differentiation occurs in G 1 phase and is repressed by fibroblast growth factor. J Cell Biol. 105: 949-956.
Clements JD, et al. (1992) The time course of glutamate in the synaptic cleft. Science. 258: 1498-1501.
Coggan JS, et al. (2005) Evidence for ectopic neurotransmission at a neuronal synapse. Science. 309: 446-451.
Cohen RI and Almazan G. (1993) Norepinephrine-stimulated PI hydrolysis in oligodendrocytes is mediated by alpha IA-adrenoceptors. Neuroreport. 4: 1115-1118.
Cohen-Cory S. (2002) The developing synapse: construction and modulation of synaptic structures and circuits. Science. 298: 770-776.
Collins CA and Morgan JE. (2003) Duchenne's muscular dystrophy: animal models used to investigate pathogenesis and develop therapeutic strategies. Int J Exp Pathol. 84: 165-172.
Colomar A and Robitaille R. (2004) Glial modulation of synaptic transmission at the neuromuscular junction. Glia. 4 7: 284-289.
Cooper A, et al. (1976) The growth of mouse neuroblastoma cells in controlled orientations on thin films of silicon monoxide. Exp Cell Res. 103: 435-439.
Corey JM, et al. (1996) Micrometer resolution silane-based patterning of hippocampal neurons: critical variables in photoresist and laser ablation processes for substrate fabrication. IEEE Trans Biomed Eng. 43: 944-955.
Corey JM, et al. (1991) Compliance of hippocampal neurons to patterned substrate networks. J Neurosci Res. 30: 300-307.

(56) References Cited

OTHER PUBLICATIONS

Corey JM, et al. (1997) Differentiated B 104 neuroblastoma cells are a highresolution assay for micro patterned substrates. J Neurosci Methods. 75: 91-97.

Cortassa S, et al. (2003) An integrated model of cardiac mitochondrial energy metabolism and calcium dynamics. Biophys J. 84: 2734-2755.

Cossu G, et al. (1996) How is myogenesis initiated in the embryo? Trends Genet. 12: 218-223.

Courdier-Fruh I, et al. (2002) Glucocorticoid-mediated regulation of utrophin levels in human muscle fibers. Neuromuscul Disord. 12(Suppl 1): S95-S104.

Cross-Doersen D and Isfort RJ. (2003) A novel cell-based system for evaluating skeletal muscle cell hypertrophy-inducing agents. In Vitro Cell Dev Biol Animal. 39: 407-412.

Cukierman E, et al. (2002) Cell interactions with three-dimensional matrices. Curr Opin Cell Biol. 14: 633-639.

Cunningham JJ and Roussel MF. (2001) Cyclin-dependent kinase inhibitors in the development of the central nervous system. Cell Growth Differ. 12: 387-396.

Cuppini R, et al. (2001) Alpha-tocopherol controls cell proliferation in the adult rat dentate 12:vrus. Neurosci Lett. 303: 198-200.

Currie PD, et al. (1996) Induction of a specific muscle cell type by a hedgehog-like protein in zebrafish. Nature. 382: 452-455.

Curtis R, et al. (1988) Development of macroglial cells in rat cerebellum. I. Use of antibodies to follow early m VIVO development and migration of oligodendrocytes. J Neurocytol. 17: 43-54.

Cysyk J and Tung L. (2008) Electric field perturbations of spiral waves attached to millimeter-size obstacles. Biophys J. 94: 1533-1541.

Dakhel Y and Jamali F. (2006) Erythromycin potentiates PR interval prolonging effect of verapamil in the rat: a pharmacodynamic drug interaction. Toxicol Appl Pharmacol. 214: 24-29.

Daniels MP, et al. (2000) Rodent nerve-muscle cell culture system for studies of neuromuscular junction development: refinements and applications. Microsc Res Tech. 49: 26-37.

Daniels MP. (1990) Localization of actin, beta-spectrin, 43 × 10(3) Mr and 58 × 10(3) Mr proteins to receptor-enriched domains of newly formed acetylcholine receptor aggregates in isolated myotube membranes. J Cell Sci. 97(Pt 4): 615-626.

Daniels MP. (1997) Intercellular communication that mediates formation of the neuromusculariunction. Mol Neurobiol. 14: 143-170.

Das M, et al. (2003) Electrophysiological and morphological characterization of rat embryonic motoneurons in a defined system. Biotechnol Prog. 19: 1756-1761.

Das M, et al. (2004) Long-term culture of embryonic rat cardiomyocytes on an organosilane surface in a serum-free medium. Biomaterials. 25: 5643-5647.

Das M, et al. (2005) Adult rat spinal cord culture on an organosilane surface in a novel serum-free medium. In Vitro Cell Dev Biol Anim. 41: 343-348.

Das M, et al. (2006) A defined system to allow skeletal muscle differentiation and subsequent integration with silicon microstructures. Biomaterials. 27: 4374-4380.

Das M, et al. (2007) Auto-catalytic ceria nanoparticles offer neuroprotection to adult rat spinal cord neurons. Biomaterials. 28: 1918-1925.

Das M, et al. (2007) Differentiation of skeletal muscle and integration of myotubes with silicon microstructures using serum-free medium and a synthetic silane substrate. Nat Protoc. 2: 1795-1801.

Das M, et al. (2007) Embryonic motoneuron-skeletal muscle co-culture in a defined system. Neuroscience. 146: 481-488.

Das M, et al. (2007b) Differentiation of skeletal muscle and integration of myotubes with silicon microstructures using serum-free medium and a synthetic silane substrate. Nat Protoc. 2: 1795-1801.

Das M, et al. (2008) Temporal neurotransmitter conditioning restores the functional activity of adult spinal cord neurons in long-term culture. Exp Neurol. 209: 171-180.

Das M, et al. (2009a) Developing a novel serum-free cell culture model of skeletal muscle differentiation by systematically studying the role of different growth factors in myotube formation. In Vitro Cell Dev Biol Anim. 45: 378-387.

Das M, et al. (2009b) Skeletal Muscle Tissue Engineering: An Improved Model Promoting Long Term Survival of Myotubes, Structural Development of E-C Coupling Apparatus and Neonatal Myosin Heavy Chain (MHC) Expression. Biomaterials. 30: 5392-5402.

Das M, et al. (2010) A defined long-term in vitro tissue engineered model of neuromuscular junctions. Biomaterials. 31: 4880-4888.

Datar R, et al. (2009) Cantilever Sensors: Nanomechanical Tools for Diagnostics. MRS Bulletin. 34: 449-454.

David JA and Pitman RM. (1982) The effects of axotomy upon the extrasynaptic acetylcholine sensitivity of an identified motoneurone m the cockroach Periplaneta americana. J Exp Biol. 98: 329-341.

Davis H, et al. (2012) Rat Cortical Oligodendrocyte-Embryonic Motoneuron Co-Culture: An in Vitro Axon-Oligodendrocyte Interaction Model. J Biomater Tissue Eng. 2: 206-214.

De Clerck F, et al. (2002) In vivo measurement of QT prolongation, dispersion and arrhythmogenesis: application to the preclinical cardiovascular safety pharmacology of a new chemical entity. Fundam Clin Pharmacol. 16: 125-140.

De Felice FG, et al. (2001) Inhibition of Alzheimer's disease beta-amyloid aggregation, neurotoxicity, and in vivo deposition by nitrophenols: implications for Alzheimer's therapy. FASEB J. 15: 1297-1299.

de Lange P, et al. (2006) Sequential changes in the signal transduction responses of skeletal muscle following food deprivation. FASEB J. 20: 2579-2581.

de Wilde J, et al. (2008) Short-term high fat-feeding results in morphological and metabolic adaptations m the skeletal muscle of C57BL/6J mice. Physiol Genomics. 32: 360-369.

Dell'Era P, et al. (2003) Fibroblast growth factor receptor-I is essential for in vitro cardiomyocyte development. Circ Res. 93: 414-420.

Denning C and Anderson D. (2008) Cardiomyocytes from human embryonic A291. stem cells as predictors of cardiotoxicity. Drug Discovery Today: Therapeutic Strategies. 5: 223-232.

Dennis RG and Kosnik IPE. (2000) Excitability and isometric contractile A292. properties of mammalian skeletal muscle constructs engineered in vitro. In Vitro Cell Dev Biol Anim. 36: 327-335.

Dennis RG, et al. (2001) Excitability and contractility of skeletal muscle A293. engineered from primary cultures and cell lines. Am J Physiol Cell Physiol. 280: C288-C295.

Denyer MCT, et al. (1998) Preliminary study on the suitability of a A294. pharmacological bio-assay based on cardiac myocytes cultured over microfabricated microelectrode arrays. Med Biol Eng Comput. 36: 638-644.

Descarries L, et al. (1997) Diffuse transmission by acetylcholine in the CNS. Prog Neurobiol. 53: 603-625.

Dhavan Rand Tsai L. (2001) A decade of CDK5. Nat Rev Mol Cell Biol. 2: 749-759.

Dhir V, et al. (2009) Patterning of diverse mammalian cell types in serum free medium with photoablation. Biotechnol Prog. 25: 594-603.

Di Giovanni S, et al. (2005) Cell cycle inhibition provides neuroprotection and reduces glial proliferation and scar formation after traumatic brain injury. Proc Natl Acad Sci U SA. 102: 8333-8338.

Dimitrova DS and Gilbert DM. (2000) Temporally coordinated assembly and disassembly of replication factories in the absence of DNA synthesis. Nat Cell Biol. 2: 686-694.

Djouhri L and Lawson SN. (1999) Changes in somatic action potential shape in guinea-pig nociceptive primary afferent neurones during inflammation in vivo. J Physiol. 520 Pt 2: 565-576.

Dolcet X, et al. (2001) Cytokines promote motoneuron survival through the Janus kinase-dependent activation of the phosphatidylinositol 3-kinase pathway. Mol Cell Neurosci. 18: 619-631.

Du Y, et al. (2006) Distinct effects of p75 in mediating actions of neurotrophins on basal forebrain oligodendrocytes. Mol Cell Neurosci. 31.: 366-375.

Dulcey CS, et al. (1991) Deep UV photochemistry of chemisorbed monolayers: patterned coplanar molecular assemblies. Science. 252: 551-554.

(56) References Cited

OTHER PUBLICATIONS

Dumont RJ, et al. (2001) Acute spinal cord injury, part I: pathophysiologic mechanisms. Clin Neuropharmacolo12:v. 24: 254-264.
Duport S, et al. (1999) A metallic multisite recording system designed for continuous long-term monitoring of electrophysiological activity in slice cultures. Biosens Bioelectron. 14: 369-376.
Dusterhoft S, et al. (1999) Evidence that acidic fibroblast growth factor promotes maturation of rat satellite-cell-derived myotubes in vitro. Differentiation. 65: 161-169.
Dutton EK, et al. (1995) Acetylcholine receptor aggregation at nerve-muscle contacts in mammalian cultures: induction by ventral spinal cord neurons is specific to axons. JNeurosci. 15: 7401-7416.
Edwards D, et al. (2010) Addition of glutamate to serum-free culture promotes recovery of electrical activity in adult hippocampal neurons in vitro. J Neurosci Methods. 190: 155-163.
Egert U, et al. (1998) A novel organotypic long-term culture of the rat hippocampus on substrate-integrated multielectrode arrays. Brain Res Brain Res Protoc. 2: 229-242.
Egert U, et al. (2006) Analysis of cardiac myocyte activity dynamics with microeletrode arrays. In: Taketani M BM, editor. Advances m netwrok electrophysiology using multi electrode arrays: Springer 2006. p. 274-290.
Eisen A and Swash M. (2001) Clinical neurophysiology of ALS. Clin Neurophysiol. 112: 2190-2201.
Eisenberg T, et al. (2009) Induction of autophagy by spermidine promotes longevity. Nat Cell Biol. 11: 1305-1314.
Eldridge CF, et al. (1989) Differentiation of axon-related Schwann cells in vitro: II. Control of myelin formation by basal lamina. J Neurosci. 9: 625-638.
Elia D, et al. (2007) Sonic hedgehog promotes proliferation and differentiation of adult muscle cells: Involvement of MAPK/ERK and PI3K/Akt pathways. Biochim Biophys Acta. 1773: 1438-1446.
Emery AEH. (2002) The muscular dystrophies. Lancet. 359: 687-695.
Engler AJ, et al. (2006) Matrix elasticity directs stem cell lineage specification. Cell. 126: 677-689.
English AW. (2003) Cytokines, growth factors and sprouting at the neuromuscular junction. J Neurocytol. 32: 943-960.
Entcheva EK, et al. (2004) Fluorescence imaging of electrical activity in cardiac cells using an all-solid-state system. IEEE Trans Biomed Eng. 51: 331-341.
Ericson J, et al. (1992) Early stages of motor neuron differentiation revealed by expression ofhomeobox gene Islet-I. Science. 256: 1555-1560.
Esch MB, et al. (2011) The role of body-on-a-chip devices in drug and toxicity studies. Annu Rev Biomed Eng. 13: 55-72.
Esch MB, et al. (2012) On chip porous polymer membranes for integration of gastrointestinal tract epithelium with microfluidic 'body-on-a-chip' devices. Biomed Microdevices. 14: 895-906.
Eschenhagen T and Zimmermann WH. (2005) Engineering myocardial tissue. Circ Res. 97: 1220-1231.
Evans MS, et al. (1998) Electrophysiology of embryonic, adult and aged rat hippocampal neurons in serum-free culture. J Neurosci Methods. 79: 37-46.
Fan CM, et al. (1994) Patterning of mammalian somites by surface ectoderm and notochord: evidence for sclerotome induction by a hedgehog homolog. Cell. 79: 1175-1186.
Faraut B, et al. (2004) Thrombin reduces MuSK and acetylcholine receptor expression along with neuromuscular contact size in vitro. Eur J Neurosci. 19: 2099-2108.
FDA (2004) Innovation or Stagnation: Challenge and Opportunity on the Critical Path to New Medical Products.
Fernandez-Valle C, et al. (1993) Expression of the protein zero myelin gene in axon-related Schwann cells is linked to basal lamina formation. Development. 119: 867-880.
Fernandez-Valle C, et al. (1995) Schwann cells degrade myelin and proliferate in the absence of macrophages: evidence from in vitro studies of Wallerian degeneration. J Neurocytol. 24: 667-679.

Fields GB, et al. (1998) Protein-like molecular architecture: biomaterial applications for inducing cellular receptor binding and signal transduction. Biopolymers. 47: 143-151.
Fields GB. (1999) Induction of protein-like molecular architecture by selfassembly processes. Bioorg Med Chem. 7: 75-81.
Figenschou A, et al. (1996) Cholinergic modulation of the action potential in rat hippocampal neurons. Eur J Neurosci. 8: 211-219.
Fink CC, et al. (1999) Determination of time-dependent inositol-1,4,5-trisphosphate concentrations during calcium release in a smooth muscle cell. Biophys J. 77: 617-628.
Fischbach GD and Cohen SA. (1973) The distribution of acetylcholine sensitivity over uninnervated and innervated muscle fibers grown in cell culture. Dev Biol. 31: 147-162.
Fischbach GD. (1972) Synapse formation between dissociated nerve and muscle cells in low density cell cultures. Dev Biol. 28: 407-429.
Fisher OZ, et al. (2010) Bioinspired materials for controlling stem cell fate. Ace Chem Res. 43: 419-428.
Fishman RA. (2002) The cerebrospinal fluid production rate is reduced in dementia of the Alzheimer's type. Neurology. 58: 1866; author reply 1866.
Flucher BE, et al. (1990) Localization of the alpha 1 and alpha 2 subunits of the dihydropyridine receptor and ankyrin in skeletal muscle triads. Neuron. 5: 339-351.
Flucher BE, et al. (1991) Biogenesis of transverse tubules in skeletal muscle in vitro. Dev Biol. 145: 77-90.
Flucher BE, et al. (1992) Coordinated development of myofibrils, sarcoplasmic reticulum and transverse tubules in normal and dysgenic mouse skeletal muscle, in vivo and in vitro. Dev Biol. 150: 266-280.
Flucher BE, et al. (1994) Molecular organization of transverse tubule/sarcoplasmic reticulum junctions during development of excitation-contraction coupling in skeletal muscle. Mol Biol Cell. 5: 1105-1118.
Forry SP, et al. (2006) Facilitating the culture of mammalian nerve cells with polyelectrolyte multilayers. Langmuir. 22: 5770-5775.
Foster RF, et al. (1987) A laminin substrate promotes myogenesis in rat skeletal muscle cultures: analysis of replication and development using antidesmin and anti-BrdUrd monoclonal antibodies. Dev Biol. 122: 11-20.
Fowler VM, et al. (1993) Tropomodulin is associated with the free (pointed) ends of the thin filaments in rat skeletal muscle. J Cell Biol. 120: 411-420.
Fox MA, et al. (2007) Distinct target-derived signals orgamze formation, maturation, and maintenance of motor nerve terminals. Cell. 129: 179-193.
Francis PT. (2008) Glutamatergic approaches to the treatment of cognitive and behavioural symptoms of Alzheimer's disease. Neurodegener Dis. 5: 241-243.
Frank E and Fischbach GD. (1979) Early events in neuromuscular junction formation in vitro: induction of acetylcholine receptor clusters in the postsynaptic membrane and morphology of newly formed synapses. J Cell Biol. 83: 143-158.
Franzini-Armstrong C, et al. (1997) Ryanodine receptors of striated muscles: a complex channel capable of multiple interactions. Physiol Rev. 77: 699-729.
Friedman B, et al. (1995) BDNF and NT-4/5 exert neurotrophic influences on injured adult spinal motor neurons. J Neurosci. 15: 1044-1056.
Fu X, et al. (1995) Acidic fibroblast growth factor reduces rat skeletal muscle damage caused by ischemia and reperfusion. Chin Med J (Engl). 108: 209-214.
Fuentes-Medel Y, et al. (2012) Integration of a retrograde signal during synapse formation by glia-secreted TGF-B ligand. Curr Biol. 22: 1831-1838.
Funakoshi H, et al. (1995) Muscle-derived neurotrophin-4 as an activitydependent trophic signal for adult motor neurons. Science. 268: 1495-1499.
Gajsek N, et al. (2006) Expression of MuSK in in vitro-innervated human muscle. J Mol Neurosci. 30: 27-28.
Gajsek N, et al. (2008) Synaptogenetic mechanisms controlling postsynaptic differentiation of the neuromuscular junction are nerve-dependent in human and nerve-independent in mouse C2C12 muscle cultures. Chem Biol Interact. 175:50-57.

(56) References Cited

OTHER PUBLICATIONS

Galizia CG and Menzel R. (2000) Probing the olfactory code. Nat Neurosci. 3: 853-854.
Gao BX and Ziskind-Conhaim L. (1995) Development of glycine- and GABAgated currents in rat spinal motoneurons. J Neurophysiol. 74: 113-121.
Gao Bx and Ziskind-Conhaim L. (1998) Development of ionic currents underlying changes in action potential waveforms in rat spinal motoneurons. J Neurophysiol. 80: 3047-3061.
Gao J, et al. (2005) Human neural stem cell-derived cholinergic neurons innervate muscle in motoneuron deficient adult rats. Neuroscience. 131: 257-262.
Garcez RC, et al. (2009) Epidermal growth factor (EGF) promotes the in vitro differentiation of neural crest cells to neurons and melanocytes. Cell Mol Neurobiol. 29: 1087-1091.
Garell PC, et al. (1998) Introductory overview of research instruments for recording the electrical activity of neurons in the human brain. Rev Sci Instrum. 69:4027-4037.
Gaud A, et al. (2004) Prednisone reduces muscle degeneration in dystrophindeficient Caenorhabditis elegans. Neuromuscul Disord. 14: 365-370.
Georger JH, et al. (1992) Coplanar patterns of self-assembled monolayers for selective cell adhesion and outgrowth. Thin Solid Films. 210: 716-719.
Germani A, et al. (2003) Vascular endothelial growth factor modulates skeletal myoblast function. Am J Pathol. 163: 1417-1428.
Gerrard L, et al. (2005) Differentiation of human embryonic stem cells to neural lineages in adherent culture by blocking bone morphogenetic protein signaling. Stem Cells. 23: 1234-1241.
Ghiani CA, et al. (1999) Neurotransmitter receptor activation triggers p27(Kipl) and p21(CIP 1) accumulation and G 1 cell cycle arrest in oligodendrocyte progenitors. Development. 126: 1077-1090.
Ginsberg SD. (2005) Glutamatergic neurotransmission expression profiling in the mouse hippocampus after perforant-path transection. Am J Geriatr Psychiatry, 13: 1052-1061.
Glass L. (1975) Classification of biological networks by their qualitative dynamics. J Theor Biol. 54: 85-107.
Glass Land Kauffman SA. (1973) The logical analysis of continuous, non-linear biochemical control networks. J Theor Biol. 39: 103-129.
Glass, D. J. (2003). Signalling pathways that mediate skeletal muscle hypertrophy and atrophy. Nat Cell Biol. 5: 87-90.
Golan H, et al. (2000) GABA withdrawal modifies network activity in cultured hippocampal neurons. Neural Plast. 7: 31-42.
Gold MR. (1982) The effects of vasoactive intestinal peptide on neuromuscular transmission in the frog. J Physiol. 327: 325-335.
Golden JP, et al. (1999) Expression of neurturin, GDNF, and GDNF family-receptor mRNA in the developing and mature mouse. Exp Neurol. 158: 504-528.
Gonzalez AM, et al. (1990) Distribution of basic fibroblast growth factor in the 18-day rat fetus: localization in the basement membranes of diverse tissues. J Cell Biol. 110: 753-765.
Goodyear S and Sharma MC. (2007) Roscovitine regulates invasive breast cancer cell (MDA-MB231) proliferation and survival through cell cycle regulatory protein cdk5. Exp Mol Pathol. 82: 25-32.
Goodyear S. (2005) Roscovitine induced cell death is mediated through specific inhibition of cell cycle regulatory protein cdk5. AACR Meeting Abstracts. 1045-d-1046.
Gordon AM, et al. (2000) Regulation of Contraction in Striated Muscle. Physiol Rev. 80: 853-924.
Goritz C, et al. (2005) Multiple mechanisms mediate cholesterol-induced synaptogenesis in a CNS neuron. Mol Cell Neurosci. 29: 190-201.
Gozes I, et al. (2004) NAP mechanisms of neuroprotection. J Mol Neurosci. 24: 67-72.
Graham SC, et al. (1992) Enzyme and size profiles in chronically inactive cat soleus muscle fibers. Muscle Nerve 15: 27-36.
Gramowski A, et al. (2006) Functional screening of traditional antidepressants with primary cortical neuronal networks grown on multielectrode neurochips. Eur J Neurosci. 24: 455-465.
Granchelli JA, et al. (2000) Pre-clinical screening of drugs using the mdx mouse. Neuromuscul Disord. 10: 235-239.
Greaves P, et al. (2004) First dose of potential new medicines to humans: how animals help. Nat Rev Drug Discov. 3: 226-236.
Greenstein JL and Winslow RL. (2002) An integrative model of the cardiac ventricular myocyte incorporating local control of Ca2+ release. Biophys J. 83:2918-2945.
Greenwood AL, et al. (1999) Identification of dividing, determined sensory neuron precursors in the mammalian neural crest. Development. 126: 3545-3559.
Gross GW, et al. (1993) Stimulation of monolayer networks in culture through thin-film indium-tin oxide recording electrodes. J Neurosci Methods. 50: 131-143.
Gross GW, et al. (1995) The Use of Neuronal Networks on Multielectrode Arrays as Biosensors. Biosens Bioelectron. 10: 553-567.
Gross GW, et al. (1997) Odor, drug and toxin analysis with neuronal networks in vitro: extracellular array recording of network responses. Biosens Bioelectron. 12: 373-393.
Groves MJ and Scaravelli F. (2005) Chapter 31—Pathology of Peripheral Neuron Cell Bodies. In: Dyck, PJ and Thomas, PK, (eds.) Peripheral neuropathy. 683-732. Elsevier Saunders: Philadelphia.
Grubic Z, et al. (1995) Myoblast fusion and innervation with rat motor nerve alter distribution of acetylcholinesterase and its mRNA in cultures of human muscle. Neuron. 14: 317-327.
Guenou H, et al. (2009) Human embryonic stem-cell derivatives for full reconstruction of the pluristratified epidermis: a preclinical study. Lancet. 374:1745-175.
Guettier-Sigrist S, et al. (1998) Muscle could be the therapeutic target in SMA treatment. J Neurosci Res. 53: 663-669.
Guettier-Sigrist S, et al. (2000) Cell types required to efficiently innervate human muscle cells in vitro. Exp Cell Res. 259: 204-212.
Gullberg D, et al. (1995) Analysis of fibronectin and vitronectin receptors on human fetal skeletal muscle cells upon differentiation. Exp Cell Res. 220: 112-123.
Guo JZ, et al. (2005) Synaptically released and exogenous ACh activates different nicotinic receptors to enhance evoked glutamatergic transmission in the lateral geniculate nucleus. J Neurophysiol. 94: 2549-2560.
Guo X, et al. (2011) Neuromuscular junction formation between human stem cell-derived motoneurons and human skeletal muscle in a defined system. Biomaterials. 32: 9602-9611.
Guo X, et al. (2012) Tissue engineering the monosynaptic circuit of the stretch reflex arc with co-culture of embryonic motoneurons and proprioceptive sensory neurons. Biomaterials. 33: 5723-5731.
Guo X, et al. (2013) Derivation of sensory neurons and neural crest stem cells from human neural progenitor hNPI. Biomaterials. 34: 4418-4427.
Guo XF, et al. (2010a) Characterization of a human fetal spinal cord stem cell line, NSI-566RSC, and its induction to functional motoneurons. J Tissue Eng Regen Med. 4: 181-193.
Guo XF, et al. (2010b) Neuromuscular junction formation between human stem-cell-derived motoneurons and rat skeletal muscle in a defined system. Tissue Eng Part C Methods. 16: 1347-1355.
Gupta S, et al. (2007) Boolean network analysis of a neurotransmitter signaling pathway. J Theor Biol. 244: 463-469.
Gureviciene I, et al. (2004) Normal induction but accelerated decay of LTP in APP+ PSI transgenic mice. Neurobiol Dis. 15: 188-195.
Haas HL and Selbach O. (2000) Functions of neuronal adenosine receptors. Naunyn Schmiedebergs Arch Pharmacol. 362: 375-381.
Halbach M, et al. (2003) Estimation of action potential changes from field potential recordings in multicellular mouse cardiac myocyte cultures. Cell Physiol Biochem. 13: 271-284.
Hall BK, et al. (2000) All for one and one for all: condensations and the initiation of skeletal development. Bioessays. 22: 138-147.
Hamaguchi T, et al. (2006) Anti-amyloidogenic therapies: strategies for prevention and treatment of Alzheimer's disease. Cell Mol Life Sci. 63: 1538-1552.
Hammarback JA, et al. (1985) Guidance of neurite outgrowth by pathways of substratum-adsorbed laminin. J Neurosci Res. 13: 213-220.

(56) References Cited

OTHER PUBLICATIONS

Han DK and Hubbell JA. (1997) Synthesis of Polymer Network Scaffolds from 1-Lactide and Poly(ethylene glycol) and Their Interaction with Cells. Macromolecules. 30: 607—6083.

Hantai D, et al. (1991) Developmental appearance of thrombospondin in neonatal mouse skeletal muscle. Eur J Cell Biol. 55: 286-294.

Harding SE, et al. (2007) The human embryonic stem cell-derived cardiomyocyte as a pharmacological model. Pharmacol Ther. 113: 341-353.

Hardy J and Selkoe DJ. (2002) The amyloid hypothesis of Alzheimer's disease: progress and problems on the road to therapeutics. Science. 297: 353-356.

Hari L, et al. (2002) Lineage-specific requirements of beta-catenin in neural crest development. J Cell Biol. 159: 867-880.

Harms H, et al. (2006) Whole-cell living biosensors—are they ready for environmental application? Appl Microbiol Biotechnol. 70: 273-280.

Harper JM, et al. (2004) Axonal growth of embryonic stem cell-derived motoneurons in vitro and in motoneuron-injured adult rats. Proc Natl Acad Sci U s A. 101: 7123-7128.

Harsch A, et al. (1997) Strychnine analysis with neuronal networks in vitro: extracellular array recording of network responses. Biosens Bioelectron. 12: 827-835.

Heiduschka P and Thanos S. (1998) Implantable bioelectric interfaces for lost nerve functions. Prog Neurobiol. 55: 433-461.

Heinrich G. (2003) A novel BDNF gene promoter directs expression to skeletal muscle. BMC Neurosci. 4: 11.

Henderson CE, et al. (1993) Neurotrophins promote motor neuron survival and are present in embryonic limb bud. Nature. 363: 266-270.

Henderson CE, et al. (1994) GNF: a potent survival factor for motoneurons present in peripheral nerve and muscle. Science. 266: 1062-1064.

Hennessey JV, et al. (1997) Increase in percutaneous muscle biopsy yield with a suction-enhancement technique. J Appl Physiol. 82: 1739-1742.

Hennessey N, et al. (2001) Growth hormone administration and exercise effects on muscle fiber type and diameter in moderately frail older people. J Am Geriatr Soc. 49: 852-858.

Hermann M, et al. (2006) Exposure of atorvastatin is unchanged but lactone and acid metabolites are increased several-fold in patients withatorvastatin-induced myopathy. Clin Pharmacol Ther. 79: 532-539.

Herrup K and Yang Y. (2007) Cell cycle regulation in the postmitotic neuron: oxymoron or new biology? Nat Rev Neurosci. 8: 368-378.

Hickman J, et al. (1993) The use of monlayers as templates for biocompatibility studies. Abstracts of Papers of the American Chemical Society. 205: 146-Coll.

Hickman J. (2005) Building Minimalistic Hybrid Neuroelectric Devices in Toward Replacement Parts for the Brain: Implantable Biomimetic Electronics as Neural Prosthetic (T.W. Berger and D.L. Glanzman Eds.), 1st edition. Cambridge, MA: MIT Press.

Hickman JJ, et al. (1994) Rational Pattern Design for in-Vitro Cellular Networks Using Surface Photochemistry. J Vac Science Technol A. 12: 607-616.

Hirano A. (1968) A confirmation of the oligodendroglial origin of myelin in the adult rat. J Cell Biol. 38: 637-640.

Hjerling-Leffler J, et al. (2005) The boundary cap: a source of neural crest stem cells that generate multiple sensory neuron subtypes. Development. 132: 2623-2632.

Hoffman EP and Escolar D. (2006) Translating mighty mice into neuromuscular therapeutics: is bigger muscle better? Am J Pathol. 168: 177 5-1778.

Hoffmann F and Bading H. (2006) Long term recordings with microelectrode arrays: studies of transcription-dependent neuronal plasticity and axonal regeneration. J Physiol Paris. 99: 125-132.

Holleran AL, et al. (1995) Glutamine metabolism in AS-30D hepatoma cells. Evidence for its conversion into lipids via reductive carboxylation. Mol Cell Biochem. 152: 95-101.

Hondeghem LM and Hoffinan P. (2003b) Blinded test in isolated female rabbit heart reliably identifies action potential duration prolongation and proarrhythmic drugs: importance of triangulation, reverse use dependence, and instability. J Cardiovasc Pharmacol. 41: 14-24.

Hondeghem LM, et al. (2001) Instability and triangulation of the action potential predict serious proarrhythmia, but action potential duration prolongation is antiarrhythmic. Circulation. 103: 2004-2013.

Hondeghem LM, et al. (2003a) Detection of proarrhythmia in the female rabbit heart: blinded validation. J Cardiovasc Electrophysiol. 14: 287-29.

Hondeghem LM. (2006) Thorough QT/QTc not so thorough: removes torsadogenic predictors from the T-wave, incriminates safe drugs, and misses profibrillatory drugs. J Cardiovasc Electrophysiol. 17: 337-340.

Hondeghem LM. (2007) Relative contributions of TRiaD and QT to proarrhythmia. J Cardiovasc Electrophysiol. 18: 655-657.

Hsiao CF, et al. (2005) Voltage-dependent calcium currents in trigeminal motoneurons of early postnatal rats: modulation by 5-HT receptors. J Neurophysiol. 94: 2063-2072.

Hu BY, et al. (2009) Human oligodendrocytes from embryonic stem cells: conserved SHH signaling networks and divergent FGF effects. Development. 136: 1443-1452.

Hua JY and Smth SJ. (2004) Neural activity and the dynamics of central nervous system development. Nat Neurosci. 7: 327-332.

Huang Y, et al. (2007) An alphaIA-adrenergic-extracellular signal-regulated kinase survival signaling pathway in cardiac myocytes. Circulation. 115: 763-772.

Huang YC, et al. (2005) Rapid formation of functional muscle in vitro using fibrin gels. J Appl Physiol. 98: 706-713.

Hucka M, et al. (2003) The systems biology markup language (SBML): a medium for representation and exchange of biochemical network models. Bioinformatics. 19: 524-531.

Hughes B. (2008) 2007 FDA drug approvals: a year of flux. Nat Rev Drug Discov. 7: 107-109.

Huh D, et al. (2010) Reconstituting organ-level lung functions on a chip. Science. 328: 1662-1668.

Huh D, et al. (2012) Microengineered physiological biomimicry: organs-onchips. Lab Chip. 12: 2156-2164.

Hui EE and Bhatia SN. (2007) Microscale control of cell contact and spacing via three-component surface patterning. Langmuir. 23: 4103-4107.

Hung SC, et al. (2002) In vitro differentiation of size-sieved stem cells into electrically active neural cells. Stem Cells. 20: 522-529.

Husmann I, et al. (1996) Growth factors in skeletal muscle regeneration. Cytokine Growth Factor Rev. 7: 249-258.

Huxley, A. F. (1975). The origin of force in skeletal muscle. Ciba Found Symp. 31: 271-290.

Ichikawa H, et al. (2004) Effect of Bm-3a deficiency on parvalbumin-immunoreactive primary sensory neurons in the dorsal root ganglion. Brain Res Dev Brain Res. 150: 41-45.

Inoue N, et al. (2004) Rapid electrical stimulation of contraction modulates gap junction protein m neonatal rat cultured cardiomyocytes: involvement of mitogen-activated protein kinases and effects of angiotensin II-receptor antagonist. J Am Coll Cardiol. 44: 914-922.

Iravanian S, et al. (2003) Functional reentry in cultured monolayers of neonatal rat cardiac cells. Am J Physiol Heart Circ Physiol. 285: H449-H456.

Ito Y. (1999) Surface micropatterning to regulate cell functions. Biomaterials. 20:2333-2342.

Izrael M, et al. (2007) Human oligodendrocytes derived from embryonic stem cells: Effect of noggin on phenotypic differentiation in vitro and on myelination in vivo. Mol Cell Neurosci. 34: 310-323.

Izumiya Y, et al. (2008) Fast/glycolytic muscle fiber growth reduces fat mass and improves metabolic parameters in obese mice. Cell Metabolism. 7: 159-172.

Jackson JH 4th, et al. (2004) Assessment of drug therapy management and the prevalence of heart failure in a managed care population with hypertension. J Manag Care Pharm. 10: 513-520.

Jaworska-Wilczynska M, et al. (2002) Three lipoprotein receptors and cholesterol in inclusion-body myositis muscle. Neurology. 58: 438-445.

(56) References Cited

OTHER PUBLICATIONS

Jensen J, et al. (2009) Human embryonic stem cell technologies and drug discovery. J Cell Physiol. 219: 513-519.
Jessen KR and Mirsky R. (2005) The origin and development of glial cells in peripheral nerves. Nat Rev Neurosci. 6: 671-682.
Jevsek M, et al. (2004) Origin of acetylcholinesterase in the neuromuscular junction formed in the in vitro innervated human muscle. Eur J Neurosci. 20:2865-2871.
Jhamandas JH, et al. (2001) Cellular mechanisms for amyloid beta-protein activation of rat cholinergic basal forebrain neurons. J Neurophysiol. 86: 1312-1320.
Jiang XH, et al. (2009) Isolation and characterization of neural crest stem cells derived from in vitro-differentiated human embryonic stem cells. Stem Cells Dev. 18: 1059-1070.
Jiang Z and Clemens PR. (2006) Cellular caspase-8-like inhibitory protein (cFLIP) prevents inhibition of muscle cell differentiation induced by cancer cells. FASEB J. 20: 2570-2572.
Jiang ZG, et al. (1990) Excitatory and inhibitory transmission from dorsal root afferents to neonate rat motoneurons in vitro. Brain Res. 535: 110-118.
Jin P, et al. (1991) Recombinant platelet-derived growth factor-BB stimulates 80. growth and inhibits differentiation of rat L6 myoblasts. J Biol Chem. 266: 1245-1249.
Johnson TE, et al. (2005) Statins and PP ARalpha agonists induce myotoxicity in differentiated rat skeletal muscle cultures but do not exhibit synergy with cotreatment. Toxicol Appl Pharmacol. 208: 210-221.
Julius D and Basbaum AI. (2001) Molecular mechanisms of nociception. Nature. 413: 203-210.
Jung DR, et al. (1998) Cell-Based Sensor Microelectrode Array Characterized by Imaging X-ray Photoelectron Spectroscopy, Scanning Electron Microscopy, Impedance Measurements, and Extracellular Recordings. Journal of Vacuum Science & Technology A (Vacuum, Surfaces, and Films). 16: 1183-1188.
Jung DR, et al. (2001) Topographical and physicochemical modification of material surface to enable patterning of living cells. Crit Rev Biotechnol. 21: 111-154.
Jurdana M, et al. (2009) Neural agrin changes the electrical properties of developing human skeletal muscle cells. Cell Mol Neurobiol. 29: 123-131.
Kaeberlein M. (2009) Spermidine surprise for a long life. Nat Cell Biol. 11:1277-1278.
Kaji H, et al. (2003) Pharmacological characterization of micropatterned cardiac myocytes. Biomaterials. 24: 4239-4244.
Kamp TJ. (2009) Human pluripotent stem cell-derived cardiomyocytes for safety pharmacology applications. Journal of Pharmacological and Toxicological Methods. 60: 259.
Kane RS, et al. (1999) Patterning proteins and cells using soft lithography. Biomaterials. 20: 2363-2376.
Kang JH, et al. (2009) In vitro 3D model for human vascularized adipose tissue. Tissue Eng Part A. 15: 2227-2236.
Kato AC and Lindsay RM. (1994) Overlapping and additive effects of neurotrophins and CNTF on cultured human spinal cord neurons. Exp Neurol. 130: 196-20.
Katsuki H, et al. (2000) Distinct signaling pathways involved in multiple effects of basic fibroblast growth factor on cultured rat hippocampal neurons. Brain Res. 885: 240-250.
Katz LC and Shatz CJ. (1996) Synaptic activity and the construction of cortical circuits. 274: 1133-1138.
Kauffman S, et al. (2003) Random Boolean network models and the yeast transcriptional network. Proc Natl Acad Sci US A. 100: 14796-14799.
Kauffman S. (1971) Gene regulation networks: a theory for their global structure and behaviors. Curr Top Dev Biol. 6: 145-182.
Kaufmann P, et al. (2006) Toxicity of statins on rat skeletal muscle mitochondria. Cell Mol Life Sci. 63: 2415-2425.
Keefer EW, et al. (2001) Acute toxicity screening of novel AChE inhibitors using neuronal networks on microelectrode arrays. Neurotoxicology. 22: 3-1.
Keefer EW, et al. (2001) Characterization of acute neurotoxic effects of trimethylolpropane phosphate via neuronal network biosensors. Biosens Bioelectron. 16: 513-525.
Kessaris N, et al. (2008) Specification of CNS glia from neural stem cells in the embryonic neuroepithelium. Philos Trans R Soc Lond B Biol Sci. 363: 71-85.
Khademhosseini A, et al. (2006a) Interplay of biomaterials and micro-scale technologies for advancing biomedical applications. J Biomater Sci Polym Ed. 17: 1221-1240.
Khademhosseini A, et al. (2006b) Microscale technologies for tissue engineering and biology. Proc Natl Acad Sci USA. 103: 2480-2487.
Khorchid A, et al. (1999) Characterization of the signal transduction pathways mediating noradrenaline-stimulated MAPK activation and c-fos expression in oligodendrocyte progenitors. JNeurosci Res. 58: 765-778.
Khorchid A, et al. (2002) Developmental regulation of alpha IA-adrenoceptor function in rat brain oligodendrocyte cultures. Neuropharmacology. 42: 685-696.
Kidambi S, et al. (2004) Controlling primary hepatocyte adhesion and spreading on protein-free polyelectrolyte multilayer films. J Am Chem Soc. 126: 16286-16287.
Kidambi S, et al. (2007a) Patterned co-culture of primary hepatocytes and fibroblasts using polyelectrolyte multilayer templates. Macromol Biosci. 7: 344-353.
Kidambi S, et al. (2007b) Cell adhesion on polyelectrolyte multilayer coated polydimethylsiloxane surfaces with varying topographies. Tissue Eng. 13: 2105-2117.
Kidd, J. (2006). Life after statin patent expires. Nat Rev Drug Discov. 5: 813-814.
Kim C, et al. (2010) Non-cardiomyocytes influence the electrophysiological maturation of human embryonic stem cell-derived cardiomyocytes during differentiation. Stem Cells Dev. 19: 783-795.
Kim J, et al. (2002) Dopamine neurons derived from embryonic stem cells function in an animal model of Parkinson's disease. Nature. 418: 50-56.
Kim K, et al. (2011) Calibrated micropost arrays for biomechanical characterization of cardiomyocytes. Micro and Nano Letters. 6: 317-322.
Kim SU, et al. (2002) Production of immortalized human neural crest stem cells. Methods Mol Biol. 198: 55-65.
King T, et al. (2000) Piezoactuators for 'real-world' applications—Can they deliver sufficient displacement? Power Engineering. 14: 105-110.
Kingshott P and Griesser HJ. (1999) Surfaces that resist bioadhesion. Current Opinion in Solid State and Materials Science. 4: 403-412.
Kirazov E, et al. (2008) Amyloid beta peptides exhibit functional neurotoxicity to cortical network cultures. Compt Rend Acad Bulg Sci. 61: 905-910.
Kita-Matsuo H, et al. (2009) Lentiviral vectors and protocols for creation of stable hESC lines for fluorescent tracking and drug resistance selection of cardiomyocytes. PLoS One. 4: e5046.
Kleber AG and Rudy Y. (2004) Basic mechanisms of cardiac impulse propagation and associated arrhythmias. Physiol Rev. 84: 431-488.
Klein C, et al. (2002) Zinc inhibition of cAMP signaling. J Biol Chem. 277: 11859-11865.
Klein WL. (2002) Abeta toxicity in Alzheimer's disease: globular oligomers (ADDLs) as new vaccine and drug targets. Neurochem Int. 41: 345-352.
Kleinfeld D, et al. (1988) Controlled outgrowth of dissociated neurons on patterned substrates. J Neurosci. 8: 4098-4120.
Knobloch M and Mansuy IM. (2008) Dendritic spine loss and synaptic alterations in Alzheimer's disease. Mol Neurobiol. 37: 73-82.
Kobayashi T, et al. (1985) Acetylcholine receptors and acetylcholinesterase accumulate at the nerve-muscle contacts of de novo grown human monolayer muscle cocultured with fetal rat spinal cord. Exp Neurol. 88: 327-335.

(56) References Cited

OTHER PUBLICATIONS

Kobayashi T, et al. (1987) Human muscle cultured in monolayer and cocultured with fetal rat spinal cord: importance of dorsal root ganglia for achieving successful functional innervation. JNeurosci. 7: 3131-3141.
Koike T, et al. (2008) Axon & dendrite degeneration: its mechanisms and protective experimental paradigms. Neurochem Int. 52: 751-760.
Koirala S, et al. (2003) Roles of glial cells in the formation, function, and maintenance of the neuromuscular junction. J Neurocytol. 32: 987-1002.
Koleva M, et al. (2005) Pleiotropic effects of sonic hedgehog on muscle satellite cells. Cell Mol Life Sci. 62: 1863-1870.
Koliatsos VE, et al. (2008) Human stem cell grafts as therapies for motor neuron disease. Expert Opin Biol Ther. 8: 137-141.
Kontrogianni-Konstantopoulos A, et al. (2009) Muscle giants: molecular scaffolds in sarcomerogenesis. Physiol Rev. 89: 1217-1267.
Kornblum HI, et al. (1999) Multiple trophic actions of heparin-binding epidermal A511. growth factor (HB-EGF) in the central nervous system. Eur J Neurosci. 11: 3236-3246.
Kucera J and Dorovini-Zis K. (1979). Types of human intrafusal muscle fibers. Muscle Nerve. 2: 437-451.
Kucera J, et al. (1989) Role of nerve and muscle factors in the development of rat muscle spindles. Am J Anat. 186: 144-160.
Kucera J, et al. (1992) Axotomy induces fusimotor-free muscle spindles in neonatal rats. Neurosci Lett. 136: 216-218.
Kucera J. (1982a) One-bag-fiber muscle spindles in tenuissimus muscles of the cat. Histochemistry and Cell Biology. 76: 315-328.
Kucera, J. (1982b). The topography of long nuclear chain intrafusal fibers in the cat muscle spindle. Histochemistry. 74: 183-197.
Kucera, J. (1983). Multiple-bag-fiber muscle spindles in tenuissimus muscles of the cat. Histochemistry. 79: 457-476.
Kudla AJ, et al. (1995) A requirement for fibroblast growth factor in regulation of skeletal muscle growth and differentiation cannot be replaced by activation of platelet-derived growth factor signaling pathways. Mol Cell Biol. 15: 3238-3246.
Kuhl U, et al. (1982) Synthesis of type IV collagen and laminin in cultures of skeletal muscle cells and their assembly on the surface of myotubes. Dev Biol. 93: 344-354.
Kuhl U, et al. (1986) Role of laminin and fibronectin in selecting myogenic versus fibrogenic cells from skeletal muscle cells in vitro. Dev Biol. 117: 628-635.
Kumar S, et al. (1998) NT-3-mediated TrkC receptor activation promotes proliferation and cell survival of rodent progenitor oligodendrocyte cells in vitro and in vivo. J Neurosci Res. 54: 754-765.
Kurek JB, et al. (1996) Leukemia inhibitory factor and interleukin-6 are produced by diseased and regenerating skeletal muscle. Muscle Nerve. 19: 1291-1301.
Lacor PN, et al. (2007) Abeta oligomer-induced aberrations m synapse composition, shape, and density provide a molecular basis for loss of connectivity in Alzheimer's disease. J Neurosci. 27: 796-807.
Lacor PN. (2007) Advances on the understanding of the origins of synaptic pathology in Ad. Curr Genomics. 8: 486-508.
Laflamme MA, et al. (2007) Cardiomyocytes derived from human embryonic stem cells in pro-survival factors enhance function of infarcted rat hearts. Nat Biotechnol. 25: 1015-1024.
Lamb TM, et al. (1993) Neural induction by the secreted polypeptide noggin. Science. 262: 713-718.
Lambert MP, et al. (1998) Diffusible, nonfibrillar ligands derived from Abeta1-42 are potent central nervous system neurotoxins. Proc Natl Acad Sci US A. 95:6448-6453.
Lambeth MJ and Kushmerick MJ. (2002) A computational model for glycogenolvsis in skeletal muscle. Ann Biomed Eng. 30: 808-827.
Lambrechts D, et al. (2003) VEGF is a modifier of amyotrophic lateral sclerosis in mice and humans and protects motoneurons against ischemic death. Nat Genet. 34: 383-394.

Langen RC, et al. (2003) Enhanced myogenic differentiation by extracellular matrix is regulated at the early stages of myogenesis. In Vitro Cell Dev Biol Anim. 39: 163-169.
Langer R and Vacanti JP. (1993) Tissue engineering. Science. 260: 920-926.
Larkin LM, et al. (2006) Functional evaluation of nerve-skeletal muscle constructs engineered in vitro. In Vitro Cell Dev Biol Anim. 42: 75-82.
Larsson L and Ansved T. (1995) Effects of ageing on the motor unit. Prog Neurobiol. 45: 397-415.
Lasser KE, et al. (2002) Timing of new black box warnings and withdrawals for prescription medications. JAMA. 287: 2215-2220.
Lawrence CL, et al. (2005) Nonclinical proarrhythmia models: predicting Torsades de Pointes. J Pharmacol Toxicol Methods. 52: 46-59.
Lawrence CL, et al. (2006) A rabbit Langendorff heart proarrhythmia model: predictive value for clinical identification of Torsades de Pointes. Br J Pharmacol. 149: 845-860.
Le Douarin NM and Dupin E. (2003) Multipotentiality of the neural crest. Curr Opin Genet Dev. 13: 529-536.
Lee A. (2005) Isolation of neural stem cells from the postnatal cerebellum. Nat Neurosci. 8: 723-729.
Lee EW, et al. (2003) Neuropeptide Y induces ischemic angiogenesis and restores function of ischemic skeletal muscles. J Clin Invest. 111: 1853-1862.
Lee G, et al. (2007) Isolation and directed differentiation of neural crest stem cells derived from human embryonic stem cells. Nat Biotechnol. 25: 1468-1475.
Lee G, et al. (2010) Derivation of neural crest cells from human pluripotent stem cells. Nat Protoc. 5: 688-701.
Lee HY, et al. (2004) Instructive role of Wnt/beta-catenin in sensory fate specification in neural crest stem cells. Science. 303: 1020-1023.
Lee MJ, et al. (2003) Hereditary sensory neuropathy is caused by a mutation in the delta subunit of the cytosolic chaperonin-containing t-complex peptide-I (Cct4) gene. Hum Mol Genet. 12: 1917-1925.
Lesbordes JC, et al. (2002) In vivo electrotransfer of the cardiotrophin-1 gene into skeletal muscle slows down progression of motor neuron degeneration in pmn mice. Hum Mol Genet. 11: 1615-1625.
Lescaudron L, et al. (1999) Blood borne macrophages are essential for the triggering of muscle regeneration following muscle transplant. Neuromuscul Disord. 9: 72-80.
Levenberg S, et al. (2003) Differentiation of human embryonic stem cells on three-dimensional polymer scaffolds. Proc Natl Acad Sci U S A. 100: 12741-12746.
LeVine SM and Goldman JE. (1988) Embryonic divergence of oligodendrocyte and astrocyte lineages in developing rat cerebrum. J Neurosci. 8: 3992-4006.
Li B-S, et al. (2001) Regulation of NMDA receptors by cyclin-dependent kinase-5 Proc Natl Acad Sci US A. 98: 12742-12747.
Li L, et al. (1992) Regulation of muscle cell growth and differentiation by the MyoD family of helix-loop-helix proteins. Adv Cancer Res. 58: 95-119.
Li M, et al. (2005) Comparison of selective attachment and growth of smooth muscle cells on gelatin- and fibronectin-coated micropattems. J Nanosci Nanotechnol. 5: 1809-1815.
Li MX, et al. (2001) Opposing actions of protein kinase A and C mediate Hebbian synaptic plasticity. Nat Neurosci. 4: 871-872.
Li S, et al. (2006) Predicting essential components of signal transduction networks: a dynamic model of guard cell abscisic acid signaling. PLoS Biol. 4:e312.
Li XJ, et al. (2005) Specification of motoneurons from human embryonic stem cells. Nat Boltechnol. 23: 215-221.
Lim GP, et al. (2001) The curry spice curcumin reduces oxidative damage and amyloid pathology in an Alzheimer transgenic mouse. J Neurosci. 21: 8370-8377.
Lim UM, et a. (2006) Derivation of Motor Neurons from three Clonal Human Embryonic Stem Cell Lines. CurrNeurovasc Res. 3: 281-288.
Lin JW, et al. (2008) Region [corrected] of slowed conduction acts as core for spiral wave reentry in cardiac cell monolayers. Am J Physiol Heart Circ Physiol. 294: H58-H65.

(56) References Cited

OTHER PUBLICATIONS

Lin LF, et al. (1993) GDNF: a glial cell line-derived neurotrophic factor for midbrain dopaminergic neurons. Science. 260: 1130-1132.
Lipsett MA, et al. (2007) Acinar plasticity: development of a novel in vitro model to study human acinar-to-duct-to-islet differentiation. Pancreas. 34: 452-457.
Lipton SA. (2006) Paradigm shift in neuroprotection by NMDA receptor blockade: Memantine and beyond. Nat Rev Drug Discov. 5: 160-170.
Lisak RP, et al. (1997) The role of cytokines in Schwann cell damage, protection, and repair. J Infect Dis. 176 Suppl 2: S173-S179.
Liu CN, et al. (2000) Spinal nerve injury enhances subthreshold membrane potential oscillations m DRG neurons: relation to neuropathic pam. J Neurophysiol. 84: 205-215.
Liu J, et al. (2008) Electrophysiological and Immunocytochemical Characterization of DRG Neurons on an Organosilane Surface in Serum Free Medium. In Vitro Cell Dev Biol Anim. 44: 162-168.
Liu S. et al. (2000) Embryonic stem cells differentiate into oligodendrocytes and myelinate in culture and after spinal cord transplantation. Proc Natl Acad Sci USA. 97: 6126-6131.
Liu TX, et al. (2006) Blinded validation of the isolated arterially perfused rabbit ventricular wedge in preclinical assessment of drug-induced proarrhythmias. Heart Rhythm. 3: 948-956.
Liu WP, et al. (2005) Enantioselectivity in environmental safety of current chiral insecticides. Proc Natl Acad Sci US A. 102: 701-706.
Lochter AJ, et al. (1995) Control of neuronal morphology in vitro: interplay between adhesive substrate forces and molecular instruction. J Neurosci Res. 42:145-158.
Long C, et al. (2012) Design optimization of liquid-phase flow patterns for microfabricated lung on a chip. Ann Biomed Eng. 40: 1255-1267.
Lou XJ. (2009) Polarization fatigue in ferroelectric thin films and related materials. Journal of Applied Physics. 105: 024101-024124.
Love S. (2003) Neuronal expression of cell cycle-related proteins after brain ischaemia in man. Neurosci Lett. 353: 29-32.
Lu B, et al. (1996) Expression of synapsin I correlates with maturation of the neuromuscular synapse. Neuroscience. 74: 1087-1097.
Lu HR, et al. (2006) In-vitro experimental models for the risk assessment of antibiotic-induced QT prolongation. Eur J Pharmacol. 553: 229-239.
Ludwig T and A Thomson J. (2007) Defined, feeder-independent medium for human embryonic stem cell culture. Curr Protoc Stem Cell Biol. Chapter 1: Unit 1C.2.
Lund AE and Narahashi T. (1982) Dose-dependent interaction of the pyrethroid isomers with sodium channels of squid axon membranes. Neurotoxicology. 3: 11-24.
Luo Y, et al. (2006) Effects of growth factors on extracellular matrix production by vocal fold fibroblasts in 3-dimensional culture. Tissue Eng. 12: 3365-3374.
Lyles JM, et al. (1992) Matrigel enhances myotube development in a serum-free defined medium. Intl Dev Neurosci. 10: 59-73.
Ma W, et al. (1998) Neuronal and glial epitopes and transmitter-synthesizing enzymes appear in parallel with membrane excitability during neuroblastoma x glioma hybrid differentiation. Brain Res Dev Brain Res. 106: 155-163.
Machida S, et al. (2004) Primary rat muscle progenitor cells have decreased proliferation and myotube formation during passages. Cell Prolif. 37: 267-277.
Maduell F. (2005) Hemodiafiltration. Hemodial Int. 9: 47-55.
Mahler GJ, et al. (2009a) Characterization of a gastrointestinal tract microscale cell culture analog used to predict drug toxicity. Biotechnol Bioeng. 104: 193-205.
Mahler GJ, et al. (2009b) Characterization of Caco-2 and HT29-MTX cocultures in an in vitro digestion/cell culture model used to predict iron bioavailability. J Nutr Biochem. 20: 494-50.

Malerba A, et al. (2009) Selection of multipotent cells and enhanced muscle reconstruction by myogenic macrophage-secreted factors. Exp Cell Res. 315:915-927.
Malm C, et al. (2004) Leukocytes, cytokines, growth factors and hormones in human skeletal muscle and blood after uphill or downhill running. J Physiol. 556: 983-1000.
Malo N, et al. (2006) Statistical practice in high-throughput screening data analysis. Nat Biotechnol. 24: 167-175.
Marhl M, et al. (2000) Complex calcium oscillations and the role of mitochondria and cytosolic proteins. Biosystems. 57: 75-86.
Marona HRN, et al. (1999) Determination of sparfloxacin and its degradation products by HPLC-PDA. J Antimicrob Chemother. 44: 301-302.
Marques MJ, et al. (1997) Ciliary neurotrophic factor stimulates in vivo myotube formation in mice. Neurosci Lett. 234: 43-46.
Mars T, et al. (2001) Differentiation of glial cells and motor neurons during the formation of neuromuscular junctions in cocultures of rat spinal cord explant and human muscle. J Comp Neurol. 438: 239-251.
Mars T, et al. (2003) Functional innervation of cultured human skeletal muscle proceeds by two modes with regard to agrin effects. Neuroscience. 118: 87-97.
Martin-Caraballo M and Greer JJ. (2000) Development of potassium conductances in perinatal rat phrenic motoneurons. J Neurophysiol. 83: 3497-3508.
Martinou JC, et al. (1992) Cholinergic differentiation factor (CDF/LIF) promotes survival of isolated rat embryonic motoneurons in vitro. Neuron. 8: 737-744.
Masu Y, et al. (1993) Disruption of the CNTF gene results in motor neuron degeneration. Nature. 365: 27-32.
Matsakas A and Patel K. (2009) Skeletal muscle fibre plasticity in response to selected environmental and physiological stimuli. Histol Histopathol. 24: 611-629.
Matsuda T, et al. (1992) Two-dimensional cell manipulation technology. An artificial neural circuit based on surface microphotoprocessing. ASAIO J. 38:M243-M247.
Matthews PB. (1964) Muscle spindles and their motor control. Physiol Rev. 44:219-288.
Mattson MP, et al. (1992) Beta-Amyloid Peptides Destabilize Calcium Homeostasis and Render Human Cortical-Neurons Vulnerable to Excitotoxicity. J Neurosci. 12: 376-389.
Matzno S, et al. (2003) Evaluation of the synergistic adverse effects of concomitant therapy with statins and fibrates on rhabdomyolysis. J Pharm Pharmacol. 55: 795-802.
Maves L, et al. (2007) Pbx homeodomain proteins direct Myod activity to promote fast-muscle differentiation. Development. 134: 3371-3382.
Maynard EM. (2001) Visual prostheses. Annu Rev Biomed Eng. 3: 145-168.
McAuliffe GJ, et al. (2008) Development of a gastrointestinal tract microscale cell culture analog to predict drug transport. Mol Cell Biomech. 5: 119-132.
McBeath R, et al. (2004) Cell shape, cytoskeletal tension, and RhoA regulate stem cell lineage commitment. Dev Cell. 6: 483-495.
McDevitt TC, et al. (2002) In vitro generation of differentiated cardiac myofibers on micropatterned laminin surfaces. J Biomed Mater Res. 60: 472-479.
McMahon JA, et al. (1998) Noggin-mediated antagonism of BMP signaling is required for growth and patterning of the neural tube and somite. Genes Dev. 12:1438-1452.
Megeney LA, et al. (1996) bFGF and LIF signaling activates STAT3 in proliferating myoblasts. Dev Genet. 19: 139-145.
Mehra S, et al. (2004) A boolean algorithm for reconstructing the structure of regulatory networks. Metab Eng. 6: 326-339.
Meijer L and Raymond E. (2003) Roscovitine and other purines as kinase inhibitors. From starfish oocytes to clinical trials. Ace Chem Res. 36: 417-425.
Melendez-Vasquez CV, et al. (2001) Nodes of Ranvier form in association with ezrin-radixin-moesin (ERM)-positive Schwann cell processes. Proc Natl Acad Sci US A. 98: 1235-1240.
Mendelsohn JD, et al. (2003) Rational design of cytophilic and cytophobic polyelectrolyte multilayer thin films. Biomacromolecules. 2003 4: 96-106.

(56) References Cited

OTHER PUBLICATIONS

Menendez L, et al. (2011) Wnt signaling and a Smad pathway blockade direct the differentiation of human pluripotent stem cells to multipotent neural crest cells. Proc Natl Acad Sci US A. 108: 19240-19245.
Menn B, et al. (2010) Delayed treatment with systemic (S)-roscovitine provides neuroprotection and inhibits in vivo CDK5 activity increase in animal stroke models. PLoS One. 5: e1211.
Metzger SW, et al. (1999) Development and characterization of surface chemistries for microfabricated biosensors. J of Vacuum Sci & Tech a-Vacuum Surfaces and Films. 17: 2623-2628.
Meyer G and Nabil MA. (1988) Novel optical approach to atomic force microscopy. Applied Physics Letters. 53: 1045-1047.
Meyer T, et al. (2004) Micro-electrode arrays in cardiac safety pharmacology—A novel tool to study QT interval prolongation. Drug Saf. 27: 763-772.
Meyer T, et al. (2004b) QT-screen: high-throughput cardiac safety pharmacology by extracellular electrophysiology on primary cardiac myocytes. Assay Drug Dev Technol. 2: 507-514.
Miles GB, et al. (2004) Functional properties of motoneurons derived from mouse embryonic stem cells. J Neurosci. 24: 7848-7858.
Miller FD. (2007) Riding the waves: neural and nonneural ongms for mesenchymal stem cells. Cell Stem Cell. 1: 129-130.
Miller SC, et al. (1988) Tumor necrosis factor inhibits human myogenesis in vitro. Mol Cell Biol. 8: 2295-2301.
Mitsumoto H, et al. (2001) Effects of cardiotrophin-1 (CT-1) in a mouse motor neuron disease. Muscle Nerve. 24: 769-777.
Mizuseki K, et al. (2003) Generation of neural crest-derived peripheral neurons and floor plate cells from mouse and primate embryonic stem cells. Proc Natl Acad Sci US A. 100: 5828-5833.
Moe GK. (1962) On the multiple wavelet hypothesis of atrial fibrillation. Arch Int Pharmacodyn Ther. 183-188.
Mohammed JS, et al. (2004) Micropatterning of nanoengineered surfaces to study neuronal cell attachment in vitro. Biomacromolecules. 5: 1745-1755.
Mohan DK, et al. (2006) Toxin detection based on action potential shape analysis using a realistic mathematical model of differentiated NG 108-15 cells. Biosens Bioelectron. 21: 1804-1811.
Mokry J, et al. (2007) Differentiation of neural stem cells into cells of oligodendroglial lineage. Acta Medica (Hradec Kralove). 50: 35-41.
Molnar P, et al. (2007) Photolithographic Patterning of C2C12 Myotubes using Vitronectin as Growth Substrate in Serum-Free Medium. Biotechnol Prog. 23:265-268.
Molnar P, et al. (2007b) Synaptic connectivity in engineered neuronal networks. Methods Mol Biol. 403: 165-173.
Molnar P, et al. (2007c) Modeling of action potential generation in NG 108-15 cells. Methods Mol Biol. 403: 175-184.
Monaco EA 3rd and Vallano ML. (2005) Roscovitine triggers excitotoxicity in cultured granule neurons by enhancing glutamate release. Mol Pharmacol. 68:1331-1342.
Monaco EA 3rd. (2004) Recent evidence regarding a role for Cdk5 dysregulation in Alzheimer's disease. Curr Alzheimer Res. 1: 33-38.
Monyer H, et al. (1994) Developmental and regional expression in the rat brain and functional properties of four NMDA receptors. Neuron. 12: 529-540.
Moore JW, et al. (1991) The mRNAs encoding acidic FGF, basic FGF and FGF receptor are coordinately downregulated during myogemc differentiation. Development. 111: 7 41-748.
Morefield SI, et al. (2000) Drug evaluations using neuronal networks cultured on microelectrode arrays. Biosens Bioelectron. 15: 383-396.
Morin F, et al. (2006) Constraining the connectivity of neuronal networks cultured on microelectrode arrays with microfluidic techniques: a step towards neuron-based functional chips. Biosens Bioelectron. 21: 1093-1100.
Morrow NG, et al. (1990) Increased expression of fibroblast growth factors in a rabbit skeletal muscle model of exercise conditioning. J Clin Invest. 85: 1816-1820.
Motamed K, et al. (2003) Fibroblast growth factor receptor-I mediates the inhibition of endothelial cell proliferation and the promotion of skeletal myoblast differentiation by SPARC: a role for protein kinase A. J Cell Biochem. 90: 408-423.
Moulard G, et al. (1998) Improvement of the cantilever beam technique for stress measurement during the physical vapor deposition process. J Vac Science Technol A. 16(2): 736-742.
Mousavi K, et al. (2004) BDNF rescues myosin heavy chain IIB muscle fibers after neonatal nerve injury. Am J Physiol Cell Physiol. 287: C22-C29.
Mrksich M. (2000) A surface chemistry approach to studying cell adhesion. Biosensors & Bioelectronics. 29: 267-273.
Mufti NA and Shuler ML. (1998) Different in Vitro Systems Affect CYPIAI Activity in Response to 2,3,7,8-Tetrachlorodibenzo-p-dioxin. Toxicol In Vitro. 12: 259-272.
Mulkey D, et al. (2003) Hyperbaric oxygen and chemical oxidants stimulate $CO_2/H+$-sensitive neurons in rat brain stem slices. J Appl Physiol. 95: 910-92.
Mullen RJ, et al. (1992) NeuN, a neuronal specific nuclear protein in vertebrates. Development. 116: 201-211.
Muller FJ, et al. (2006) Gene therapy: can neural stem cells deliver? Nat Rev Neurosci. 7: 75-84.
Muller P and Saul A. (2004) Elastic effects on surface physics. Surface Science Reports. 54: 157-258.
Muller T, et al. (1999) A 3-D microelectrode system for handling and caging single cells and particles. Biosens Bioelectron. 14: 247-256.
Munaron L. (2002) Calcium signalling and control of cell proliferation by tyrosine kinase receptors (review). Int J Mol Med. 10: 671-676.
Munsterberg AE, et al. (1995) Combinatorial signaling by Sonic hedgehog and Wnt family members induces myogenic bHLH gene expression in the somite. Genes Dev. 9: 2911-2922.
Muraki K, et al. (1994) Effects of noradrenaline on membrane currents and action potential shape in smooth muscle cells from guinea-pig ureter. J Physiol. 481:617-627.
Murgia M, et al. (2000) Ras is involved in nerve-activity-dependent regulation of muscle genes. Nat Cell Biol. 2: 142-147.
Murphy M, et al. (1994) FGF2 regulates proliferation of neural crest cells, with subsequent neuronal differentiation regulated by LIF or related factors. Development. 120: 3519-3528.
Mutyala MSK, et al. (2009) Mechanical and electronic approaches to improve the sensitivity of microcantilever sensors. Acta Mechanica Sinica. 25: 1-12.
Nagy Z, et al. (1997) Cell cycle markers in the hippocampus in Alzheimer's disease. Acta Neuropathol. 94: 6-15.
Nakamura S, et al. (2010) Analysis of cardiac toxicity caused by cyclophosphamide in the H9c2 cell line and isolated and perfused rat hearts. Gan to Kagaku Ryoho. 37: 677-680. Abstract only in English.
Nakamura Y, et al. (2007) The in vitro metabolism of a pyrethroid insecticide, permethrin, and its hydrolysis products in rats. Toxicology. 235: 176-184.
Nam Y, et al. (2006) Neural recording and stimulation of dissociated hippocampal cultures using microfabricated three-dimensional tip electrode array. J Neurosci Methods. 155: 296-299.
Nash MP, et al. (2006) Evidence for multiple mechanisms in human ventricular fibrillation. Circulation. 114: 536-542.
Nat R. (2011) Cortical network from human embryonic stem cells. J Cell Mol Med. 15: 1429-1431.
Natarajan A, et al. (2006) Microelectrode array recordings of cardiac action potentials as a high throughput method to evaluate pesticide toxicity. Toxicol In Vitro. 20: 375-381.
Natarajan A, et al. (2008) Growth and electrophysiological properties of rat embryonic cardiomyocytes on hydroxyl- and carboxyl-modified surfaces. J Biomater Sci Polym Ed. 19: 1319-1331.
Natarajan A, et al. (2011) Patterned cardiomyocytes on microelectrode arrays as a functional, high information content drug screening platform. Biomaterials. 32:4267-4274.
Natarajan A, et al. (2013) Engineered In Vitro Feed-Forward Networks. J Biotechnol Biomater. 3:153.

(56) References Cited

OTHER PUBLICATIONS

Natarajan AR, et al. (2004) Intrinsic cardiac catecholamines help maintain beating activity in neonatal rat cardiomyocyte cultures. Pediatr Res. 56: 411-417.
Nazaret C, et al. (2009) Mitochondrial energetic metabolism: a simplified model of TCA cycle with ATP production. J Theor Biol. 258: 455-464.
Nelson CE, et al. (1996) Analysis of Hox gene expression in the chick limb bud. Development. 122: 1449-1466.
Nelson CM and Bisell MJ. (2006) of extracellular matrix, scaffolds, and signaling: tissue architecture regulates development, homeostasis, and cancer. Annu Rev Cell Dev Biol. 22: 287-309.
Nelson PG, et al. (1993) Synapse elimination from the mouse neuromuscular junction in vitro: a non-Hebbian activity-dependent process. J Neurobiol. 24:1517-1530.
Nelson PG. (1975) Nerve and muscle cells in culture. Physiol Rev. 55: 1-61.
Nerbonne JM and Kass RS. (2005) Molecular physiology of cardiac repolarization. Physiol Rev. 85: 1205-1253.
Nguemo F, et al. (2012) In vitro model for assessing arrhythmogenic properties of drugs based on high-resolution impedance measurements. Cell Physiol Biochem. 29: 819-832.
Nguyen L, et al. (2006) The Yin and Yang of cell cycle progression and differentiation in the oligodendroglial lineage. Ment Retard Dev Disabil Res Rev. 12: 85-96.
Nicolelis MAL and Ribeiro S. (2002) Multielectrode recordings: the next steps. Curr Opin Neurobiol. 12: 602-606.
Nimmrich V, et al. (2008) Amyloid beta oligomers (a beta(I-42) globulomer) suppress spontaneous synaptic activity by inhibition of P/Q-type calcium currents. J Neurosci. 28: 788-797.
Nishikawa J, et al. (2005) Increase of Cardiotrophin-1 immunoreactivity in regenerating and overloaded but not denervated muscles of rats. Neuropathology. 25: 54-65.
Nishimaru H, et al. (2005) Mammalian motor neurons corelease glutamate and acetylcholine at central synapses. Proc Natl Acad Sci US A. 102: 5245-5249.
Nistor GI, et al. (2005) Human embryonic stem cells differentiate into oligodendrocytes in high purity and myelinate after spinal cord transplantation. Glia. 49: 385-396.
Noble D. (2004) Modeling the heart. Physiology (Bethesda). 19: 191-197.
Noll E and Miller RH. (1993) Oligodendrocyte precursors originate at the ventral ventricular zone dorsal to the ventral midline region in the embryonic rat spinal cord. Development. 118: 563-573.
Normann RA, et al. (1999) A neural interface for a cortical vision prosthesis. Vision Res. 39: 2577-2587.
Norris W, et al. (2000) Slow muscle induction by Hedgehog signalling in vitro. J Cell Sci. 113: 2695-2703.
Nyitrai G, et al. (2006) Extracellular level of GABA and Glu: III VIVO microdialysis-HPLC measurements. Curr Top Med Chem. 6: 935-940.
Oakley RA, et al. (1997) Neurotrophin-3 promotes the differentiation of muscle spindle afferents in the absence of peripheral targets. J Neurosci. 17: 4262-4274.
O'Connor SM, et al. (2000) Immobilization of neural cells in three-dimensional matrices for biosensor applications. Biosens Bioelectron. 14: 871-881.
Offenhausser A and Knoll W. (2001) Cell-transistor hybrid systems and their potential applications. Trends Biotechnol. 19: 62-66.
Offenhausser A, et al. (1997) Field-effect transistor array for monitoring electrical activity from mammalian neurons in culture. Biosensors and Bioelectronics. 12: 819-826.
Oh TI, et al. (2007) Real-time fluorescence detection of multiple microscale cell culture analog devices in situ. Cytometry A. 71: 857-865.
Oliver L, et al. (1992) Acidic fibroblast growth factor (aFGF) in developing normal and dystrophic (mdx) mouse muscles. Distribution in degenerating and regenerating mdx myofibres. Growth Factors. 7: 97-106.

Olson E. (1992) Activation of muscle-specific transcription by myogenic helixloop-helix proteins. Symp Soc Exp Biol. 46: 331-341.
Olson EN and Williams RS. (2000) Calcineurin Signaling and Muscle Remodeling. Cell. 101: 689-692.
Olson EN, et al. (1992) MyoD and the paradoxes of myogenesis. Curr Biol. 2: 35-37.
Olson EN. (1992) Interplay between proliferation and differentiation within the myogenic lineage. Dev Biol. 154: 261-272.
Olwin BB, et al. (1992) Repression of myogenic differentiation by aFGF, bFGF, and K-FGF is dependent on cellular heparan sulfate. J Cell Biol. 118: 631-639.
Oppenheim RW, et al. (1991) Control of embryonic motoneuron survival in vivo by ciliary neurotrophic factor. Science. 251: 1616-1618.
Oppenheim RW, et al. (2001) Cardiotrophin-1, a muscle-derived cytokine, is required for the survival of subpopulations of developing motoneurons. J Neurosci. 21: 1283-1291.
Orentas DM and Miller RH. (1998) Regulation of oligodendrocyte development. Mol Neurobiol. 18: 247-259.
Orlov SN and Hamet P. (2006) Intracellular monovalent ions as second messengers. J Membr Biol. 210: 161-172.
Ostuni E, et al. (2000) Patterning mammalian cells using elastomeric membranes. Langmuir. 16: 7811-7819.
Oumata N, et al. (2008) Roscovitine-derived, dual-specificity inhibitors of cyclindependent kinases and casein kinases 1. J Med Chem. 51: 5229-5242.
Padmanabhan J, et al. (1999) Role of cell cycle regulatory proteins in cerebellar granule neuron apoptosis. J Neurosci. 19: 8747-8756.
Pagan SM, et al. (1996) Surgical removal of limb bud Sonic hedgehog results in posterior skeletal defects. Dev Biol. 180: 35-40.
Pancrazio JJ, et al. (1998) Portable cell-based biosensor system for toxin detection. Sensors and Actuators B Chem. 53: 179-185.
Park J, et al. (2005) Real-time measurement of the contractile forces of self-organized cardiomyocytes on hybrid biopolymer microcantilevers. Anal Chem. 77: 6571-6580.
Parker KK, et al. (2008) Myofibrillar architecture m engineered cardiac myocytes. Circ Res. 103: 340-342.
Parng C, et al. (2002) Zebrafish: A Preclinical Model for Drug Screening. Assay Drug Dev Technol. 1: 41-48.
Parviz M and Gross GW. (2007) Quantification of zinc toxicity using neuronal networks on microelectrode arrays. Neurotoxicolo12:v. 28: 520-531.
Paspalas CD and Papadopoulos GC. (1996) Ultrastructural relationships between noradrenergic nerve fibers and non-neuronal elements in the rat cerebral cortex. Glia. 17: 133-146.
Payne ET, et al. (2006) Nutritional therapy improves function and complements corticosteroid intervention in mdx mice. Muscle Nerve. 33: 66-77.
Peng HB, et al. (2003) Differential effects of neurotrophins and schwann cell-derived signals on neuronal survival/growth and synaptogenesis. J Neurosci. 23:5050-5060.
Peroulakis ME, et al. (2000) Ciliary neurotrophic factor increases muscle fiber number in the developing levator ani muscle of female rats. Neurosci Lett. 296: 73-76.
Perrier AL, et al. (2004) Derivation of midbrain dopamine neurons from human embryonic stem cells. Proc Natl Acad Sci USA. 101: 12543-12548.
Peters A. (1964) Observations on the Connexions Between A709. Myelin Sheaths and Glial Cells in The Optic Nerves of Young Rats. J Anat. 98: 125-134.
Peterson CA, et al. (1999) Effects of moisture on Fowler—Nordheim characterization of thin silicon-oxide films. J Vac Science Technol A. 17: 2753-2758.
Pette D and Staron S. (2001) Transitions of muscle fiber phenotypic profiles. Histochem and Cell Biol. 115: 359-372.
Pette D, et al. (2002) Partial fast-to-slow conversion of regenerating rat fast-twithc muscle by chronic low frequency stimulation. J Muscle Res Cell Motil. 3:215-221.
Pfeiffer SE, et al. (1993) The oligodendrocyte and its many cellular processes. Trends Cell Biol. 3: 191-197.
Pfrieger FW and Barres BA. (1997) Synaptic efficacy enhanced by glial cells in vitro. Science. 277: 1684-1687.

(56) References Cited

OTHER PUBLICATIONS

Pijnappels DA, et al. (2007) Resynchronization of separated rat cardiomyocyte fields with genetically modified human ventricular scar fibroblasts. Circulation. 116: 2018-2028.
Pillekamp F, et al. (2012) Contractile properties of early human embryonic stem cell-derived cardiomyocytes: beta-adrenergic stimulation induces positive chronotropy and lusitropy but not inotronv. Stem Cells Dev. 21: 2111-2121.
Podratz J, et al. (2004) Antioxidants are necessary for myelination of dorsal root ganglion neurons, in vitro. Glia. 45: 54-58.
Pomp O, et al. (2005) Generation of peripheral sensory and sympathetic neurons and neural crest cells from human embryonic stem cells. Stem Cells. 23: 923-930.
Pomp O, et al. (2008) PA6-induced human embryonic stem cell-derived neurospheres: a new source of human peripheral sensory neurons and neural crest cells. Brain Res. 1230: 50-60.
Pontier C, et al. (2001) HT29-MTX and Caco-2/TC7 monolayers as predictive models for human intestinal absorption: role of the mucus layer. J Pharm Sci. 90:1608-1619.
Popat KC, et al. (2004) Surface modification of nanoporous alumina surfaces with poly(ethylene glycol). Langmuir. 20: 8035-8041.
Popat KC, et al. (2004b) Quantitative xps analysis of peg-modified silicon surfaces. J Phys Chem. 108: 5185-5188.
Porto F, et al. (2008) Towards a Scientific Model Management System. ER Workshops 2008. NCS 5232: 55-65.
Pouton CW and Haynes JM. (2005) Pharmaceutical applications of embryonic stem cells. Adv Drug Deliv Rev. 57: 1918-1934.
Powell C, et al. (1999) Tissue engineered human bioartificial muscles expressing a foreign recombinant protein for gene therapy. Hum Gene Ther. 10: 565-577.
Powell C, et al. (2002) Mechanical stimulation improves tissue-engineered human skeletal muscle. Am J Physiol Cell Physiol. 283: C1557-C1565.
Price PJ and Brewer GJ. (2001) Serum-Free Media for Neural Cell Cultures. Protocols for Neural Cell Cultures, 3rd Ed, Humana Press Inc., Totowa, NJ, Chapter 19, 255-264.
Pringle NP, et al. (1996) Determination of neuroepithelial cell fate: induction of the oligodendrocyte lineage by ventral midline cells and sonic hedgehog. Dev Biol. 177: 30-42.
Quinn LS, et al. (1990) Paracrine control of myoblast proliferation and differentiation by fibroblasts. Dev Biol. 140: 8-19.
Raible DW and Mc Morris FA. (1990) Induction of oligodendrocyte differentiation by activators of adenylate cyclase. J Neurosci Res. 27: 43-46.
Raible DW and McMorris FA. (1989) Cyclic AMP regulates the rate of differentiation of oligodendrocytes without changing the lineage commitment of their progenitors. Dev Biol. 133: 437-446.
Raiteri R, et al. (2001) Micromechanical cantilever-based biosensors. Sensors and Actuators B-Chemical. 79: 115-126.
Rajnicek AM, et al. (1997) Contact guidance of CNS neurites on grooved quartz: influence of groove dimensions, neuronal age and cell type. J Cell Sci. 110: 2905-2913.
Raley-Susman KM, et al. (1991) Regulation of intracellular pH in cultured hippocampal neurons by an amiloride-insensitive Na+/H+ exchanger. J Biol Chem. 266: 2739-2745.
Rampe D, et al. (1997) A mechanism for the proarrhythmic effects of cisapride (Propulsid): high affinity blockade of the human cardiac potassium channel HERG. FEBS Lett. 417: 28-32.
Ravenscroft MS, et al. (1998) Developmental Neurobiology Implications from Fabrication and Analysis of Hippocampal Neuronal Networks on Patterned Silane-Modified Surfaces. J Am Chem Soc. 120: 12169-12177.
Ravenscroft-Chang MS, et al. (2010) Altered calcium dynamics in cardiac cells grown on silane-modified surfaces. Biomaterials. 31: 602-607.
Recanatini M, et al. (2005) QT prolongation through hERG K(+) channel blockade: current knowledge and strategies for the early prediction during drug development. Med Res Rev. 25: 133-166.
Rekling JC, et al. (2000) Synaptic control of motoneuronal excitability. Physiol Rev. 80: 767-852.
Reppel M, et al. (2004) Beta-adrenergic and muscarinic modulation of human embryonic stem cell-derived cardiomyocytes. Cell Physiol Biochem. 14: 187-196.
Reppel M, et al. (2005) The electrocardiogram of human embryonic stem cell-derived cardiomyocytes. J Electrocardiol. 38: 166-170.
Reppel M, et al. (2007) Effect of cardioactive drugs on action potential generation and propagation in embryonic stem cell-derived cardiomyocytes. Cell Physiol Biochem. 19: 213-224.
Revzin A, et al. (2003) Surface Engineering with Poly(ethylene glycol) Photolithography to Create High-Density Cell Arrays on Glass. Langmuir. 19:9855-9862.
Reyes D, et al. (2004) Micropatterning neuronal cells on polyelectrolyte multilayers. Langmuir. 20: 8805-8811.
Richards S, et al. (2008) Development of defined media for the serum-free expansion of primary keratinocytes and human embryonic stem cells. Tissue Eng Part C Methods. 14: 221-232.
Richert L, et al. (2004) pH dependent growth of poly(L-lysine)/poly(L-glutamic) acid multilayer films and their cell adhesion properties. Surface Science. 570: 13-29.
Riley M. (1993) Functions of the gene products of *Escherichia coli*. Microbiol Rev. 57: 862-952.
Robertson TA, et al. (2000) Comparison of astrocytic and myocytic metabolic dysregulation in apolipoprotein E deficient and human apolipoprotein E transgenic mice. Neuroscience. 98: 353-359.
Rodan SB, et al. (1989) Effects of acidic and basic fibroblast growth factors on osteoblastic cells. Connect Tissue Res. 20: 283-288.
Roden DM, et al. (2002) Cardiac ion channels. Annu Rev Physiol. 64: 431-475.
Rogister B, et al. (1999) From neural stem cells to myelinating oligodendrocytes. Mol Cell Neurosci. 14: 287-300.
Rohr S, et al. (1991) Patterned growth of neonatal rat heart cells in culture. Morphological and electrophysiological characterization. Circ Res. 68: 114-130.
Rosati B and McKinnon D. (2004) Regulation of ion channel expression. Circ Res. 94: 874-883.
Rosenberg SS, et al. (2008) The geometric and spatial constraints of the microenvironment induce oligodendrocyte differentiation. Proc Natl Acad Sci USA. 105: 14662-14667.
Rumsey JW, et al. (2008) Tissue Engineering Intrafusal Fibers: Dose and Time Dependent Differentiation of Nuclear Bag Fibers in a Defined In Vitro System using Neuregulin 1- -1. Biomaterials. 29: 994-1004.
Rumsey JW, et al. (2009) Node of Ranvier formation on motoneurons in vitro. Biomaterials. 30: 3567-3572.
Rumsey JW, et al. (2010) Tissue engineering the mechanosensory circuit of the stretch reflex arc: sensory neuron innervation of intrafusal muscle fibers. Biomaterials. 31: 8218-8227.
Rutten WLC. (2002) Selective electrical interfaces with the nervous system. Annu Rev Biomed Eng. 4: 407-452.
Sakuma K, et al. (2000) Differential adaptation of growth and differentiation factor 8/myostatin, fibroblast growth factor 6 and leukemia inhibitory factor in overloaded, regenerating and denervated rat muscles. Biochim Biophys Acta. 1497: 77-88.
Sala M, et al. (2009) Electrophysiological changes of cardiac function during antidepressant treatment. Ther Adv Cardiovasc Dis. 3: 29-43.
Sander D, et al. (1995) A simple technique to measure stress in ultrathin films during growth. Rev Sci Instrum. 66: 4734.
Sanes JR and Lichtman JW. (1999) Development of the vertebrate neuromuscular junction. Annu Rev Neurosci. 22: 389-442.
Sanes JR and Lichtman JW. (2001) Induction, assembly, maturation and maintenance of a postsynaptic apparatus. Nat Rev Neurosci. 2: 791-805.
Sanes JR. (1997) Genetic analysis of postsynaptic differentiation at the vertebrate neuromuscular junction. Curr Opin Neurobiol. 7: 93-100.
Sasahara K, et al. (2007) Mode of action and functional significance of estrogen-inducing dendritic growth, spinogenesis, and synaptogenesis in the developing Purkinje cell. JNeurosci. 27: 7408-7417.
Sathaye A, et al. (2006) Electrical pacing counteracts intrinsic shortening of action potential duration of neonatal rat ventricular cells in culture. J Mol Cell Cardiol. 41: 633-64.

(56) References Cited

OTHER PUBLICATIONS

Scaal M, et al. (1999) SF/HGF is a mediator between limb patterning and muscle development. Development. 126: 4885-4893.
Schaffner AE, et al. (1995) Investigation of the factors necessary for growth of hippocampal neurons in a defined system. J Neurosci Methods. 62: 111-11.
Scherer J, et al. (1995) Differentiation and maturation of rabbit retinal oligodendrocyte precursor cells in vitro. Brain Res Dev Brain Res. 89: 214-226.
Schiaffino S and Serrano A. (2002) Calcineurin signaling and neural control of skeletal muscle fiber type and size. Trends Pharmacol Sci. 23: 569-575.
Schiaffino S, et al. (2007) Activity-Dependent Signaling Pathways Controlling Muscle Diversity and Plasticity. Physiology. 22: 269-278.
Schluter H and Kaur P. (2009) Bioengineered human skin from embryonic stem cells. Lancet. 374: 1725-1726.
Schneider A, et al. (2006) Glycated polyelectrolyte multilayer films: differential adhesion of primary versus tumor cells. Biomacromolecules. 7: 2882-2889.
Schneider AG, et al. (1999) Muscle LIM protein: expressed in slow muscle and indcued in fast muscle by enhanced contractile activity. Am J Physiol. 276:C900-C906.
Scholzen T and Gerdes J. (2000) The Ki-67 protein: from the known and the unknown. J Cell Physiol. 182: 311-322.
Schulz TC, et al. (2004) Differentiation of human embryonic stem cells to dopaminergic neurons in serum-free suspension culture. Stem Cells. 22: 1218-1238.
Schuster D, et al. (2005) Why drugs fail—a study on side effects in new chemical entities. Curr Pharm Des. 11: 3545-3559.
Schuster R and Holzhutter HG. (1995) Use of mathematical models for predicting the metabolic effect of large-scale enzyme activity alterations. Application to enzyme deficiencies ofred blood cells. Eur J Biochem. 229: 403-418.
Schwab ME. (2002) Repairing the injured spinal cord. Science. 295: 1029-1031.
Schwarz JJ, et al. (1992) The basic region of myogenin cooperates with two transcription activation domains to induce muscle-specific transcription. Mol Cell Biol. 12: 266-275.
Scollon EJ, et al. (2009) In vitro metabolism of pyrethroid pesticides by rat and human hepatic microsomes and cytochrome p450 isoforms. Drug Metab Dispos. 37: 221-228.
Scoote Mand Williams AJ. (2004) Myocardial calcium signalling and arrhythmia pathogenesis. Biochem Biophys Res Commun. 322: 1286-1309.
Scott W, et al. (2001) Human Skeletal Muscle Fiber Type Classifications. Phys Ther. 81: 1810-1816.
Selivanov VA, et al. (2004) Nucleotide-gated KA TP channels integrated with creatine and adenylate kinases: amplification, tuning and sensing of energetic signals in the compartmentalized cellular environment. Mol Cell Biochem. 256-257: 243-256.
Selivanova OM, et al. (2003) Compact globular structure of Thermus thermophilus ribosomal protein S 1 in solution: sedimentation and calorimetric study. J Biol Chem. 278: 36311-36314.
Semsarian C, et al. (1999) Skeletal muscle hypertrophy is mediated by a Ca2+ dependent calcineurin signalling pathway. Nature. 400: 576-581.
Sghirlanzoni A, et al. (2005) Sensory neuron diseases. Lancet Neurol. 4: 349-361.
Shah NM, et al. (1996) Alternative neural crest cell fates are instructively promoted by TGFbeta superfamily members. Cell. 85: 331-343.
Shainberg A, et al. (1976) Induction of acetylcholine receptors in muscle cultures. Pflugers Arch. 361: 255-261.
Shankar GM, et al. (2008) Amyloid-beta protein dimers isolated directly from Alzheimer's brains impair synaptic plasticity and memory. Nat Med. 14:837-842.
Shansky J, et al. (1997) A simplified method for tissue engineering skeletal muscle organoids in vitro. In Vitro Cell Dev Biol Anim. 33: 659-661.
Shansky J, et al. (2006a) Paracrine release of insulin-like growth factor 1 from a bioengineered tissue stimulates skeletal muscle growth in vitro. Tissue Eng. 12:1833-1841.
Shansky J, et al. (2006b) Tissue engineering human skeletal muscle for clinical applications. Culture of Cells for Tissue Engineering. 239-257.
Sheikh SI and Amato AA. (2010) The dorsal root ganglion under attack: the acquired sensory ganglionopathies. Pract Neurol. 10: 326-334.
Sheng Z, et al. (1996) Cardiotrophin-1 displays early expression in the murine heart tube and promotes cardiac myocyte survival. Development. 122: 419-428.
Sheridan DC, et al. (2003) Ca2+-dependent excitation-contraction coupling triggered by the heterologous cardiac/brain DHPR beta2a-subunit in skeletal myotubes. Biophys J. 85: 3739-3757.
Sheridan DC, et al. (2003) Truncation of the carboxyl terminus of the dihydropyridine receptor beta1a subunit promotes Ca2+ dependent excitationcontraction coupling in skeletal myotubes. Biophys J. 84: 220-237.
Sherman DL and Brophy PJ. (2005) Mechanisms of axon ensheathment and myelin growth. Nat Rev Neurosci. 6: 683-690.
Sherman DL, et al. (2005) Neurofascins are required to establish axonal domains for saltatory conduction. Neuron. 48: 737-742.
Shimono K, et al. (2000) Multielectrode Recording of Rhythmic Oscillations in Brain Slices: A Novel Technique for Screening Psychoactive Drugs. Faseb J. 14:1047.
Shin S, et al. (2005) Human motor neuron differentiation from human embryonic stem cells. Stem Cells Dev. 14: 266-269.
Shuler ML. (2012) Modeling life. Ann Biomed Eng. 40: 1399-1407.
Silver JH, et al. (1999) Surface properties and hemocompatibility of alkyl-siloxane monolayers supported on silicone rubber: effect of alkyl chain length and ionic functionality. Biomaterials. 20: 1533-1543.
Simmons A, et al. (2005) Painful lessons. Nat Rev Drug Discov. 4: 800-803.
Simon M, et al. (2003) Effect of NT-4 and BDNF delivery to damaged sciatic nerves on phenotypic recovery of fast and slow muscles fibres. Eur J Neurosci. 18: 2460-2466.
Simpson ML, et al. (2001) Whole-cell biocomputing. Trends Biotechnol. 19:317-323.
Sin A, et al. (2004) The design and fabrication of three-chamber microscale cell culture analog devices with integrated dissolved oxygen sensors. Biotechnol Prog. 20: 338-345.
Singh RP, et al. (2009) Retentive multipotency of adult dorsal root ganglia stem cells. Cell Transplant. 18: 55-68.
Singhvi R, et al. (1994) Engineering cell shape and function. Science. 264: 696-698.
Slepchenko BM, et al. (2003) Quantitative cell biology with the Virtual Cell. Trends Cell Biol. 13: 570-576.
Smith J, et al. (1994) The effects of fibroblast growth factors in long-term primary culture of dystrophic (mdx) mouse muscle myoblasts. Exp Cell Res. 210: 86-93.
Smith JR, et al. (2008) Inhibition of Activin/Nodal signaling promotes specification of human embryonic stem cells into neuroectoderm. Dev Biol. 313:107-1.
Smith PF, et al. (1991) HMG-CoA reductase inhibitor-induced myopathy in the rat: cyclosporine A interaction and mechanism studies. J Pharmacol Exp Ther. 257: 1225-1235.
Smolen PD, et al. (2004) Mathematical Modeling and Analysis of Intracellular Signaling Pathways. From Molecules to Networks—An Introduction to Cellular and Molecular Neuroscience. p. 391-430.
Sofia SJ and Merrill EW. (1997) Protein Adsorption on Poly(ethylene oxide)-Grafted Silicon Surfaces. ACS Symposium Series. 680: 342-360.
Song WK, et al. (1992) H36-alpha 7 is a novel integrin alpha chain that is developmentally regulated during skeletal myogenesis. J Cell Biol. 117: 643-657.
Soni AS, et al. (2008) Determination of critical network interactions: an augmented Boolean pseudo-dynamics approach. IET Syst Biol. 2: 55-63.

(56) References Cited

OTHER PUBLICATIONS

Soundarapandian MM, et al. (2007) Role of K(ATP) channels in protection against neuronal excitatory insults. J Neurochem. 103: 1721-172.

Soundararajan P, et al. (2007) Easy and rapid differentiation of embryonic stem cells into functional motoneurons using sonic hedgehog-producing cells. Stem Cells. 25: 1697-1706.

Spach MS and Heidlage JF. (1995) The stochastic nature of cardiac propagation at a microscopic level. Electrical description of myocardial architecture and its application to conduction. Circ Res. 76: 366-380.

Spach MS. (1983) The role of cell-to-cell coupling in cardiac conduction disturbances. Adv Exp Med Biol. 161: 61-77.

Spargo BJ, et al. (1994) Spatially controlled adhesion, spreading, and differentiation of endothelial cells on self-assembled molecular monolayers. Proc Natl Acad Sci USA. 91: 11070-11074.

Spencer CI, et al. (2001) Actions of pyrethroid insecticides on sodium currents, action potentials, and contractile rhythm in isolated mammalian ventricular myocytes and perfused hearts. J Pharmacol Exp Ther. 298: 1067-1082.

St John PM, et al. (1997) Preferential glial cell attachment to microcontact printed surfaces. J Neurosci Methods. 75: 171-177.

St. George-Hyslop PH and Petit A. (2005) Molecular biology and genetics of Alzheimer's disease.CR Biol. 328: 119-130.

Stavarachi M, et al. (2010) Spinal muscular atrophy disease: a literature review for therapeutic strategies. J Med Life. 3: 3-9.

Steffen LS, et al. (2007) Zebrafish orthologs of human muscular dystrophy genes. BMC Genomics. 8: 7.

Stenger DA, et al. (1992) Coplanar Molecular Assemblies of Aminoalkylsilane and Perfluorinated Alkylsilane-Characterization and Geometric Definition of Mammalian-Cell Adhesion and Growth. J Am Chem Soc. 114: 8435-8442.

Stenger DA, et al. (1993) Surface determinants of neuronal survival and growth on self-assembled monolayers in culture. Brain Res. 630: 136-147.

Stenger DA, et al. (1998) Microlithographic determination of axonal/dendritic polarity in cultured hippocampal neurons. J Neurosci Methods. 82: 167-173.

Sternberger NH, et al. (1985) Immunocytochemistry of myelin basic proteins in adult rat oligodendroglia. J Neuroimmunol. 7: 355-363.

Stett A, et al. (2003) Biological application of microelectrode arrays in drug discovery and basic research. Anal Bioanal Chem. 377: 486-495.

Stevens JL. (2006) Future of toxicology—mechanisms of toxicity and drug safety: where do we go from here? Chem Res Toxicol. 19: 1393-1401.

Stinstra J, et al. (2006) A Model of 3D Propagation in Discrete Cardiac Tissue. Comput Cardiol. 33: 41-44.

Stockwell BR. (2004) Exploring biology with small organic molecules. Nature. 432: 846-854.

Stoney GG. (1909) The Tension of Metallic Films Deposited by Electrolysis. Proc Roy Soc London. 82: 172-175.

Subramanian B, et al. (2010) Tissue-engineered three-dimensional in vitro models for normal and diseased kidney. Tissue Eng Part A. 16: 2821-2831.

Sun L, et al. (2007) JAK1-STAT1-STAT3, a key pathway promoting proliferation and preventing premature differentiation of myoblasts. J Cell Biol. 179: 129-138.

Sung JH and Shuler ML. (2009a) A micro cell culture analog (microCCA) with 3-D hydrogel culture of multiple cell lines to assess metabolism-dependent cytotoxicity of anti-cancer drugs. Lab Chip. 9: 1385-1394.

Sung JH and Shuler ML. (2009b) Prevention of air bubble formation in a microfluidic perfusion cell culture system using a microscale bubble trap. Biomed Microdevices. 11: 731-738.

Sung JH, et al. (2009c) Fluorescence optical detection in situ for real-time monitoring of cytochrome P450 enzymatic activity of liver cells in multiple microfluidic devices. Biotechnol Bioeng. 104: 516-525.

Sung JH, et al. (2010) A microfluidic device for a pharmacokinetic-pharmacodynamic (PK-PD) model on a chip. Lab Chip. 10: 446-455.

Sung JH, et al. (2013) Microfabricated mammalian organ systems and their integration into models of whole animals and humans. Lab Chip. 13: 1201-1212.

Suter W. (2006) Predictive value of in vitro safety studies. Curr Opin Chem Biol. 10: 362-366.

Sutton NM, et al. (2007) Clinical effects and outcome of feline permethrin spot-on poisonings reported to the Veterinary Poisons Information Service (VPIS), London. J Feline Med Surg. 9: 335-339.

Swasdison S, et al. (1992) Formation of highly organized skeletal muscle fibers in vitro. Comparison with muscle development in vivo. J Cell Sci. 102: 643-652.

Swynghedauw B. (1999) Molecular mechanisms of myocardial remodeling. Physiol Rev. 79: 215-262.

Takagishi Y, et al. (2000) Species-specific difference in distribution of voltage-gated L-type Ca(2+) channels of cardiac myocytes. Am J Physiol Cell Physiol. 279: C1963-C1969.

Takahashi T. (1978) Intracellular recording from visually identified motoneurons in rat spinal cord slices. Proc R Soc Lond B Biol Sci. 202: 417-421.

Takashima Y, et al. (2007) Neuroepithelial cells supply an initial transient wave of MSC differentiation. Cell. 129: 1377-1388.

Tan W and Desai TA. (2003) Microfluidic patterning of cells in extracellular matrix biopolymers: effects of channel size, cell type, and matrix composition on pattern integrity. Tissue Eng. 9: 255-267.

Tanaka M, et al. (2005) An Unbiased Cell Morphology Based Screen for New, Biologically Active Small Molecules. PLoS Biol. 3: e128.

Tanaka Y, et al. (2006) An actuated pump on-chip powered by cultured cardiomyocytes. Lab Chip. 6: 362-368.

Tarasenko YI, et al. (2007) Human fetal neural stem cells grafted into contusion-injured rat spinal cords improve behavior. JN eurosci Res. 85: 4 7-57.

Tatosian DA and Shuler ML. (2009) A novel system for evaluation of drug mixtures for potential efficacy in treating multidrug resistant cancers. Biotechnol Bioeng. 103: 187-198.

Termin A and Pette D. (1992) Changes in myosin heavy-chain isoform synthesis of chronically stimulated rat fast-twitch muscle. Eur J Biochem. 204: 569-573.

Terstappen GC, et al. (2007) Target deconvolution strategies in drug discovery. Nat. Rev Drug Discov. 6: 891-9.

Thomas CA, et al. (1972) A miniature microelectrode array to monitor the bioelectric activity of cultured cells. Exp Cell Res. 74: 61-66.

Thomas R. (1973) Boolean formalization of genetic control circuits. J Theor Biol. 1973. 42: 563-585.

Thompson PD, et al. (2006) An assessment of statin safety by muscle experts. Am J Cardiol. 97: 69C-76C.

Thompson RB, et al. (2005) Intracardiac transplantation of a mixed population of bone marrow cells improves both regional systolic contractility and diastolic relaxation. J Heart Lung Transplant. 24: 205-214.

Thorrez L, et al. (2008) Growth, differentiation, transplantation and survival of human skeletal myofibers on biodegradable scaffolds. Biomaterials. 29: 75-84.

Timmerman W and Westerink BH. (1997) Brain microdialysis of GABA and glutamate: what does it signify? Synapse. 27: 242-261.

Tobert JA. (2003) Lovastatin and beyond: the history of the HMGCoA reductase inhibitors. Nat Rev Drug Discov. 2: 517-526.

Toga T, et al. (2007) The 5-HT( 4) agonists cisapride, mosapride, and CJ-033466, a Novel potent compound, exhibit different human ether-a-go-go-related gene (hERG)-blocking activities. J Pharmacol Sci. 105: 207-210.

Tomb JF, et al. (1997) The complete genome sequence of the gastric pathogen Helicobacter pylori. Nature. 388: 539-547.

Torgan CE and Daniels MP. (2001) Regulation of myosin heavy chain expression during rat skeletal muscle development in vitro. Mol Biol Cell. 12: 1499-1508.

(56) References Cited

OTHER PUBLICATIONS

Torgan CE, et al. (2001) Regulation of myosin heavy chain expression during rat skeletal muscle development in vitro. Mol Biol Cell. 12: 1499-1508.
Torimitsu Kand Kawana A. (1990) Selective growth of sensory nerve fibers on metal oxide pattern in culture. Brain Res Dev Brain Res. 51: 128-131.
Townsend KP and Pratico D. (2005) Novel therapeutic opportunities for Alzheimer's disease: focus on nonsteroidal anti-inflammatory drugs. FASEB J.
Tung L and Cysyk J. (2007) Imaging fibrillation/defibrillation in a dish. J Electrocardiol. 40: S62-S65.
Tung L and Zhang YB. (2006) Optical imaging of arrhythmias in tissue culture. J Electrocardiol. 39: S2-S6.
Uhm CS, et al. (2001) Synapse-forming axons and recombinant agrin induce microprocess formation on myotubes. J Neurosci. 21: 9678-9689.
Ullian EM, et al. (2004) Schwann cells and astrocytes induce synapse formation by spinal motor neurons in culture. Mol Cell Neurosci. 25: 241-251.
Umbach JA, et al. (2012) Functional neuromuscular junctions formed by embryonic stem cell-derived motor neurons. PLoS One. 7: e36049.
Urakami H and Chiu A Y. (1990) A monoclonal antibody that recognizes somatic motor neurons in the mature rat nervous system. J Neurosci. 10: 620-630.
Urazaev AK, et al. (1995) Muscle NMDA receptors regulate the resting membrane potential through NO-synthase. Physiol Res. 44: 205-20.
Vakakis N, et al. (1995) In vitro myoblast to myotube transformations in the presence ofleukemia inhibitory factor. Neurochem Int. 27: 329-335.
Valentin JP, et al. (2004) Review of the predictive value of the Langendorff heart model (Screenit system) in assessing the proarrhythmic potential of drugs. J Pharmacol Toxicol Methods. 49: 171-181.
van de Ven C, et al. (2007) The potential of umbilical cord blood multipotent stem cells for nonhematopoietic tissue and cell regeneration. Exp Hematol. 35:1753-1765.
van der Valk J, et al. (2010) Optimization of chemically defined cell culture media—replacing fetal bovine serum in mammalian in vitro methods. Toxicol In Vitro. 24: 1053-1063.
van Rijen HV, et al. (2006) Connexins and cardiac arrhythmias. Adv Cardiol. 42:150-160.
van Soest PF and Kits KS. (1998) Conopressin affects excitability, firing, and action potential shape through stimulation of transient and persistent inward currents in mulluscan neurons. J Neurophysiol. 79: 1619-1632.
Vandenburgh HH, et al. (1991) Computer aided mechanogenesis of skeletal muscle organs from single cells in vitro. FASEB J. 5: 2860-2867.
Vandenburgh HH, et al. (1996) Tissue engineered skeletal muscle organoids for reversible gene therapy. Hum Gene Ther. 7: 2195-2200.
Vandenburgh HH, et al. (2008) A drug screening platform based on the contractility of tissue engineered muscle. Muscle Nerve. 37: 438-447.
Vandenburgh HH, et al. (2009) Automated drug screening with contractile muscle tissue engineered from dystrophic myoblasts. FASEB J. 23: 3325-3334.
Vandenburgh HH. (1988) A computerized mechanical cell stimulator for tissue A888. culture: Effects on skeletal muscle organogenesis. In Vitro Cell Dev Biol. 24:609-619.
Varghese K, et al. (2009) Regeneration and characterization of adult mouse A889. hippocampal neurons in a defined in vitro system. J N eurosci Methods. 177: 51-59.
Varghese K, et al. (2010) A new target for amyloid beta toxicity validated by standard and high-throughput electrophysiologv. PLoS One. 5: e8643.

Vargo TG, et al. (1992) Monolayer Chemical Lithography and Characterization of Fluoropolymer Films. Langmuir. 8: 130-1.
Vartanian T, et al. (1988) Oligodendrocyte substratum adhesion modulates expression of adenylate cyclase-linked receptors. Proc Natl Acad Sci US A. 85:939-943.
Ventimiglia R, et a. (1987) Localization of beta-adrenergic receptors on differentiated cells of the central nervous system in culture. Proc Natl Acad Sci USA. 84: 5073-507.
Vidarsson H, et al. (2010) Differentiation of human embryonic stem cells to cardiomyocytes for in vitro and in vivo applications. Stem Cell Rev. 6: 108-120.
Viravaidya K and Shuler ML. (2004) Incorporation of 3T3-LI cells to mimic bioaccumulation in a microscale cell culture analog device for toxicity studies. Biotechnol Prog. 20: 590-597.
Vogel V and Sheetz M. (2006) Local force and geometry sensing regulate cell functions. Nat Rev Mol Cell Biol. 7: 265-275.
Vogel Z and Daniels MP. (1976) Ultrastructure of acetylcholine receptor clusters on cultured muscle fibers. J Cell Biol. 69: 501-507.
Waataja JJ, et al. (2008) Excitotoxic loss of post-synaptic sites is distinct temporally and mechanistically from neuronal death. J Neurochem. 104: 364-375.
Waggoner PS and Craighead HG. (2007) Micro- and nanomechanical sensors for environmental, chemical, and biological detection. Lab Chip. 7: 1238-1255.
Wagner I, et al. (2013) A dynamic multi-organ-chip for long-term cultivation and substance testing proven by 3D human liver and skin tissue co-culture. Lab Chip. 13: 3538-3547.
Wakatsuki T, et al. (2004) Phenotypic screening for pharmaceuticals using tissue constructs. Curr Pharm Biotechnol. 5: 181-189.
Walro JM and Kucera J. (1999) Why adult mammalian intrafusal and extrafusal fibers contain different myosin heavy-chain isoforms. Trends Neurosci. 22: 180-184.
Walsh DM and Selkoe DJ. (2007) A beta oligomers—a decade of discovery. J N eurochem. 101: 1172-1184.
Walsh K, et al. (2005) Human central nervous system tissue culture: a historical review and examination ofrecent advances. Neurobiol Dis. 18: 2-18.
Wang HW, et al. (2002) Soluble oligomers of beta amyloid (1-42) inhibit long-term potentiation but not long-term depression in rat dentate gyrus. Brain Res. 924: 133-140.
Wang P, et al. (2005) Defective neuromuscular synapses in mice lacking amyloid precursor protein (APP) and APP-Like protein 2. J Neurosci. 25: 1219-1225.
Wang X, et al. (2008) Effects of interleukin-6, leukemia inhibitory factor, and ciliary neurotrophic factor on the proliferation and differentiation of adult human myoblasts. Cell Mol Neurobiol. 28: 113-124.
Ward JH, et al. (2001) Micropatteming of biomedical polymer surfaces by novel UV polymerization techniques. J Biomed Mater Res. 56: 351-360.
Warf BC, et al. (1991) Evidence for the ventral origin of oligodendrocyte precursors in the rat spinal cord. J Neurosci. 11: 2477-2488.
Wende AR, et al. (2007) A Role for the Transcriptional Coactivator PGC-1 alpha in Muscle Refueling. J Biol Chem. 282: 36642-36651.
Wesierska-Gadek J, et al. (2003) Dual action of cyclin-dependent kinase inhibitors: induction of cell cycle arrest and apoptosis. A comparison of the effects exerted by roscovitine and cisplatin. Pol J Pharmacol. 55: 895-902.
White SM and Claycomb WC. (2005) Embryonic stem cells form an organized, functional cardiac conduction system in vitro. Am J Physiol Heart Circ Physiol. 288: H670-H679.
Wilson K, et al. (2006) Reflex-arc on a chip: An in silico cell culture analogue. NSTI-Nanotech. 2: 297-300.
Wilson K, et al. (2007) Integration of Functional Myotubes with a Bio-MEMS Device for Non-Invasive Interrogation. Lab Chip. 7: 920-922.
Wilson K, et al. (2010) Measurement of contractile stress generated by cultured rat muscle on silicon cantilevers for toxin detection and muscle performance enhancement. PLoS One. 5: e11042.
Wilson K, et al. (2011) Direct patterning of coplanar polyethylene glycol alkylsilane monolayers by deep-ultraviolet photolithography as a general method for high fidelity, long-term cell patterning and culture. J Vac Sci Technol B Nanotechnol Microelectron. 29: 21020.

(56) References Cited

OTHER PUBLICATIONS

Windebank AJ, et al. (1985) Myelination determines the caliber of dorsal root ganglion neurons in culture. J Neurosci. 5: 1563-1569.
Wink T, et al. (1997) Self-assembled Monolayers for Biosensors. Analyst. 122:R43-R50.
Winslow RL, et al. (2005) Using models of the myocyte for functional interpretation of cardiac proteomic data. J Physiol. 563: 73-81.
Wise KD, et al. (2004) Wireless Implantable Microsystems: High-Density Electronic Interfaces to the Nervous System. Proceedings of the IEEE. 92: 76-97.
Witzemann V. (2006) Development of the neuromuscular junction. Cell Tissue Res. 326: 263-271.
Wong ROL. (1998) Calcium imaging and multielectrode recordings of global patterns of activity in the developing nervous system. Histochem J. 30: 217-229.
Wood P, et al. (1990) Studies of the initiation of myelination by Schwann cells. Ann NY Acad Sci. 605: 1-14.
Wright CD, et al. (2008) Nuclear alpha1-adrenergic receptors signal activated ERK localization to caveolae in adult cardiac myocytes. Circ Res. 103: 992-1000.
Wu H, et al. (2010) To build a synapse: signaling pathways in neuromuscular junction assembly. Development. 137: 1017-1033.
Wu P, et al. (2002) Region-specific generation of cholinergic neurons from fetal human neural stem cells grafted in adult rat. Nat Neurosci. 5: 1271-1278.
Wu ZR, et al. (2007) Layer-by-layer assembly of polyelectrolyte films improving cytocompatibility to neural cells. J Biomed Mater Res A. 81: 355-362.
Wyart C, et al. (2002) Constrained synaptic connectivity in functional mammalian neuronal networks grown on patterned surfaces. J Neurosci Methods. 117: 123-131.
Xi J, et al. (2005) Self-assembled microdevices driven by muscle. Nat Mater. 4:180-184.
Xu C, et al. (2006) Growth and differentiation of human embryonic stem cells for cardiac cell replacement therapy. Curr Stem Cell Res Ther. 1: 173-187.
Xu H, et al. (2008) Development of a stable dual cell-line GFP expression system to study estrogenic endocrine disruptors. Biotechnol Bioeng. 101: 1276-1287.
Xu L, et al. (2006) Human neural stem cell grafts ameliorate motor neuron disease in SOD-I transgenic rats. Transplantation. 82: 865-875.
Xu T, et al. (2004) Construction of high-density bacterial colony arrays and patterns by the ink-jet method. Biotechnol Bioeng. 85: 29-33.
Xu T, et al. (2005) Inkjet printing of viable mammalian cells. Biomaterials. 26:93-99.
Xu T, et al. (2006) Viability and electrophysiology of neural cell structures generated by the inkjet printing method. Biomaterials. 27: 3580-3588.
Xu T, et al. (2009) Electrophysiological characterization of embryonic hippocampal neurons cultured in a 3D collagen hydrogel. Biomaterials. 30: 4377-4383.
Yablonka-Reuveni Z. (1995) Development and postnatal regulation of adult myoblasts. Microsc Res Tech. 30: 366-380.
Yan J, et al. (2007) Extensive neuronal differentiation of human neural stem cell grafts in adult rat spinal cord. PLoS Med. 4(2):e39.
Yan J, et al. (2007) Extensive neuronal differentiation of human neural stem cell grafts in adult rat spinal cord. PLoS Med. 4: 318-33.
Yan Z, et al. (2002) Roscovitine: a novel regulator of P/Q-type calcium channels and transmitter release in central neurons. J Physiol. 540: 761-770.
Yang FS, et al. (2005) Curcumin inhibits formation of amyloid beta oligomers and fibrils, binds plaques, and reduces amyloid in vivo. J Biol Chem. 280: 5892-5901.
Yang J, et al. (2006) Synthesis and evaluation of poly(diol citrate) biodegradable elastomers. Biomaterials. 27: 1889-1898.
Yang L, et al. (2007) Increased asynchronous release and aberrant calcium channel activation in amyloid precursor protein deficient neuromuscular synapses. Neuroscience. 149: 768-778.
Yang LX, et al. (2004) Glia cell line-derived neurotrophic factor regulates the distribution of acetylcholine receptors in mouse primary skeletal muscle cells. Neuroscience. 128: 497-509.
Yang SY, et al. (2003) New class of ultrathin, highly cell-adhesion-resistant polyelectrolyte multilayers with micropatterning capabilities. Biomacromolecules. 4: 987-994.
Yang Y, et al. (2003) Neuronal cell death is preceded by cell cycle events at all stages of Alzheimer's disease. J Neurosci. 23: 2557-2563.
Yang Z, et al. (1999) Protein Interactions with Poly(ethylene glycol) Self-Assembled Monolayers on Glass Substrates: Diffusion and Adsorption. Langmuir. 15: 8405-8411.
Yankner BA. (1996) Mechanisms of neuronal degeneration in Alzheimer's disease. Neuron. 16: 921-932.
Yap FL and Zhang Y. (2007) Protein and cell micropatterning and its integration with micro/nanoparticles assembly. Biosens Bioelectron. 22: 775-788.
Yasuda SI, et al. (2001) A novel method to study contraction characteristics of a single cardiac myocyte using carbon fibers. Am J Physiol Heart Circ Physiol. 281: H1442-H1446.
Yeung CK, et al. (2007) Drug profiling using planar microelectrode arrays. Anal Bioanal Chem. 387: 2673-2680.
Yin SH, et al. (2005) Measuring single cardiac myocyte contractile force via moving a magnetic bead. Biophys J. 88: 1489-1495.
Zhao BL, et al. (1989) Scavenging effect of extracts of green tea and natural antioxidants on active oxygen radicals. Cell Biophys. 14: 175-185.
Zhou L, et al. (2005) Mechanistic model of cardiac energy metabolism predicts localization of glycolysis to cytosolic subdomain during ischemic. Am J Physiol Heart Circ Physiol. 288: H2400-H2411.
Zhou Z, et al. (1999) Block of HERG potassium channels by the antihistamine astemizole and its metabolites desmethylastemizole and norastemizole. J Cardiovasc Electrophysiol. 10: 836-843.
Zimmermann WH, et al. (2000) Three-dimensional engineered heart tissue from neonatal rat cardiac myocytes. Biotechnol Bioeng. 68: 106-114.
Zimmermann WH, et al. (2002) Tissue Engineering of a Differentiated Cardiac Muscle Construct. Circ Res. 90: 223-230.
Zorzano A, et al. (2003) Intracellular signals involved in the effects of insulin-like growth factors and neuregulins on myofibre formation. Cell Signal. 15: 141-149.
Zurn AD, et al. (1996) Combined effects of GDNF, BDNF, and CNTF on motoneuron differentiation in vitro. J Neurosci Res. 44: 133-141.
Zweigerdt R, et al. (2003) Generation of confluent cardiomyocyte monolayers derived from embryonic stem cells in suspension: a cell source for new therapies and screening strategies. Cytotherapy. 5: 399-413.

\* cited by examiner

METHOD FOR CULTURING SKELETAL MUSCLE FOR TISSUE ENGINEERING

RELATED APPLICATION

This application is a continuation of U.S. application Ser. No. 12/765,399, filed Apr. 22, 2010, which claims priority to U.S. Provisional Application No. 61/171,968, filed Apr 23, 2009, which are hereby incorporated by reference in their entirety.

STATEMENT OF GOVERNMENT RIGHTS

This invention was made with Government support, under contract/grant number R01 NS050452 awarded by the National Institutes of Health. The Government has certain rights in this invention.

FIELD OF THE INVENTION

The present invention relates to the field of tissue engineering and, more particularly, to a system and method of extending the in vitro useful life of a culture of muscle cells.

BACKGROUND OF THE INVENTION

Skeletal muscle differentiation and maturation is a complex process involving the synergy of different growth factors and hormones interacting over a broad time period [1-11]. The differentiation process is further complicated by neuronal innervation, where neuron to muscle cell signaling can regulate myosin heavy chain (MHC) gene expression and acetylcholine receptor clustering [12-18]. Consequently, understanding of the role of the growth factors, hormones and cellular interactions in skeletal muscle differentiation would be a key step in generating physiologically relevant tissue engineering constructs, developing advanced strategies for regenerative medicine and integrating functional skeletal muscle with bio-hybrid MEMS devices for non-invasive interrogation in high-throughput screening technologies.

In order for skeletal muscle myotubes developed in vitro to be useful in tissue engineering applications, they must exhibit as many of the functional characteristics of in vivo skeletal muscle fibers as possible. During muscle fiber development in vivo, several critical structural changes occur that indicate functional maturation of the extrafusal myotubes. These changes include sarcomere organization, clustering and colocalization of ryanodine (RyR) and dihydropyridine (DHPR) receptors and MHC class switching [19-23]. Each of these structural changes reflects the physiological maturation of the skeletal muscle and is critical for consistent muscular contraction. For example, organization of the contractile proteins myosin and actin into sarcomeric units gives skeletal muscle myotubes organized and structured contraction, a property lacking in smooth muscle. The organization of sarcomeres in skeletal muscle gives rise to anisotropic and isotropic bands of proteins (A and I bands) and gives skeletal muscle a striated appearance. The clustering and colocalization of RyR and DHPR is indicative of transverse tubule (T-tubule) biogenesis and excitation contraction coupling. This developmental step structurally links electrical excitation to the internal contractile system by providing close apposition of DHPR located in the T-tubule and RyR located in the sarcoplasmic reticulum. Finally, a properly functioning skeletal muscle must express the appropriate MHC proteins required for the task it must perform. For example, different muscle fibers express different MHC proteins depending on the rate of contraction and force generation required by the work to be done. Consequently, skeletal muscle fibers change their MHC expression profiles to best meet the requirements of the body as it matures. Without these modifications, an in vitro model of skeletal muscle maturation cannot achieve full physiological relevance.

One approach for identifying the role of specific growth factors and hormones in muscle differentiation is to develop an in vitro model system consisting of a serum-free medium supplemented with the factors of interest. Such a model provides the opportunity to evaluate the role of each factor individually or in combination with others known or believed to be important in skeletal muscle development. For example, the concentration and/or temporal application of medium components in order to influence the maturation of extrafusal fiber or intrafusal fiber subtypes could be easily investigated.

Employing a non-biological growth substrate such as trimethoxy-silylpropyl-diethylenetriamine (DETA) provides an additional measure of control. DETA is a silane molecule that forms a covalently bonded monolayer on glass coverslips, resulting in a uniform, non-hydrophilic surface for cell growth. The use of DETA surfaces is advantageous from a tissue engineering perspective because it can be covalently linked to virtually any hydroxolated surface, it is amenable to patterning using standard photolithography and it promotes long-term cell survival because it is non-digestible by matrix metalloproteinases secreted by the cells [24, 25].

Previously, studies have demonstrated the usefulness of the DETA silane substrate for in vitro culture systems. Interesting features of the DETA silane are that its molecular geometry does not allow for an ordered nanolayer and may partially mimic the three dimensional features of an extracellular matrix, which may be responsible for robust growth of different cell types on this synthetic substrate [24-31]. Additionally, DETA's non-biological nature supports the analysis of ECM proteins secreted by the cell in response to different in vitro conditions.

We earlier developed a defined system that promoted differentiation of different skeletal muscle phenotypes and resulted in the formation of contractile myotubes. This resulted in short-term survival of the myotubes [25, 28]. We also have developed a novel bio-hybrid technology to integrate functional myotubes with cantilever based bio-MEMS devices for the study of muscle physiology, neuromuscular junction formation and bio-robotics applications for use in a model of the stretch reflex arc [32]. More recently, using our defined model system, we have achieved a significant breakthrough by creating mechanosensitive intrafusal myotubes in vitro [33]. The intrafusal fibers differentiated upon addition of neuregulin 1-β-1 to serum-free medium in our defined system. Intrafusal fibers are the myotubes present in the muscle spindle which functions as the sensory receptor of the stretch reflex circuit [16] and combined with extrafusile fibers represent the primary component necessary to reproduce functional muscle function in vitro.

This system has been utilized as a model for different developmental and functional applications, however, further improvements are necessary to enhance the physiological relevance of the skeletal muscle myotubes [32, 33]. Specifically, in order to create a working model of the stretch reflex arc, myotubes are needed that more accurately represent extrafusal fibers in vivo. A more advanced developmental system for skeletal muscle would have applications in basic science research and tissue engineering. In this study, we have demonstrated sarcomere assembly, the development of the excitation-contraction coupling apparatus and myosin heavy chain (MHC) class switching.

The results disclosed herein suggest we have discovered a group of biomolecules that act together as a molecular switch promoting the transition from embryonic to neonatal MHC expression as well as other structural adaptations resulting in the maturation of skeletal muscle in vitro. The discovery of these biomolecular switches will be a powerful tool in regenerative medicine and tissue engineering applications such as skeletal muscle tissue grafts. It should also be useful in higher content high-throughput screening technology.

SUMMARY OF THE INVENTION

With the foregoing in mind, the present invention advantageously provides a method of culturing mammalian muscle cells. The method of the invention includes preparing one or more carriers coated with a covalently bonded monolayer of trimethoxy-silylpropyl-diethylenetriamine (DETA). This is followed by verifying DETA monolayer formation by one or more associated optical parameters. The method continues by suspending isolated fetal rat skeletal muscle cells in serum-free medium according to medium composition 1, as set forth below in further detail, then plating the suspended cells onto the prepared carriers at a predetermined density. The method then calls for leaving the carriers undisturbed while the plated cells adhere to the DETA monolayer and covering the carriers with a mixture of medium composition 1 and medium composition 2, both as described below. Finally, the method ends by incubating the carriers.

In the method, the one or more carriers typically comprise glass cover slips. Those of skill in the art should understand that verifying is accomplished by an optical contact angle goniometer in the present invention, which may also include verifying by X-ray photoelectron spectroscopy (XPS). In the method, verifying may be accomplished by both an optical contact angle goniometer and by XPS.

Our current cantilever system is designed for force measurements of contracting muscle cells and uses laser optics as a readout system [136]. Alternatively, piezoresistive and piezoelectric approaches are the most widely applied techniques for measuring stress applied on microcantilevers [137] and could be easily adapted to the present invention by those of ordinary skill in the art. The advantage is that the mechanical device and the read our electronics can be implemented in the same integrated circuit. Replacing the optical readout with piezoelements will reduce the size and complexity of our current cantilever system.

Those skilled in the art will know that piezoelectricity is the ability of certain materials (crystals and certain ceramics) to generate an electric potential in response to applied mechanical stress [132]. The piezoelectric effect is used in various sensors to measure stresses or geometrical deformations in various mechanical devices. The reverse piezoelectric effect turns piezoelectric materials into actuators, when an external voltage is applied to the crystal [133]. Piezoelectric materials are e.g. quartz, bone, sodium tungstate, zinc oxide, or lead zirconate titanate (PZT) [134]. A similar effect is the piezoresistive phenomenon. When subjected to mechanical stress, these materials change their resistivity [135].

Culture aspects of the method include wherein plating the muscle cells is at a density of approximately from 700 to 1000 cells/mm2. Then, leaving the carriers undisturbed continues for approximately one hour and incubating is effected under physiologic conditions and may best be accomplished at approximately 37° C. in an air atmosphere with about 5% $CO_2$ and 85% humidity. The culture is then covered with a mixture of approximately equal volumes of medium composition 1 and medium composition 2. Preferably, an initial complete change of the medium covering the carriers is accomplished by substituting NBactiv4® medium during incubation. Moreover, after the initial complete change of medium, changing every three days more than half of the medium covering the carriers is preferred and it is most preferred changing every three days approximately three quarters of the medium covering the carriers.

Another embodiment of the present invention includes a method of culturing mammalian muscle cells which comprises allowing mammalian fetal muscle cells suspended in medium according to composition 1to adhere to a monolayer of covalently bonded DETA formed on an underlying carrier surface and incubating the adhered cells covered in a mixture of approximately equal volumes of medium composition 1 and medium composition 2.

In the methods of the invention, the mammalian fetal muscle cells may comprise fetal rat cells and the underlying carrier surface may comprise a glass cover slip. Incubating is preferably under physiological conditions, typically at approximately 37° C. in an atmosphere of air with about 5% $CO_2$ and 85% humidity.

In the alternate embodiment of the invention, the method includes changing the covering medium to NBactiv4®, preferably after approximately four days of incubation. Thereafter, the method calls for changing every three days more than half of the medium covering the carriers and preferably about three quarters of the medium covering the carriers.

Also part of the invention is a new cell culture medium composition which includes NBactiv4®, an antibiotic-antimycotic composition, cholesterol, human TNF-alpha, PDGF BB, vasoactive intestinal peptides, insulin-like growth factor 1, NAP, r-Apolipoprotein E2, purified mouse Laminin, beta amyloid, human tenascin-C protein, rr-Sonic hedgehog Shh N-terminal, and rr-Agrin C terminal. This medium composition may be amplified with G5 supplement, VEGF, acidic fibroblast growth factor, heparin sulphate, LIF, rat plasma Vitronectin, CNTF, GNDF, NT-3, NT-4, BDNF and CT-1.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Materials and Methods

Surface Modification and Characterization

Glass coverslips (Thomas Scientific 6661F52, 22×22 mm No. 1) were cleaned using an $O_2$ plasma cleaner (Harrick PDC-32G) for 20 minutes at 100 mTorr. The DETA (United Chemical Technologies Inc. T2910KG) films were formed by the reaction of the cleaned glass surface with a 0.1% (v/v) mixture of the organosilane in freshly distilled toluene (Fisher T2904). The DETA coated coverslips were then heated to approximately QQ 100° C., rinsed with toluene, reheated to approximately 100° C., and then oven dried [28]. Surfaces were characterized by contact angle measurements using an optical contact angle goniometer (KSV Instruments, Cam 200) and by X-ray photoelectron spectroscopy (XPS) (Kratos Axis 165). XPS survey scans, as well as high-resolution N1s and C1s scans utilizing monochromatic Al Kα excitation were obtained [28].

Skeletal Muscle Culture and Serum Free Medium

Figure 1:
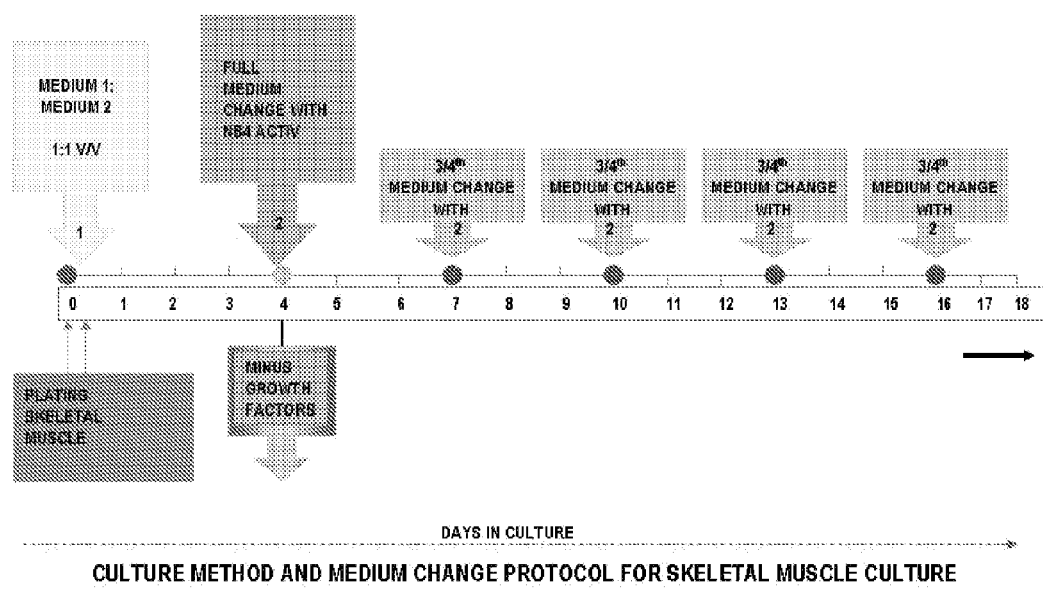
FIG. 1. is a schematic diagram of a culture protocol according to an embodiment of the present invention.

The skeletal muscle was dissected from the thighs of the hind limbs of fetal rats (17-18 days old). The tissue was collected in a sterile 15 mL centrifuge tube containing 1 mL of phosphate-buffered saline (calcium- and magnesium-free) (Gibco 14200075). The tissue was enzymatically dissociated using 2 mL of 0.05% of trypsin-EDTA (Gibco 25300054) solution for 30 minutes in a 37° C. water bath at 50 rpm. After 30 minutes the trypsin solution was removed and 4 mL of Hibernate E +10% fetal bovine serum (Gibco 16000044) was added to terminate the trypsin reaction. The tissue was then mechanically triturated with the supernatant being transferred to a 15 mL centrifuge tube. The same process was repeated two times by adding 2 mL of L15 +10% FBS each time. The 6 mL cell suspension obtained after mechanical trituration was suspended on a 2 mL, 4% BSA (Sigma A3059) (prepared in L15 medium) cushion and centrifuged at 300g for 10 minutes at 4° C. The pellet obtained was washed 5 times with L15 medium then resuspended in 10 mL of L15 and plated in 100mm uncoated dishes for 30 minutes. The non-attached cells were removed and then centrifuged on a 4% BSA cushion [28]. The pellet was resuspended in serum-free medium according to the protocol illustrated in FIG. 1 and plated on the coverslips at a density of 700-1000 cells/mm². The serum-free medium containing different growth factors and hormones was added to the culture dish after one hour. The final medium was prepared by mixing medium one (Table 1) and medium two (Table 2) in a 1:1 v/v ratio. FIG. 1 indicates the flowchart of the culture protocol. Tables 1 and 2 indicated the growth factor and hormone supplement compositions of medium one and medium two. The cells were maintained in a 5% $CO_2$ incubator (relative humidity 85%). The full medium was replaced after four days with NBactiv4® medium according to the protocol in FIG. 1. Thereafter three-fourth of the medium was changed every three days with NBactiv4®.

NbActiv4® (available from BrainBits LLC) comprises all of the ingredients in Neurobasal™, B-27™, and Gluta-MAX™. NbActiv4® also comprises creatine, estrogen, and cholesterol.

Immunocytochemistry of Skeletal Muscle Myotubes

Coverslips were prepared for immunocytochemical analysis as previously described. Briefly, coverslips were rinsed with PBS, fixed in −20☐ C methanol for 5-7 min, washed in PBS, incubated in PBS supplemented with 1% BSA and 0.05% saponin (permeabilization solution) for 10 minutes, and blocked for 2 h with 10% goat serum and 1% BSA. Cells were incubated overnight with primary antibodies against embryonic myosin heavy chain (F1.652) (dilution>1:5), neonatal myosin heavy chain (N3.36) (1:5) (Developmental Studies Hybridoma Bank), ryanodine receptor (AB9078, Millipore) (1:500) and dihydropyridine binding complex (α1-Subunit) (MAB 4270, Millipore) (1:500) diluted in the blocking solution. Cells were washed with PBS and incubated with the appropriate secondary antibodies for two hours in PBS. After two hours the coverslips were rinsed with PBS and mounted on glass slides and evaluated using confocal microscopy [25, 28, 31].

AChR Labeling of Myotubes

AChRs were labeled as described previously by incubating cultures with 5×10-8 M of α-bungarotoxin, Alexa Fluor® 488 conjugate (B-13422; Invitrogen) for 1.5 h at 37° C. [12, 31]. Following incubation in α-bungarotoxin, the cultures were fixed as above for subsequent staining with embryonic myosin heavy chain (F1.652) antibodies.

Patch Clamp Electrophysiology of the Myotubes

Whole-cell patch clamp recordings were performed in a recording chamber located on the stage of a Zeiss Axioscope 2FS Plus upright microscope as described previously [25, 33]. The chamber was continuously perfused (2 ml/min) with the extracellular solution (Leibovitz medium, 35° C.). Patch pipettes were prepared from borosilicate glass (BF150-86-10; Sutter, Novato, Calif.) with a Sutter P97 pipette puller and filled with intracellular solution (K-gluconate 140 mM, EGTA 1 mM, $MgCl_2$ 2 mM, $Na_2ATP$ 2 mM, phosphocreatine 5 mM, phosphocreatine kinase 2.4 mM, Hepes 10 mM; pH=7.2). The resistance of the electrodes was 6-8MΩ. Voltage clamp and current clamp experiments were performed with a Multiclamp 700A amplifier (Axon Laboratories, Union City, Calif.). Signals were filtered at 2 kHz and digitized at 20 kHz with an Axon Digidata 1322A interface. Data recording and analysis were done with pClamp 8 software (Axon Laboratories). Membrane potentials were corrected by subtraction of a 15 mV tip potential, which was calculated using Axon's pClamp 8 program. Sodium and potassium currents were measured in voltage clamp mode using voltage steps from a −85 mV holding potential. Action potentials were evoked with 1 second depolarizing current injections from a -85 mV holding potential [25, 28].

Results

DETA Surface Modification and Characterization

Static contact angle and XPS analysis was used for the validation of the surface modifications and for monitoring the quality of the surfaces. Stable contact angles (40.64±2.9/ mean±SD) throughout the study indicated high reproducibility and quality of the DETA surfaces and were similar to previously published results [24, 25, 28, 29, 31]. Based on the ratio of the N (401 and 399 eV) and the Si 2p3/2 peaks, XPS measurements indicated that a reaction-site limited monolayer of DETA was formed on the coverslips [35].

Development of the Serum Free Medium Formulation and Culture Timeline for Long-Term Survival and Maturation of Myotubes The serum free medium composition was developed empirically. The final medium is derived from two different medium compositions described in Tables 1 and 2. Table 1 constitutes the same medium composition used previously for a motoneuron-muscle co-culture and adult spinal cord neurons culture [26, 27, 30, 31]. Table 2 is composed of twelve additional factors that had been shown to promote skeletal muscle maturation and neuromuscular junction formation separately. The final medium was prepared by mixing these two media in a 1:1 v/v ratio. After first 4 days of culture the whole medium was replaced with NBactiv4® medium [34]. hereafter, every three days three-fourth medium was changed with NBactiv4®. The culture technique has been illustrated in the flowchart (FIG. 1).

Figure 2:
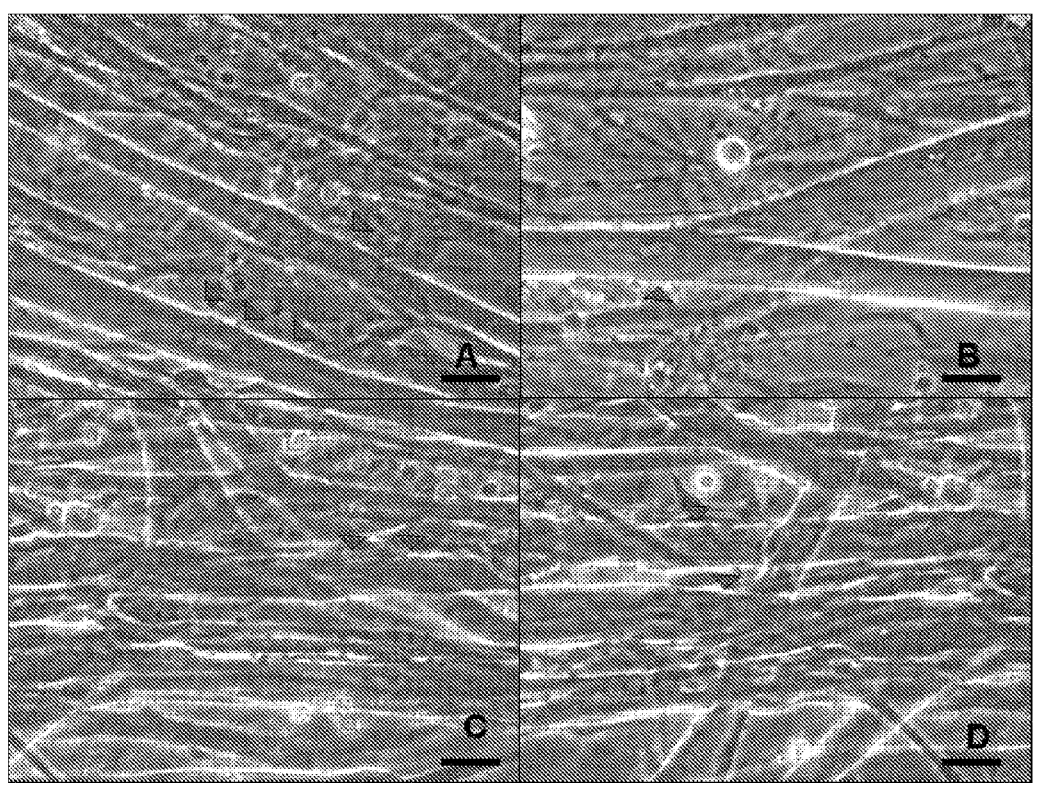
FIG. 2 A, B, C and D provide phase pictures of 50 day old myotubes in culture; red arrows showing characteristic striations in most of the myotubes; scale bar equals 75 µm.

Using this new medium formulation and timeline, myotubes were successfully cultured for more than 50 days. FIG. 2 indicates 50 days old myotubes in culture. As the myotubes aged and grew they began to form the characteristic anisotropic (A band) and isotropic (I band) banding pattern observed with in vivo muscle fibers [22, 23]. This banding pattern is caused by differential light diffraction due to the organization of myofibril proteins forming sarcomeres within the myotubes [22, 23]. The arrowheads in the images (FIG. 2A-D) indicate myotubes where sarcomeric organization has occurred and is visualized by the appearance of A and I bands.

Myotube Expression of Fetal Myosin Heavy Chain

Figure 3:
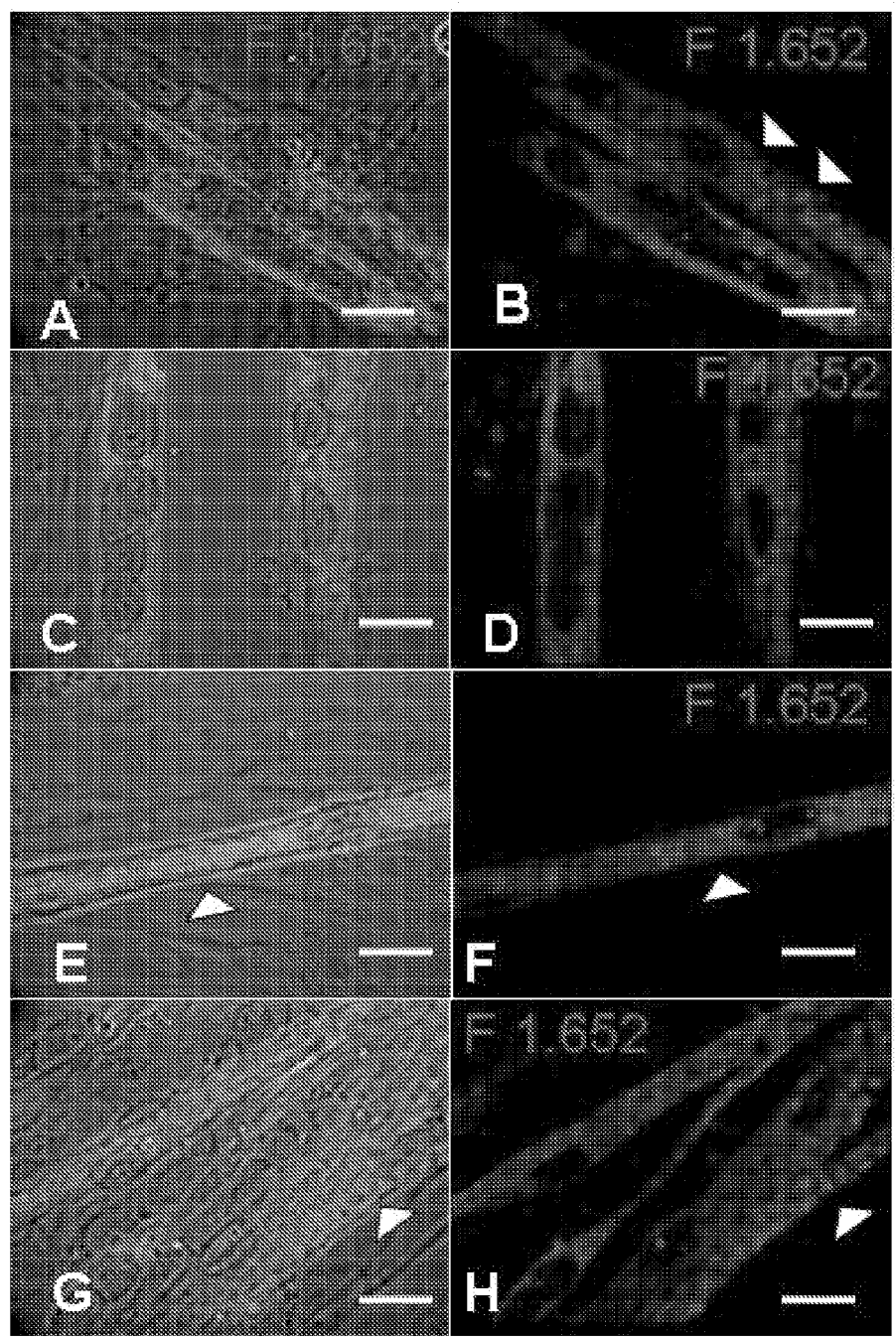
FIG. 3 shows myotubes stained with antibodies against embryonic myosin heavy chain (F 1.652) proteins at day 50; scale bar is 75 µm; A) panel showing phase+fluorescence picture of the myotubes; B) another view of panel A but observed only under fluorescence; white arrows showing the striations; C) panel showing image of myotubes under phase+fluorescence illumination; D) shows panel C observed only under fluorescence illumination; E) panel showing phase+fluorescence picture of the myotubes (white arrow indicating the striations); F) panel E observed only in fluorescence light (white arrow indicating the striations); G) panel showing phase+fluorescence picture of the myotubes (white arrow indicating the striations); H) panel G observed only under fluorescence light (white arrow indicating the striations)
Figure 4:
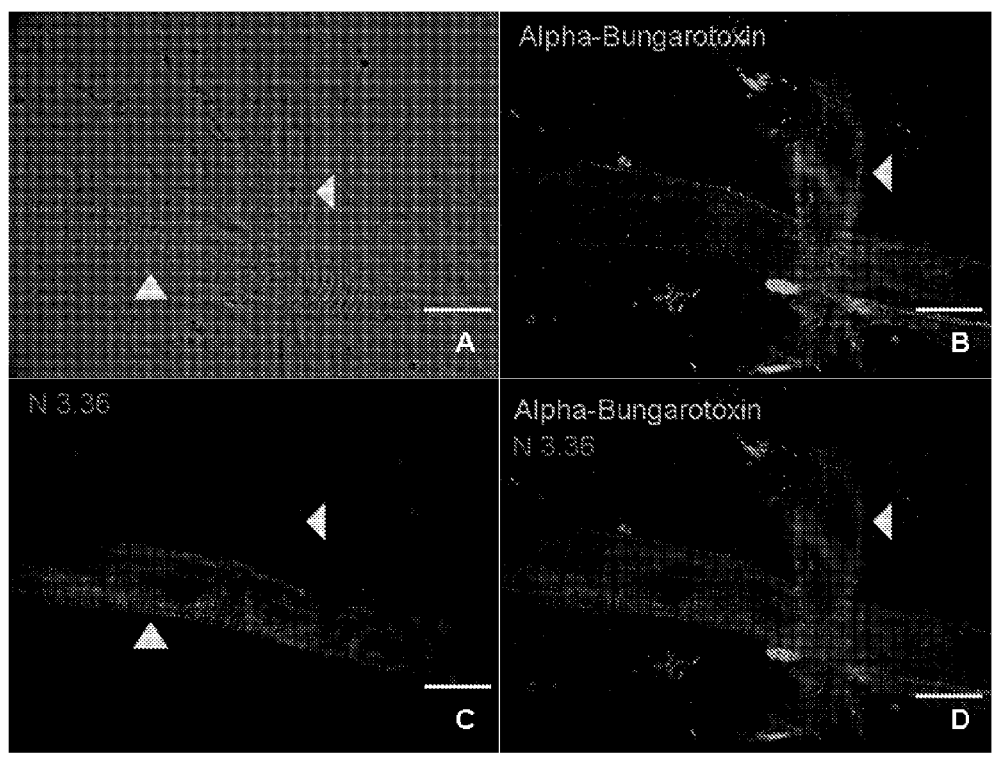
FIG. 4 shows myotubes immunostained with neonatal myosin heavy chain (N3.36) and alpha-bungarotoxin at day 50; scale bar is 75 µm; A) is a phase picture of 2 myotubes indicated by white arrows; B) both the myotubes shown in phase (panel A) have acetylcholine receptor clustering indicated by alpha-bungarotoxin staining; C) only one myotube out of the two seen in panel A stained for N3.36; D) double stained image of panel A with alpha-bungarotoxin and N3.36; E) phase image of 6 myotubes indicated by white arrows; F) all the myotubes shown in phase (panel E) have acetylcholine receptor clustering shown by alpha-bungarotoxin staining; G) none of the myotubes in panel E stained for N3.36; H) I) and J) show differential staining of the myotubes with N3.36; K) L) and M) showing differential staining of the myotubes with N3.36.
Figure 4:
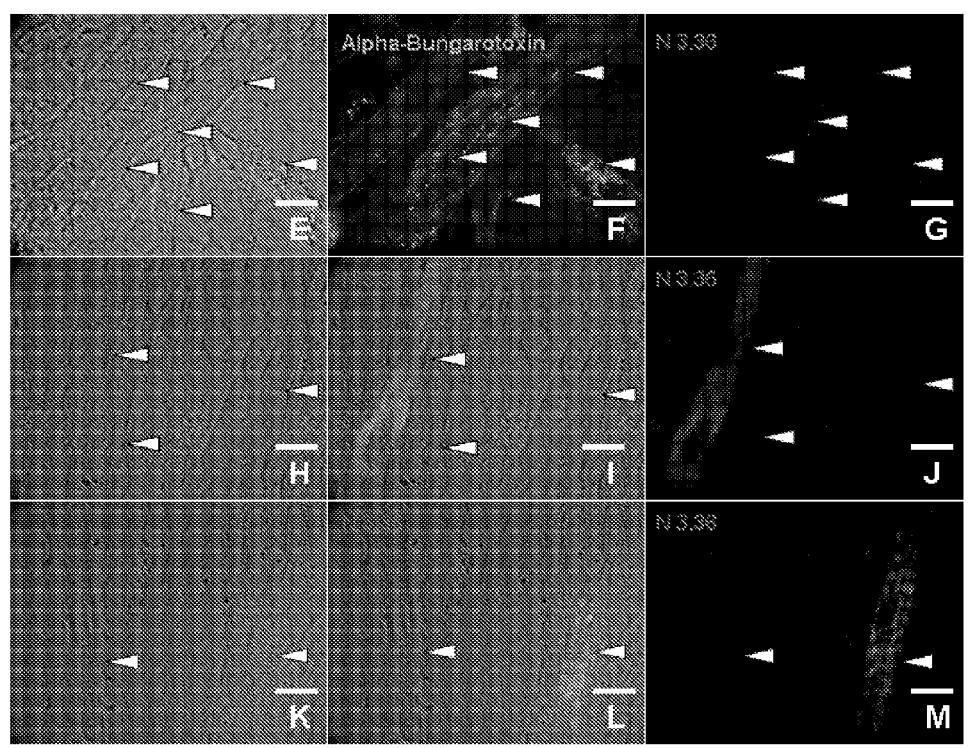

The myotubes formed were evaluated for the expression of fetal MHC to establish a baseline as comparison to our previous results [28]. In FIG. 3, the myotubes phenotypes formed at approximately day 50 in vitro are shown. The myotubes ranged from having clustered nuclei (FIG. 3A-D) to having diffuse nuclear organization (FIG. 3E-H). The arrowheads in the images indicate the characteristic striations.

Differential Expression of Neonatal MHC Protein in the Myotubes

Figure 5:
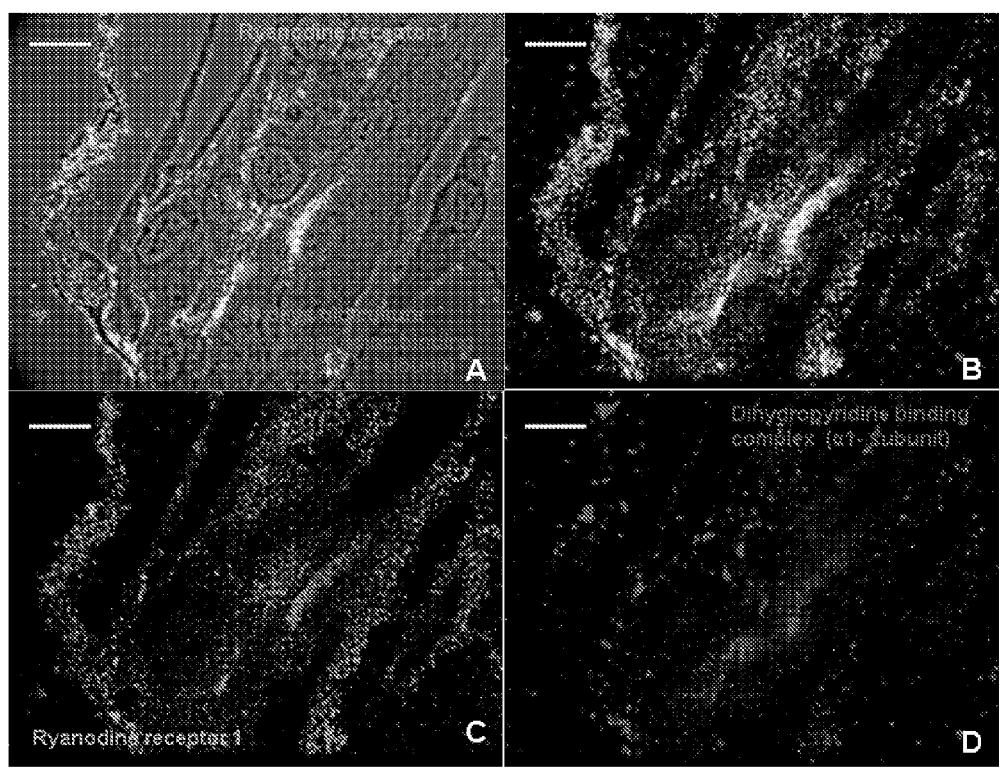
FIG. 5 illustrates ryanodine receptor and DHPR receptor clustering in 30 days old skeletal muscle culture (scale bar 75 µm); A) phase and fluorescent-labeled picture of the myotubes; B) merged fluorescence picture of the ryanodine receptor (green) and DHPR receptor (red) clustering on the myotubes shown in panel A; C) ryanodine receptor (green) on the myotubes shown in panel A; D) DHPR receptors on the myotubes shown in panel A; E) phase and fluorescent-labeled picture of the myotubes; F) merged fluorescent picture of the ryanodine receptor (green) and DHPR receptor (red) clustering on the myotubes (panel E); G) ryanodine receptor (green) on the myotubes (panel E); H) DHPR receptors on the myotubes (panel E); I) phase and fluorescent-labeled picture of the myotubes; J) K) and L) show merged fluorescence pictures of the ryanodine receptor (green) and DHPR receptor (red) clustering on the myotubes (panel I) at three different planes (white arrows indicate the striations and the receptor clustering)
Figure 5:
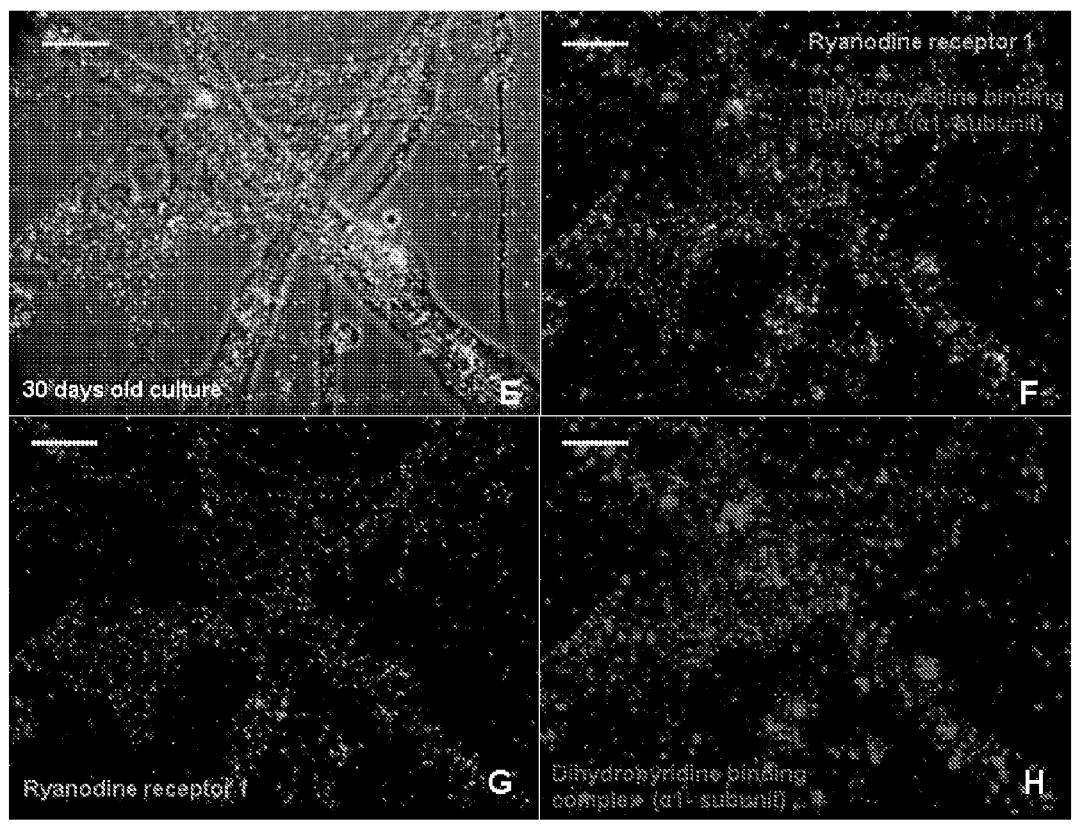
Figure 5:
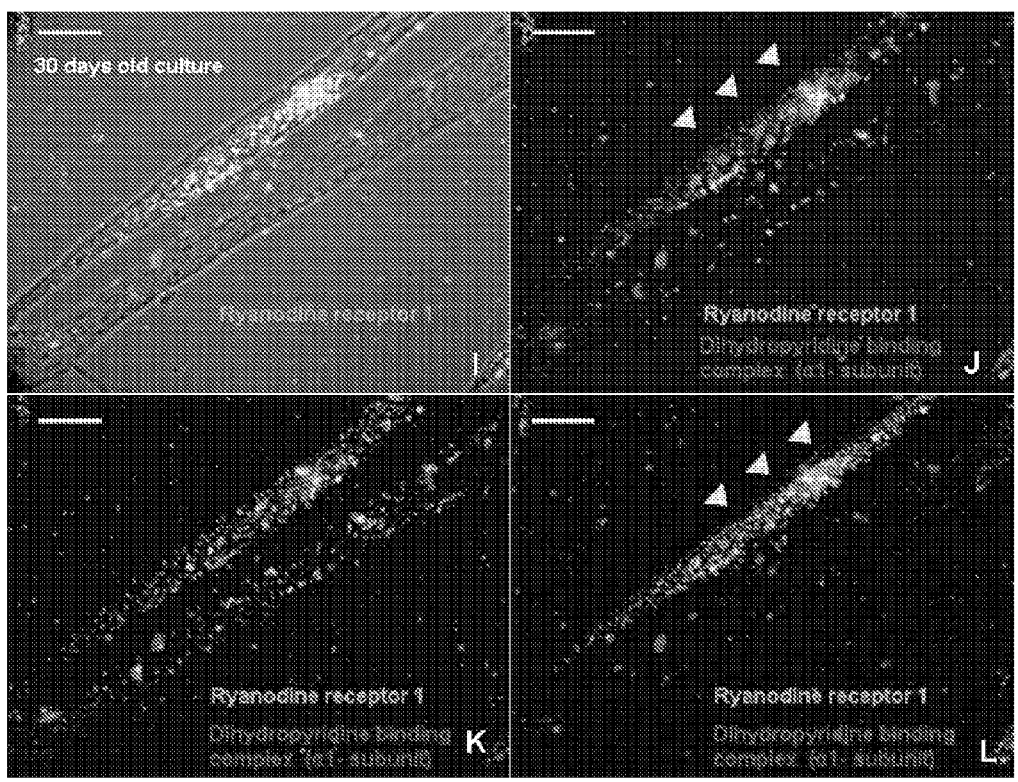
Figure 6:
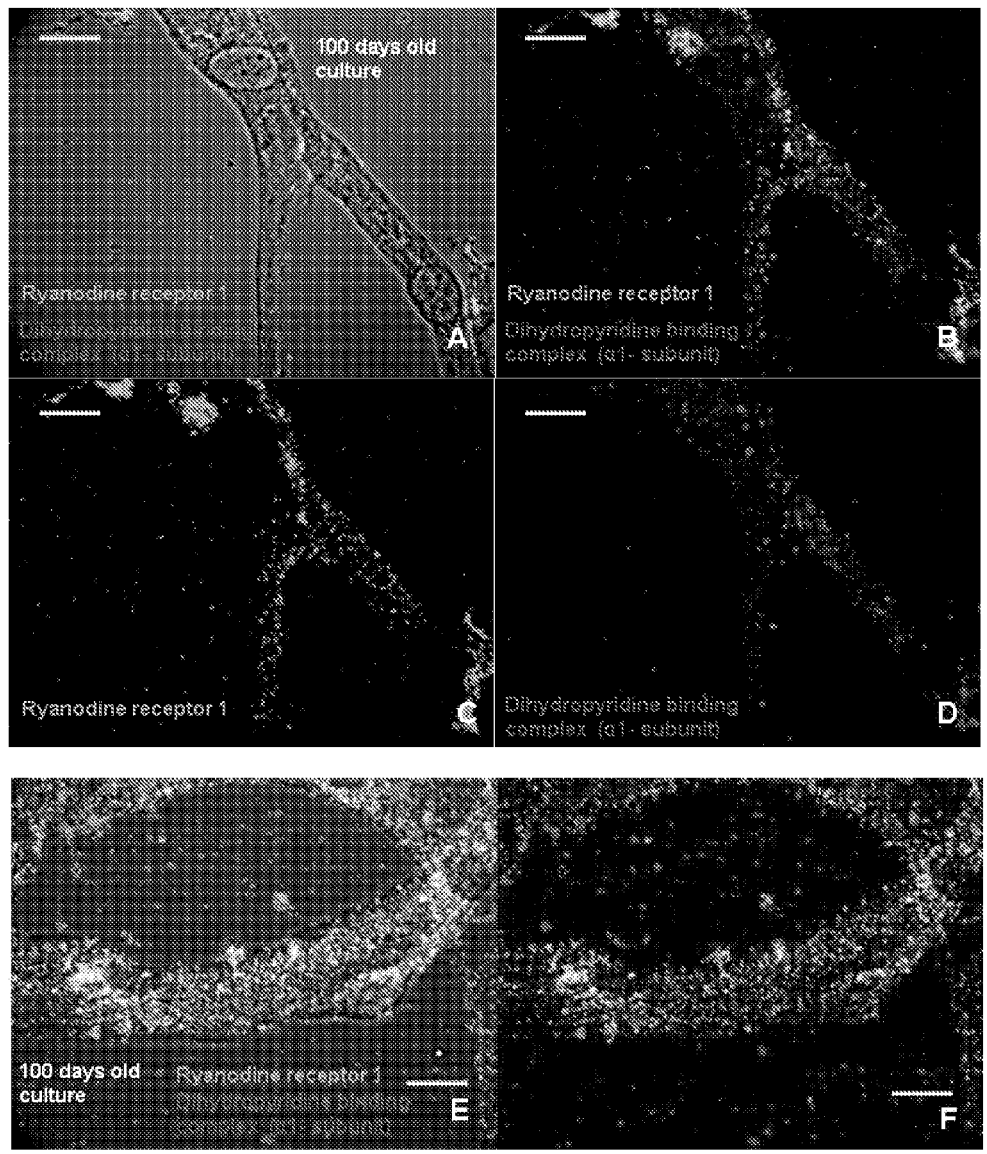
FIG. 6 shows ryanodine receptor and DHPR receptor clustering in 100 days old skeletal muscle culture (scale bar: 75 µm); A) shows phase and fluorescent-labeled picture of the myotubes; B) is a merged fluorescence picture of the ryanodine receptor (green) and DHPR receptor (Red) clustering on the myotubes (panel A); C) shows ryanodine receptor (green) on the myotubes (panel A); D) shows DHPR receptors on the myotubes (panel A); E and F show views of the same panels at different planes showing the merged fluorescent picture of the ryanodine receptor (green) and DHPR receptor (red) clustering on the myotubes.

In order to determine if the myotubes were maturing in a physiologically relevant way as they aged in vitro, the expression of neonatal MHC protein was evaluated. After approximately 50 days in vitro 25% of the myotubes expressed neonatal MHC (FIG. 4A-M). Additionally, the myotubes were stained for clustering of acetylcholine receptors (AChR) using alpha bungarotoxin (FIG. 5B,F). This clustering of the AChR receptors, induced by the motoneuron protein agrin in vivo, are locations on the myotube where neuromuscular junction formation occurs.

Formation of the Excitation—Contraction Coupling Apparatus

The presence of ryanodine (RyR) receptor and dihydropyridine (DHPR) receptor clusters, as well as their colocalization in vivo, represents the development of excitation-contraction coupling apparatus in skeletal muscle myotubes [19, 21-23]. The clustering of both RyR and DHPR receptors was observed on the myotubes after 30 days in culture (FIG. 5A-D). The clustering and colocalization of the RyR+DHPR clusters was observed with different myotube morphologies (FIG. 5E-L). This functional adaptation illustrated that the medium formulation facilitated not only the structural maturation but also the functional maturation of myotubes in this in vitro system. The clustering of the RyR+DHPR receptors was also observed in the 70 day old myotubes, indicating that the older myotubes maintained their functional integrity (FIG. 6A-F).

Myotube Electrophysiology

Figure 7:
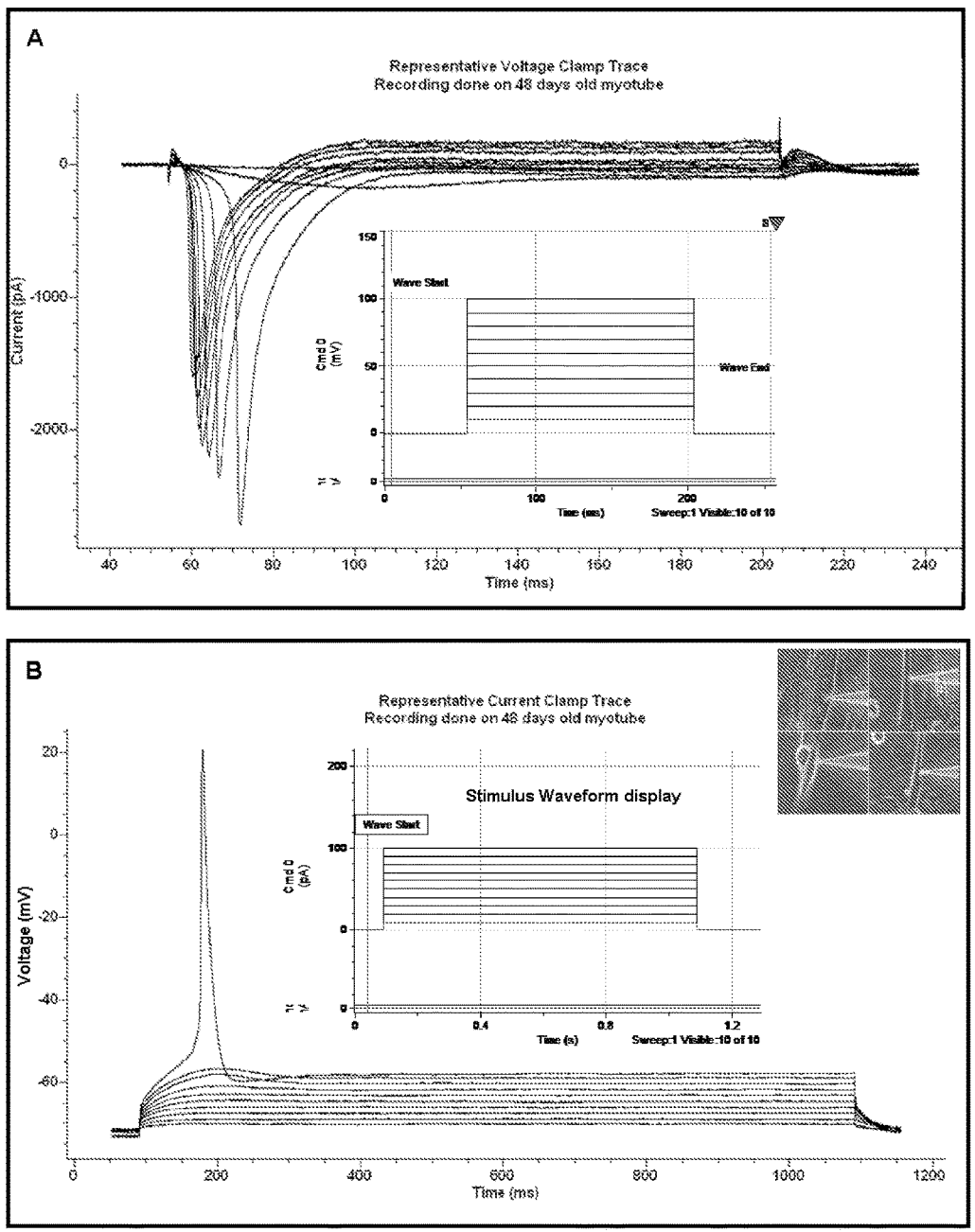
FIG. 7 depicts patch clamp electrophysiology of the myotubes, wherein A shows representative voltage clamp trace obtained after patching a 48 days old myotube in culture; B shows representative current clamp trace of the same myotube for which voltage clamp trace had been obtained (inset showing the picture of patched myotubes).

The myotubes contracted spontaneously in the culture and the contractions began generally by day four and continued throughout the life of the culture. Most of the myotubes expressed functional voltage gated sodium, potassium and calcium ion channels as reported previously [28]. The voltage clamp electrophysiology of the myotubes indicated the inward and outward currents that demonstrate functional sodium and potassium channels (FIG. 7A). The current clamp study indicated the single action potential fired by the myotubes (FIG. 7B).

Discussion

Herein we have documented the development of a system for long-term in vitro functional, skeletal muscle culture. This system was developed in response to a need for more physiologically relevant skeletal muscle myotubes for functional in vitro systems. For our specific research, they were needed for a realistic model of the stretch reflex arc development and to be integrated with bio-MEMS cantilevers for screening appications. The results indicate we achieved three significant structural modifications within the myotubes, causing both the developmental profile and functionality of the fibers to better mimic in vivo physiology. It is believed that this skeletal muscle maturation resulted from modifications to the cell culture technique, a new medium formulation and the use of NBactiv4® as the maintenance medium.

The presently described serum-free medium supplemented with growth factors was developed to support the survival, proliferation and fusion of fetal rat myoblasts into contractile myotubes. The rationale for selecting the growth factors was based on the distribution of their cognate receptors in the developing myotubes in rat fetus [1-11]. Tables 1 and 2 reference the literature where these individual growth factors, hormones and neurotransmitters were observed to support muscle and neuromuscular junction development. The composition in Table 1 is the formulation used for a previously published medium used for motoneuron-muscle co-culture and adult spinal cord neuron culture [26, 27, 30, 31]. Table 2 lists the twelve additional factors we have identified in muscle development and neuromuscular junction formation. The use of NBactiv4® for the maintenance of the cells provided unexpected results in that it significantly improved the survival of the skeletal muscle derived myotubes despite the original development of NBactiv4® for the long-term maintenance and synaptic connectivity of fetal hippocampal neurons in vitro [34].

We observed a ratio of 25% neonatal to 75% embryonic MHC expression of the myotubes, which contrasts with the previous study in which MHC expression was strictly embryonic. We believe that the myotubes matured in this culture system because the long-term survival provided adequate time for the myotubes to respond to the additional growth factors, which activated the necessary signaling pathways to achieve MHC class switching [20]. This suggests that a different growth factor profile could be utilized to activate alternative signaling pathways and drive myotube differentiation down other pathways. For example, the effects of adding steroid hormones like testosterone to the system could be critically examined.

The colocalization of RyR and DHPR clusters in the myotubes indicated the formation of excitation-contraction coupling apparatus and was another indicator of functional maturation in the fibers. Excitation-contraction coupling is the signaling process in muscle by which membrane depolarization causes a rapid elevation of the cytosolic $Ca^{2+}$ generating contractile force [36]. The close proximity of the DHPR and RyR complexes occurs at specialized junctions established between the transverse tubule and sarcoplasmic reticulum (SR) membranes in skeletal muscle myotubes [37]. At these junctions, T-tubule depolarization is coupled to $Ca^{2+}$ release from the SR resulting in muscle contraction [38-40]. This structural adaptation represents a significant functional change due to the fact that excitation-contraction coupling is required for successful extrafusal muscle fiber development as well as neuromuscular junction formation [19, 21-23]. This improved model provides the potential to study excitation-contraction coupling in a defined system as well as myotonic and myasthenic diseases.

Conclusion

The development of sarcomeric structures, the excitation-contraction coupling apparatus and MHC class switching in the skeletal muscle myotubes is a result of the improvements to the model system documented in this research. This improved system along with the new findings support the goal of creating physiologically relevant tissue engineered muscle constructs and puts within reach the goal of functional skeletal muscle grafts. Furthermore, we believe this serum-free culture system will be a powerful tool in developing advanced strategies for regenerative medicine in muscular dystrophies, stretch reflex arc development and integrating skeletal muscle with bio-hybrid prosthetic devices.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES

1. Arnold H H, Winter B. Muscle differentiation: more complexity to the network of myogenic regulators. Curr Opin Genet Dev. 1998 October; 8(5):539-44.
2. Olson E. Activation of muscle-specific transcription by myogenic helix-loop-helix proteins. Symp Soc Exp Biol. 1992; 46:331-41.
3. Olson E N. Interplay between proliferation and differentiation within the myogenic lineage. Dev Biol. 1992 December; 154(2):261-72.
4. Olson E N, Perry W M. MyoD and the paradoxes of myogenesis. Curr Biol. 1992 January; 2(1):35-7.
5. Li L, Olson E N. Regulation of muscle cell growth and differentiation by the MyoD family of helix-loop-helix proteins. Adv Cancer Res. 1992; 58:95-119.
6. Brand T, Butler-Browne G, Fuchtbauer E M, Renkawitz-Pohl R, Brand-Saberi B. EMBO Workshop Report: Molecular genetics of muscle development and neuromuscular diseases Kloster Irsee, Germany, Sep. 26-Oct. 1, 1999. Embo J. 2000 May 2; 19(9):1935-41.
7. Brand-Saberi B. Genetic and epigenetic control of skeletal muscle development. Ann Anat. 2005 July; 187(3):199-207.
8. Brand-Saberi B, Christ B. Genetic and epigenetic control of muscle development in vertebrates. Cell Tissue Res. 1999 April; 296(1):199-212.

9. Scaal M, Bonafede A, Dathe V, Sachs M, Cann G, Christ B, et al. SF/HGF is a mediator between limb patterning and muscle development. Development. 1999 November; 126(21):4885-93.
10. Schwarz J J, Chakraborty T, Martin J, Zhou J M, Olson E N. The basic region of myogenin cooperates with two transcription activation domains to induce muscle-specific transcription. Mol Cell Biol. 1992 January; 12(1): 266-75.
11. Christ B, Brand-Saberi B. Limb muscle development. Int J Dev Biol. 2002; 46(7):905-14.
12. Dutton E K, Uhm C S, Samuelsson S J, Schaffner A E, Fitzgerald S C, Daniels M P. Acetylcholine receptor aggregation at nerve-muscle contacts in mammalian cultures: induction by ventral spinal cord neurons is specific to axons. J Neurosci. 1995 November; 15(11):7401-16.
13. Daniels M P, Lowe B T, Shah S, Ma J, Samuelsson S J, Lugo B, et al. Rodent nerve-muscle cell culture system for studies of neuromuscular junction development: refinements and applications. Microsc Res Tech. 2000 Apr. 1; 49(1):26-37.
14. Uhm C S, Neuhuber B, Lowe B, Crocker V, Daniels M P. Synapse-forming axons and recombinant agrin induce microprocess formation on myotubes. J Neurosci. 2001 Dec. 15; 21(24):9678-89.
15. Oakley R A, Lefcort F B, Clary D O, Reichardt L F, Prevette D, Oppenheim R W, et al. Neurotrophin-3 promotes the differentiation of muscle spindle afferents in the absence of peripheral targets. J Neurosci. 1997 Jun. 1; 17(11):4262-74.
16. Kucera J, Walro J M, Reichler J. Role of nerve and muscle factors in the development of rat muscle spindles. Am J Anat. 1989 October; 186(2):144-60.
17. Kucera J, Walro J. Axotomy induces fusimotor-free muscle spindles in neonatal rats. Neurosci Lett. 1992 Mar. 2; 136(2):216-8.
18. Albert Y, Whitehead J, Eldredge L, Carter J, Gao X, Tourtellotte W G. Transcriptional regulation of myotube fate specification and intrafusal muscle fiber morphogenesis. J Cell Biol. 2005 Apr. 25; 169(2):257-68.
19. Flucher B E, Andrews S B, Daniels M P. Molecular organization of transverse tubule/sarcoplasmic reticulum junctions during development of excitation-contraction coupling in skeletal muscle. Mol Biol Cell. 1994 October; 5(10):1105-18.
20. Torgan C E, Daniels M P. Regulation of myosin heavy chain expression during rat skeletal muscle development in vitro. Mol Biol Cell. 2001 May; 12(5):1499-508.
21. Flucher B E, Morton M E, Froehner S C, Daniels M P. Localization of the alpha 1 and alpha 2 subunits of the dihydropyridine receptor and ankyrin in skeletal muscle triads. Neuron. 1990 September; 5(3):339-51.
22. Flucher B E, Phillips J L, Powell J A, Andrews S B, Daniels M P. Coordinated development of myofibrils, sarcoplasmic reticulum and transverse tubules in normal and dysgenic mouse skeletal muscle, in vivo and in vitro. Dev Biol. 1992 April; 150(2):266-80.
23. Flucher B E, Terasaki M, Chin H M, Beeler T J, Daniels M P. Biogenesis of transverse tubules in skeletal muscle in vitro. Dev Biol. 1991 May; 145(1):77-90.
24. Das M, Molnar P, Gregory C, Riedel L, Jamshidi A, Hickman J J. Long-term culture of embryonic rat cardiomyocytes on an organosilane surface in a serum-free medium. Biomaterials. 2004 November; 25(25):5643-7.
25. Das M, Wilson K, Molnar P, Hickman J J. Differentiation of skeletal muscle and integration of myotubes with silicon microstructures using serum-free medium and a synthetic silane substrate. Nat Protoc. 2007; 2(7):1795-801.
26. Das M, Bhargava N, Bhalkikar A, Kang J F, Hickman J J. Temporal neurotransmitter conditioning restores the functional activity of adult spinal cord neurons in long-term culture. Exp Neurol. 2008 January; 209(1):171-80.
27. Das M, Bhargava N, Gregory C, Riedel L, Molnar P, Hickman J J. Adult rat spinal cord culture on an organosilane surface in a novel serum-free medium. In Vitro Cell Dev Biol Anim. 2005 November-December; 41(10):343-8.
28. Das M, Gregory C A, Molnar P, Riedel L M, Wilson K, Hickman J J. A defined system to allow skeletal muscle differentiation and subsequent integration with silicon microstructures. Biomaterials. 2006 August; 27(24): 4374-80.
29. Das M, Molnar P, Devaraj H, Poeta M, Hickman J J. Electrophysiological and morphological characterization of rat embryonic motoneurons in a defined system. Biotechnol Prog. 2003 November-December; 19(6):1756-61.
30. Das M, Patil S, Bhargava N, Kang J F, Riedel L M, Seal S, et al. Auto-catalytic ceria nanoparticles offer neuroprotection to adult rat spinal cord neurons. Biomaterials. 2007 April; 28(10):1918-25.
31. Das M, Rumsey J W, Gregory C A, Bhargava N, Kang J F, Molnar P, et al. Embryonic motoneuron-skeletal muscle co-culture in a defined system. Neuroscience. 2007 May 11; 146(2):481-8.
32. Wilson K, Molnar P, Hickman J. Integration of functional myotubes with a Bio-MEMS device for non-invasive interrogation. Lab Chip. 2007 July; 7(7):920-2.
33. Rumsey J W, Das M, Kang J F, Wagner R, Molnar P, Hickman J J. Tissue engineering intrafusal fibers: dose- and time-dependent differentiation of nuclear bag fibers in a defined in vitro system using neuregulin 1-beta-1. Biomaterials. 2008 March; 29(8):994-1004.
34. Brewer G J, Boehler M D, Jones T T, Wheeler B C. NbActiv4 medium improvement to Neurobasal/B27 increases neuron synapse densities and network spike rates on multielectrode arrays. J Neurosci Methods. 2008 May 30; 170(2):181-7.
35. Stenger D A, Georger J H, Dulcey C S, Hickman J J, Rudolph A S, Nielsen T B, et al. Coplanar Molecular Assemblies of Aminoalkylsilane and Perfluorinated Alkylsilane—Characterization and Geometric Definition of Mammalian-Cell Adhesion and Growth. J Am Chem Soc. 1992; 114(22):8435-42.
36. Ruegg J. Calcium in muscle activation. Berlin: Springer Verlag; 1988.
37. Franzini-Armstrong C, Protasi F. Ryanodine receptors of striated muscles: a complex channel capable of multiple interactions. Physiol Rev. 1997 July; 77(3):699-729.
38. Ahern C A, Sheridan D C, Cheng W, Mortenson L, Nataraj P, Allen P, et al. Ca2+ current and charge movements in skeletal myotubes promoted by the beta-subunit of the dihydropyridine receptor in the absence of ryanodine receptor type 1. Biophys J. 2003 February; 84(2 Pt 1):942-59.
39. Sheridan D C, Carbonneau L, Ahern C A, Nataraj P, Coronado R. Ca2+-dependent excitation-contraction coupling triggered by the heterologous cardiac/brain DHPR beta2a-subunit in skeletal myotubes. Biophys J. 2003 December; 85(6):3739-57.
40. Sheridan D C, Cheng W, Ahern C A, Mortenson L, Alsammarae D, Vallejo P, et al. Truncation of the carboxyl terminus of the dihydropyridine receptor beta1a subunit promotes Ca2+ dependent excitation-contraction coupling in skeletal myotubes. Biophys J. 2003 January; 84(1):220-37.

41. Brewer G J, Torricelli J R, Evege E K, Price P J. Optimized survival of hippocampal neurons in B27-supplemented Neurobasal, a new serum-free medium combination. J Neurosci Res. 1993 Aug. 1; 35(5):567-76.

42. Alterio J, Courtois Y, Robelin J, Bechet D, Martelly I. Acidic and basic fibroblast growth factor mRNAs are expressed by skeletal muscle satellite cells. Biochem Biophys Res Commun. 1990 Feb. 14; 166(3):1205-12.

43. Clegg C H, Linkhart T A, Olwin B B, Hauschka S D. Growth factor control of skeletal muscle differentiation: commitment to terminal differentiation occurs in G1 phase and is repressed by fibroblast growth factor. J Cell Biol. 1987 August; 105(2):949-56.

44. Bottenstein J E. Advances in vertebrate cell culture methods. Science. 1988 Feb. 12; 239(4841 Pt 2):G42, G8.

45. Bottenstein J E, Hunter S F, Seidel M. CNS neuronal cell line-derived factors regulate gliogenesis in neonatal rat brain cultures. J Neurosci Res. 1988 July; 20(3):291-303.

46. Bottenstein J E. Proliferation of glioma cells in serum-free defined medium. Cancer Treat Rep. 1981; 65 Suppl 2:67-70.

47. Morrow N G, Kraus W E, Moore J W, Williams R S, Swain J L. Increased expression of fibroblast growth factors in a rabbit skeletal muscle model of exercise conditioning. J Clin Invest. 1990 June; 85(6):1816-20.

48. Gonzalez A M, Buscaglia M, Ong M, Baird A. Distribution of basic fibroblast growth factor in the 18-day rat fetus: localization in the basement membranes of diverse tissues. J Cell Biol. 1990 March; 110(3):753-65.

49. Moore J W, Dionne C, Jaye M, Swain J L. The mRNAs encoding acidic FGF, basic FGF and FGF receptor are coordinately downregulated during myogenic differentiation. Development. 1991 March; 111(3):741-8.

50. Anderson J E, Liu L, Kardami E. Distinctive patterns of basic fibroblast growth factor (bFGF) distribution in degenerating and regenerating areas of dystrophic (mdx) striated muscles. Dev Biol. 1991 September; 147(1):96-109.

51. Olwin B B, Rapraeger A. Repression of myogenic differentiation by aFGF, bFGF, and K-FGF is dependent on cellular heparan sulfate. J Cell Biol. 1992 August; 118(3):631-9.

52. Arsic N, Zacchigna S, Zentilin L, Ramirez-Correa G, Pattarini L, Salvi A, et al. Vascular endothelial growth factor stimulates skeletal muscle regeneration in vivo. Mol Ther. 2004 November; 10(5):844-54.

53. Germani A, Di Carlo A, Mangoni A, Straino S, Giacinti C, Turrini P, et al. Vascular endothelial growth factor modulates skeletal myoblast function. Am J Pathol. 2003 October; 163(4):1417-28.

54. Lee E W, Michalkiewicz M, Kitlinska J, Kalezic I, Switalska H, Yoo P, et al. Neuropeptide Y induces ischemic angiogenesis and restores function of ischemic skeletal muscles. J Clin Invest. 2003 June; 111(12):1853-62.

55. Lescaudron L, Peltekian E, Fontaine-Perus J, Paulin D, Zampieri M, Garcia L, et al. Blood borne macrophages are essential for the triggering of muscle regeneration following muscle transplant. Neuromuscul Disord. 1999 March; 9(2):72-80.

56. Motamed K, Blake D J, Angello J C, Allen B L, Rapraeger A C, Hauschka S D, et al. Fibroblast growth factor receptor-1 mediates the inhibition of endothelial cell proliferation and the promotion of skeletal myoblast differentiation by SPARC: a role for protein kinase A. J Cell Biochem. 2003 Oct. 1; 90(2):408-23.

57. Dusterhoft S, Pette D. Evidence that acidic fibroblast growth factor promotes maturation of rat satellite-cell-derived myotubes in vitro. Differentiation. 1999 November; 65(3):161-9.

58. Fu X, Cuevas P, Gimenez-Gallego G, Sheng Z, Tian H. Acidic fibroblast growth factor reduces rat skeletal muscle damage caused by ischemia and reperfusion. Chin Med J (Engl). 1995 March; 108(3):209-14.

59. Smith J, Schofield P N. The effects of fibroblast growth factors in long-term primary culture of dystrophic (mdx) mouse muscle myoblasts. Exp Cell Res. 1994 January; 210(1):86-93.

60. Oliver L, Raulais D, Vigny M. Acidic fibroblast growth factor (aFGF) in developing normal and dystrophic (mdx) mouse muscles. Distribution in degenerating and regenerating mdx myofibres. Growth Factors. 1992; 7(2):97-106.

61. Dell'Era P, Ronca R, Coco L, Nicoli S, Metra M, Presta M. Fibroblast growth factor receptor-1 is essential for in vitro cardiomyocyte development. Circ Res. 2003 Sep. 5; 93(5):414-20.

62. Husmann I, Soulet L, Gautron J, Martelly I, Barritault D. Growth factors in skeletal muscle regeneration. Cytokine Growth Factor Rev. 1996 October; 7(3):249-58.

63. Kurek J B, Nouri S, Kannourakis G, Murphy M, Austin L. Leukemia inhibitory factor and interleukin-6 are produced by diseased and regenerating skeletal muscle. Muscle Nerve. 1996 October; 19(10):1291-301.

64. Megeney L A, Perry R L, LeCouter J E, Rudnicki M A. bFGF and LIF signaling activates STAT3 in proliferating myoblasts. Dev Genet. 1996; 19(2):139-45.

65. Vakakis N, Bower J, Austin L. In vitro myoblast to myotube transformations in the presence of leukemia inhibitory factor. Neurochem Int. 1995 October-November; 27(4-5):329-35.

66. Martinou J C, Martinou I, Kato A C. Cholinergic differentiation factor (CDF/LIF) promotes survival of isolated rat embryonic motoneurons in vitro. Neuron. 1992 April; 8(4):737-44.

67. Sun L, Ma K, Wang H, Xiao F, Gao Y, Zhang W, et al. JAK1-STAT1-STAT3, a key pathway promoting proliferation and preventing premature differentiation of myoblasts. J Cell Biol. 2007 Oct. 8; 179(1):129-38.

68. Malm C, Sjodin T L, Sjoberg B, Lenkei R, Renstrom P, Lundberg I E, et al. Leukocytes, cytokines, growth factors and hormones in human skeletal muscle and blood after uphill or downhill running. J Physiol. 2004 May 1; 556(Pt 3):983-1000.

69. Zorzano A, Kaliman P, Guma A, Palacin M. Intracellular signals involved in the effects of insulin-like growth factors and neuregulins on myofibre formation. Cell Signal. 2003 February; 15(2):141-9.

70. Sakuma K, Watanabe K, Sano M, Uramoto I, Totsuka T. Differential adaptation of growth and differentiation factor 8/myostatin, fibroblast growth factor 6 and leukemia inhibitory factor in overloaded, regenerating and denervated rat muscles. Biochim Biophys Acta. 2000 Jun. 2; 1497(1):77-88.

71. Biesecker G. The complement SC5b-9 complex mediates cell adhesion through a vitronectin receptor. J Immunol. 1990 Jul. 1; 145(1):209-14.

72. Gullberg D, Sjoberg G, Veiling T, Sejersen T. Analysis of fibronectin and vitronectin receptors on human fetal skeletal muscle cells upon differentiation. Exp Cell Res. 1995 September; 220(1):112-23.

73. Wang X, Wu H, Zhang Z, Liu S, Yang J, Chen X, et al. Effects of interleukin-6, leukemia inhibitory factor, and ciliary neurotrophic factor on the proliferation and differentiation of adult human myoblasts. Cell Mol Neurobiol. 2008 January; 28(1):113-24.
74. Chen X, Mao Z, Liu S, Liu H, Wang X, Wu H, et al. Dedifferentiation of adult human myoblasts induced by ciliary neurotrophic factor in vitro. Mol Biol Cell. 2005 July; 16(7):3140-51.
75. Chen X P, Liu H, Liu S H, Wu Y, Wu H T, Fan M. [Exogenous rhCNTF inhibits myoblast differentiation of skeletal muscle of adult human in vitro]. Sheng Li Xue Bao. 2003 Aug. 25; 55(4):464-8.
76. Cannon J G. Intrinsic and extrinsic factors in muscle aging. Ann N Y Acad Sci. 1998 Nov. 20; 854:72-7.
77. Marques M J, Neto H S. Ciliary neurotrophic factor stimulates in vivo myotube formation in mice. Neurosci Lett. 1997 Sep. 26; 234(1):43-6.
78. Carrasco D I, English A W. Neurotrophin 4/5 is required for the normal development of the slow muscle fiber phenotype in the rat soleus. J Exp Biol. 2003 July; 206(Pt 13):2191-200.
79. Simon M, Porter R, Brown R, Coulton G R, Terenghi G. Effect of NT-4 and BDNF delivery to damaged sciatic nerves on phenotypic recovery of fast and slow muscles fibres. Eur J Neurosci. 2003 November; 18(9):2460-6.
80. Choi-Lundberg D L, Bohn M C. Ontogeny and distribution of glial cell line-derived neurotrophic factor (GDNF) mRNA in rat. Brain Res Dev Brain Res. 1995 Mar, 16; 85(1):80-8.
81. Lin L F, Doherty D H, Lile J D, Bektesh S, Collins F. GDNF: a glial cell line-derived neurotrophic factor for midbrain dopaminergic neurons. Science. 1993 May 21; 260(5111):1130-2.
82. Yang L X, Nelson P G. Glia cell line-derived neurotrophic factor regulates the distribution of acetylcholine receptors in mouse primary skeletal muscle cells. Neuroscience. 2004; 128(3):497-509.
83. Golden J P, DeMaro J A, Osborne P A, Milbrandt J, Johnson E M, Jr. Expression of neurturin, GDNF, and GDNF family-receptor mRNA in the developing and mature mouse. Exp Neurol. 1999 August; 158(2):504-28.
84. Henderson C E, Phillips H S, Pollock R A, Davies A M, Lemeulle C, Armanini M, et al. GDNF: a potent survival factor for motoneurons present in peripheral nerve and muscle. Science. 1994 Nov. 11; 266(5187):1062-4.
85. Heinrich G. A novel BDNF gene promoter directs expression to skeletal muscle. BMC Neurosci. 2003 Jun. 18; 4:11.
86. Mousavi K, Parry D J, Jasmin B J. BDNF rescues myosin heavy chain IIB muscle fibers after neonatal nerve injury. Am J Physiol Cell Physiol. 2004 July; 287(1):C22-9.
87. Chen J, von Bartheld C S. Role of exogenous and endogenous trophic factors in the regulation of extraocular muscle strength during development. Invest Ophthalmol Vis Sci. 2004 October; 45(10):3538-45.
88. Bordet T, Lesbordes J C, Rouhani S, Castelnau-Ptakhine L, Schmalbruch H, Haase G, et al. Protective effects of cardiotrophin-1 adenoviral gene transfer on neuromuscular degeneration in transgenic ALS mice. Hum Mol Genet. 2001 Sep. 1; 10(18):1925-33.
89. Dolcet X, Soler R M, Gould T W, Egea J, Oppenheim R W, Comella J X. Cytokines promote motoneuron survival through the Janus kinase-dependent activation of the phosphatidylinositol 3-kinase pathway. Mol Cell Neurosci. 2001 December; 18(6):619-31.
90. Lesbordes J C, Bordet T, Haase G, Castelnau-Ptakhine L, Rouhani S, Gilgenkrantz H, et al. In vivo electrotransfer of the cardiotrophin-1 gene into skeletal muscle slows down progression of motor neuron degeneration in pmn mice. Hum Mol Genet. 2002 Jul. 1; 11(14):1615-25.
91. Nishikawa J, Sakuma K, Sorimachi Y, Yoshimoto K, Yasuhara M. Increase of Cardiotrophin-1 immunoreactivity in regenerating and overloaded but not denervated muscles of rats. Neuropathology. 2005 March; 25(1):54-65.
92. Mitsumoto H, Klinkosz B, Pioro E P, Tsuzaka K, Ishiyama T, O'Leary R M, et al. Effects of cardiotrophin-1 (CT-1) in a mouse motor neuron disease. Muscle Nerve. 2001 June; 24(6):769-77.
93. Oppenheim R W, Wiese S, Prevette D, Armanini M, Wang S, Houenou L J, et al. Cardiotrophin-1, a muscle-derived cytokine, is required for the survival of subpopulations of developing motoneurons. J Neurosci. 2001 Feb. 15; 21(4):1283-91.
94. Peroulakis M E, Forger N G. Ciliary neurotrophic factor increases muscle fiber number in the developing levator ani muscle of female rats. Neurosci Lett. 2000 Dec. 22; 296(2-3):73-6.
95. Sheng Z, Pennica D, Wood W I, Chien K R. Cardiotrophin-1 displays early expression in the murine heart tube and promotes cardiac myocyte survival. Development. 1996 February; 122(2):419-28.
96. Jaworska-Wilczynska M, Wilczynski G M, Engel W K, Strickland D K, Weisgraber K H, Askanas V. Three lipoprotein receptors and cholesterol in inclusion-body myositis muscle. Neurology. 2002 Feb. 12; 58(3):438-45.
97. Caratsch C G, Santoni A, Eusebi F. Interferon-alpha, beta and tumor necrosis factor-alpha enhance the frequency of miniature end-plate potentials at rat neuromuscular junction. Neurosci Lett. 1994 Jan. 17; 166(1):97-100.
98. Al-Shanti N, Saini A, Faulkner S H, Stewart C E. Beneficial synergistic interactions of TNF-alpha and IL-6 in C2 skeletal myoblasts-potential cross-talk with IGF system. Growth Factors. 2008 April; 26(2):61-73.
99. Fowler V M, Sussmann M A, Miller P G, Flucher B E, Daniels M P. Tropomodulin is associated with the free (pointed) ends of the thin filaments in rat skeletal muscle. J Cell Biol. 1993 January; 120(2):411-20.
100. Jin P, Sejersen T, Ringertz N R. Recombinant platelet-derived growth factor-BB stimulates growth and inhibits differentiation of rat L6 myoblasts. J Biol Chem. 1991 Jan. 15; 266(2):1245-9.
101. Kudla A J, John M L, Bowen-Pope D F, Rainish B, Olwin B B. A requirement for fibroblast growth factor in regulation of skeletal muscle growth and differentiation cannot be replaced by activation of platelet-derived growth factor signaling pathways. Mol Cell Biol. 1995 June; 15(6):3238-46.
102. Quinn L S, Ong L D, Roeder R A. Paracrine control of myoblast proliferation and differentiation by fibroblasts. Dev Biol. 1990 July; 140(1):8-19.
103. Yablonka-Reuveni Z. Development and postnatal regulation of adult myoblasts. Microsc Res Tech. 1995 Apr. 1; 30(5):366-80.
104. Gold M R. The effects of vasoactive intestinal peptide on neuromuscular transmission in the frog. J Physiol. 1982 June; 327:325-35.
105. Gozes I, Steingart R A, Spier A D. NAP mechanisms of neuroprotection. J Mol Neurosci. 2004; 24(1):67-72.
106. Aracil A, Belmonte C, Calo G, Gallar J, Gozes I, Hoyer D, et al. Proceedings of Neuropeptides 2004, the XIV European Neuropeptides Club meeting. Neuropeptides. 2004 December; 38(6):369-71.
107. Robertson T A, Dutton N S, Martins R N, Taddei K, Papadimitriou J M. Comparison of astrocytic and myocytic metabolic dysregulation in apolipoprotein E deficient and human apolipoprotein E transgenic mice. Neuroscience. 2000; 98(2):353-9.
108. Langen R C, Schols A M, Kelders M C, Wouters E F, Janssen-Heininger Y M. Enhanced myogenic differentiation by extracellular matrix is regulated at the early stages of myogenesis. In Vitro Cell Dev Biol Anim. 2003 March-April; 39(3-4):163-9.
109. Foster R F, Thompson J M, Kaufman S J. A laminin substrate promotes myogenesis in rat skeletal muscle cultures: analysis of replication and development using antidesmin and anti-BrdUrd monoclonal antibodies. Dev Biol. 1987 July; 122(1):11-20.
110. Hantai D, Rao J S, Reddy B R, Festoff B W. Developmental appearance of thrombospondin in neonatal mouse skeletal muscle. Eur J Cell Biol. 1991 August; 55(2):286-94.
111. Kuhl U, Ocalan M, Timpl R, von der Mark K. Role of laminin and fibronectin in selecting myogenic versus fibrogenic cells from skeletal muscle cells in vitro. Dev Biol. 1986 October; 117(2):628-35.
112. Lyles J M, Amin W, Weill C L. Matrigel enhances myotube development in a serum-free defined medium. Int J Dev Neurosci. 1992; 10(1):59-73.
113. Song W K, Wang W, Foster R F, Bielser D A, Kaufman S J. H36-alpha 7 is a novel integrin alpha chain that is developmentally regulated during skeletal myogenesis. J Cell Biol. 1992 May; 117(3):643-57.
114. Swasdison S, Mayne R. Formation of highly organized skeletal muscle fibers in vitro. Comparison with muscle development in vivo. J Cell Sci. 1992 July; 102 (Pt 3):643-52.
115. Wang P, Yang G, Mosier D R, Chang P, Zaidi T, Gong Y D, et al. Defective neuromuscular synapses in mice lacking amyloid precursor protein (APP) and APP-Like protein 2. J Neurosci. 2005 Feb. 2; 25(5):1219-25.
116. Yang L, Wang B, Long C, Wu G, Zheng H. Increased asynchronous release and aberrant calcium channel activation in amyloid precursor protein deficient neuromuscular synapses. Neuroscience. 2007 Nov. 23; 149(4):768-78.
117. Akaaboune M, Allinquant B, Farza H, Roy K, Magoul R, Fiszman M, et al. Developmental regulation of amyloid precursor protein at the neuromuscular junction in mouse skeletal muscle. Mol Cell Neurosci. 2000 April; 15(4):355-67.
118. Hall B K, Miyake T. All for one and one for all: condensations and the initiation of skeletal development. Bioessays. 2000 February; 22(2):138-47.
119. Fan C M, Tessier-Lavigne M. Patterning of mammalian somites by surface ectoderm and notochord: evidence for sclerotome induction by a hedgehog homolog. Cell. 1994 Dec. 30; 79(7):1175-86.
120. Munsterberg A E, Kitajewski J, Bumcrot D A, McMahon A P, Lassar A B. Combinatorial signaling by Sonic hedgehog and Wnt family members induces myogenic bHLH gene expression in the somite. Genes Dev. 1995 Dec. 1; 9(23):2911-22.
121. Nelson C E, Morgan B A, Burke A C, Laufer E, DiMambro E, Murtaugh L C, et al. Analysis of Hox gene expression in the chick limb bud. Development. 1996 May; 122(5):1449-66.
122. Cossu G, Tajbakhsh S, Buckingham M. How is myogenesis initiated in the embryo? Trends Genet. 1996 June; 12(6):218-23.
123. Currie P D, Ingham P W. Induction of a specific muscle cell type by a hedgehog-like protein in zebrafish. Nature. 1996 Aug. 1; 382(6590):452-5.
124. Norris W, Neyt C, Ingham P W, Currie P D. Slow muscle induction by Hedgehog signalling in vitro. J Cell Sci. 2000 August; 113 (Pt 15):2695-703.
125. Elia D, Madhala D, Ardon E, Reshef R, Halevy 0. Sonic hedgehog promotes proliferation and differentiation of adult muscle cells: Involvement of MAPK/ERK and PI3K/Akt pathways. Biochim Biophys Acta. 2007 September; 1773(9): 1438-46.
126. Pagan S M, Ros M A, Tabin C, Fallon J F. Surgical removal of limb bud Sonic hedgehog results in posterior skeletal defects. Dev Biol. 1996 Nov. 25; 180(1):35-40.
127. Holler, F. James; Skoog, Douglas A; Crouch, Stanley R (2007). "Chapter 1". Principles of Instrumental Analysis (6th Edition ed.). Cengage Learning. p. 9. ISBN 9780495012016.
128. King T, Pozzi M, Manara A (2000). Piezoactuators for 'real-world' applications—Can they deliver sufficient displacement? Power Engineering J, 14, 3: 105-110
129. X. J. Lou (2009), Polarization fatigue in ferroelectric thin films and related materials. 105, 024101-1
130. Madhu Santosh Ku Mutyala•Deepika Bandhanadham•Liu Pan•Vijaya Rohini Pendyala•Hai-Feng Ji ( ). Mechanical and electronic approaches to improve the sensitivity of microcantilever sensors. Acta Mech Sin, 25:1-12
131. Das, Kerry Wilson, Peter Molnar and James J Hickman ( ). Differentiation of skeletal muscle and integration of myotubes with silicon microstructures using serum-free medium and a synthetic silane substrate. Nature Protocols 2.7, 1795(7).
132. Philip S. Waggoner and Harold G. Craighead (2007). Micro- and nanomechanical sensors for environmental, chemical, and biological detection. Lab Chip, 7, 1238-1255
133. Bren-Mattison Y, Olwin B B. Sonic hedgehog inhibits the terminal differentiation of limb myoblasts committed to the slow muscle lineage. Dev Biol. 2002 Feb. 15; 242(2):130-48.
134. Maves L, Waskiewicz A J, Paul B, Cao Y, Tyler A, Moens C B, et al. Pbx homeodomain proteins direct Myod activity to promote fast-muscle differentiation. Development. 2007 September; 134(18):3371-82.
135. Koleva M, Kappler R, Vogler M, Herwig A, Fulda S, Hahn H. Pleiotropic effects of sonic hedgehog on muscle satellite cells. Cell Mol Life Sci. 2005 August; 62(16): 1863-70.
136. Bandi E, Jevsek M, Mars T, Jurdana M, Formaggio E, Sciancalepore M, et al. Neural agrin controls maturation of the excitation-contraction coupling mechanism in human myotubes developing in vitro. Am J Physiol Cell Physiol. 2008 January; 294(1):C66-73.
137. Sanes J R. Genetic analysis of postsynaptic differentiation at the vertebrate neuromuscular junction. Curr Opin Neurobiol. 1997 February; 7(1):93-100.

TABLE 1

Medium Composition 1

| S. No | Component | Amount | Catalogue # | Source | References |
|---|---|---|---|---|---|
| 1. | Neurobasal | 500 ml | 10888 | Gibco/Invitrogen | [41] |
| 2. | Antibiotic-Antimycotic | 5 ml | 15240-062 | Gibco/Invitrogen | |
| 3. | G5 Supplement (100X) | 5 ml | 17503-012 | Gibco/Invitrogen | [42-51] |
| 4. | VEGF$_{165\ r\ Human}$ | 10 μg | P2654 | Gibco/Invitrogen | [52-55] |
| 5. | Acidic FGF | 12.5 μg | 13241-013 | Gibco/Invitrogen | [42, 49, 51, 56-61] |
| 6. | Heparin Sulfate | 50 μg | D9809 | Sigma | [42, 49, 51, 56-61] |
| 7. | LIF | 10 μg | L5158 | Sigma | [62-70] |
| 8. | Vitronectin (Rat Plasma) | 50 μg | V0132 | Sigma | [71, 72] |
| 9. | CNTF | 20 μg | CRC 401B | Cell Sciences | [73-77] |
| 10. | NT-3 | 10 μg | CRN 500B | Cell Sciences | [15] |
| 11. | NT-4 | 10 μg | CRN 501B | Cell Sciences | [78, 79] |
| 12. | GDNF | 10 μg | CRG 400B | Cell Sciences | [80-84] |
| 13. | BDNF | 10 μg | CRB 600B | Cell Sciences | [79, 85, 86] |
| 14. | CT-1 | 10 μg | CRC 700B | Cell Sciences | [87-95] |

TABLE 2

Medium Composition 2

| No | Component(s) | Amount | Catalog | Source | References |
|---|---|---|---|---|---|
| 1 | Neurobasal | 500 ml | 10888 | Invitrogen/Gibco | [41] |
| 2 | Antibiotic-antimycotic | 5 ml | 15240-062 | Invitrogen/Gibco | |
| 3 | Cholesterol (250X) | 5 ml | 12531 | Invitrogen/Gibco | [96] |
| 4 | TNF-alpha, human | 10 μg | T6674 | Sigma-Aldrich | [97-99] |
| 5 | PDGF BB | 50 μg | P4056 | Sigma-Aldrich | [62, 100-103] |
| 6 | Vasoactive intestinal peptide (VIP) | 250 μg | V6130 | Sigma-Aldrich | [104] |
| 7 | Insulin-like growth factor 1 | 25 μg | I2656 | Sigma-Aldrich | [68, 69, 98] |
| 8 | NAP | 1 mg | 61170 | AnaSpec, Inc. | [105, 106] |
| 9 | r-Apolipoprotein E2 | 50 μg | P2002 | Panvera, Madison, WI | [107] |
| 10 | Laminin, mouse purified | 2 mg | 08-125 | Millipore | [108-114] |
| 11 | Beta amyloid (1-40) | 1 mg | AG966 | Millipore | [115-117] |
| 12 | Human Tenascin-C protein | 100 μg | CC065 | Millipore | [118] |
| 13 | rr-Sonic hedgehog, Shh N-terminal | 50 μg | 1314-SH | R&D Systems | [7, 119-129] |
| 14 | rr-Agrin (C terminal) | 50 μg | 550-AG-100 | R&D Systems | [130, 131] |

TABLE 3

B-27 ™ Serum-Free Supplement Media ingredients

| | Components | Concentration (mg/L) |
|---|---|---|
| Vitamins | Biotin | 0.10 |
| | DL Alpha Tocopherol Acetate | 1.0 |
| | DL Alpha-Tocopherol | 1.0 |
| | Vitamin A | 0.1-0.2 |
| Proteins | BSA, fatty acid free Fraction V | 2500.0 |
| | Catalase | 2.5 |
| | Human Recombinant Insulin | 4.0 |
| | Human Transferrin | 5.0 |
| | Superoxide Dismutase | 2.5 |
| Other Components | Corticosterone | 0.02 |
| | D-Galactose | 15.0 |
| | Ethanolamine HCl | 1.0 |
| | Glutathione (reduced) | 1.0 |
| | L-Carnitine HCl | 2.0 |
| | Linoleic Acid | 1.0 |
| | Linolenic Acid | 1.0 |
| | Progesterone | 0.0063 |
| | Putrescine 2HCl | 16.1 |
| | Sodium Selenite | 0.035 |
| | T3 (triodo-I-thyronine) | 0.002 |

TABLE 4

Neurobasal ™ media formulation

| | Components | Concentration (mg/L) |
|---|---|---|
| Amino Acids | Glycine | 30.0 |
| | L-Alanine | 2.0 |
| | L-Arginine hydrochloride | 84.0 |
| | L-Asparagine-H2O | 0.83 |
| | L-Cysteine | 31.5 |
| | L-Histidine hydrochloride-H2O | 42.0 |
| | L-Isoleucine | 105.0 |
| | L-Leucine | 105.0 |
| | L-Lysine hydrochloride | 146.0 |
| | L-Methionine | 30.0 |
| | L-Phenylalanine | 66.0 |
| | L-Proline | 7.76 |
| | L-Serine | 42.0 |
| | L-Threonine | 95.0 |
| | L-Tryptophan | 16.0 |
| | L-Tyrosine | 72.0 |
| | L-Valine | 94.0 |
| Vitamins | Choline chloride | 4.0 |
| | D-Calcium pantothenate | 4.0 |
| | Folic Acid | 4.0 |
| | Niacinamide | 4.0 |
| | Pyridoxal hydrochloride | 4.0 |
| | Riboflavin | 0.4 |
| | Thiamine hydrochloride | 4.0 |
| | Vitamin B12 | 0.0068 |
| | i-Inositol | 7.2 |
| Inorganic Salts | Calcium. Chloride (CaCl2) (anhyd.) | 200.0 |
| | Ferric Nitrate (Fe(NO3)3"9H2O) | 0.1 |
| | Magnesium Chloride (anhydrous) | 77.3 |
| | Potassium Chloride (KCl) | 400.0 |
| | Sodium Bicarbonate (NaHCO3) | 2200.0 |
| | Sodium Chloride (NaCl) | 3000.0 |
| | Sodium Phosphate monobasic (NaH2PO4—H2O) | 125.0 |
| | Zinc sulfate (ZnSO4—7H2O) | 0.194 |
| Other Components | D-Glucose (Dextrose) | 4500.0 |
| | HEPES | 2600.0 |
| | Phenol Red | 8.1 |
| | Sodium Pyruvate | 25.0 |

TABLE 5

| | Glutamax ™ media formulation | |
| --- | --- | --- |
| | Components | Concentration (mM) |
| Peptides | L-alanyl-L-glutamine | 200 |
| Inorganic Salts | Sodium Chloride (NaCl) | 145 |

That which is claimed:

1. A method of maintaining a muscle cell culture, the method comprising:
    maintaining the muscle cell culture in a serum-free maintenance medium comprising the components at the concentrations listed in Table 3, the components at the concentrations listed in Table 4, the components at the concentrations listed in Table 5, creatine, estrogen, and cholesterol wherein the cells in the muscle cell culture consist of muscle cells.

2. The method of claim 1, wherein the muscle cell culture is maintained in the serum-free maintenance medium for at least 30 days.

3. The method of claim 2, wherein the muscle cell culture is maintained in the serum-free maintenance medium for at least 50 days.

4. The method of claim 1, further comprising plating the muscle cell culture onto a non-biological growth substrate prior to maintaining the muscle cell culture in the serum-free maintenance medium.

5. The method of claim 4, wherein the non-biological growth substrate comprises a silane molecule.

6. The method of claim 5, wherein the non-biological growth substrate is trimethoxy-silylpropyl-diethylenetriamine (DETA).

7. The method of claim 1, further comprising plating the muscle cell culture at a density of 700 to 1000 muscle cells per square millimeter prior to maintaining the muscle cell culture in the serum-free maintenance medium.

8. The method of claim 1, further comprising replenishing the serum-free maintenance medium every 1 to 5 days.

9. The method of claim 8, further comprising replenishing the serum-free maintenance medium every 3 days.

10. The method of claim 1, further comprising incubating the muscle cell culture in a first serum-free medium prior to maintaining the muscle cell culture in the serum-free maintenance medium.

11. The method of claim 10, wherein the first serum-free medium comprises a factor selected from the group consisting of vascular endothelial growth factor (VEGF), acidic fibroblast growth factor (FGF), heparin sulfate, leukemia inhibitory factor (LIF), vitronectin, ciliary neurotrophic factor (CNTF), neurotrophin-3 (NT-3), neurotrophin-4 (NT-4), glial cell-derived neurotrophic factor (GDNF), brain-derived neurotrophic factor (BDNF), cardiotrophin-1 (CT-1), cholesterol, tumor necrosis factor alpha (TNF-alpha), platelet derived growth factor (PDGF), vasoactive intestinal peptide, insulin-like growth factor 1, neutrophil activating protein (NAP), r-Apolipoprotein, laminin, beta amyloid, tenascin-C protein, rr-sonic hedgehog, and rr-agrin.

12. The method of claim 11, wherein the first serum-free medium comprises vitronectin.

13. The method of claim 12, wherein the first serum-free medium is a mixture of approximately equal volumes of the medium composition of Table 1 and the medium composition of Table 2.

14. The method of claim 10, wherein the muscle cell culture is maintained in the first serum-free medium from 2 to 6 days.

15. The method of claim 14, wherein the muscle cell culture is maintained in the first serum-free medium for 4 days.

* * * * *